United States Patent
DeHoff et al.

(10) Patent No.: US 9,447,422 B2
(45) Date of Patent: Sep. 20, 2016

(54) AUTONOMOUS REPLICATION SEQUENCES AND EPISOMAL DNA MOLECULES

(71) Applicant: Synthetic Genomics, Inc., La Jolla, CA (US)

(72) Inventors: Peter DeHoff, Poway, CA (US); Leah Soriaga, San Diego, CA (US); Srividya Akella, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 29 days.

(21) Appl. No.: 14/099,682

(22) Filed: Dec. 6, 2013

(65) Prior Publication Data

US 2015/0094209 A1    Apr. 2, 2015

Related U.S. Application Data

(60) Provisional application No. 61/734,285, filed on Dec. 6, 2012.

(51) Int. Cl.
| | | |
|---|---|---|
| C12N 15/82 | (2006.01) | |
| C12Q 1/68 | (2006.01) | |
| C12P 21/02 | (2006.01) | |

(52) U.S. Cl.
CPC ....... *C12N 15/8213* (2013.01); *C12N 15/8271* (2013.01); *C12P 21/02* (2013.01); *C12Q 1/6876* (2013.01); *C12Q 2600/16* (2013.01)

(58) Field of Classification Search
None
See application file for complete search history.

(56) References Cited

U.S. PATENT DOCUMENTS

| | | |
|---|---|---|
| 5,935,789 A | 8/1999 | Rhee et al. |
| 2007/0065905 A1 | 3/2007 | Branduardi et al. |
| 2008/0193977 A1 | 8/2008 | Finnis et al. |
| 2010/0050301 A1 | 2/2010 | Mendez et al. |
| 2012/0288918 A1 | 11/2012 | Hopkins et al. |

FOREIGN PATENT DOCUMENTS

| | | |
|---|---|---|
| WO | WO 2012/123429 A1 | 9/2012 |
| WO | WO 2012/178101 A2 | 12/2012 |

OTHER PUBLICATIONS

GenBank_JU979347, TSA: Nannochloropsis gaditana CCMP526 NGA Contig36786 mRNA sequence, May 16, 2012 [online]. [Retrieved on Feb. 20, 2014]. Retrieved from the Internet: <URL: http://www.ncbi.nlm.nih.gov/nuccore/JU979347> Source, Definition, Features, and Origin.
GenBank_JU970348, TSA: Nannochloropsis gaditana CCMP526 NGA_Contig31203 mRNA sequence, May 16, 2012 [online]. [Retrieved on Feb. 20, 2014]. Retrieved from the Internet: <URL http://www.ncbi.nlm.nih.gov/nuccore/JU970348> Source, Definition, Features, and Origin.
GenBank_JU978004, TSA: Nannochloropsis gaditana CCMP526 NGA_Contig21411 mRNA sequence, May 16, 2012 [online]. [Retrieved on Jan. 27, 2014]. Retrieved from the Internet <URL: http://www.ncbi.nlm.nih.gov/nuccore/JU978004> Definition, and Origin.
International Search Report Regarding PCT/US2013/073717 (6 pages), 2014.
Basu et al.: "*Efficient assembly of de novo human artificial chromosomes from large genomic loci.*"; BMC Biotechnol. (2005) 5:21.
Clyne, R. et al.: "*Identification of Autonomously Replicating Sequence (ARS) Elements in Eukaryotic Cells Methods: A Companion to Methods in Enzymology*" (1997) 13: 221-233.
Gilbert: "*Making Sense of Eukaryotic DNA Replication Origins*" Science 2001) 294:96-100.
Henning et al.: "*Human artificial chromosomes generated by modification of a yeast artificial chromosome containing both human alpha satellite and single-copy DNA sequences.*"; Proc. Nat'l, Acad. Sci, USA (1999) 96:592-97.
Kim, M.S. et al.: "*Enhanced expression of EGFP gene in CHSE-214 cells by an ARS element from mud loach (Misgurnus mizolepis)*". Plasmid (2007) 58:228-239.
Smith et al.: "*An unusual form of transcriptional silencing in yeast ribosomal DNA.*" ; Genes Dev. (1997) 11:241-54.
Van'T Hof, J.: "*DNA Replication in Plants Chapter 38 of DNA Replication in Eukaryotic Cells.*", Cold Spring Harbor Laboratory Press (1996) 1005-1014.

*Primary Examiner* — Michele K Joike
(74) *Attorney, Agent, or Firm* — DLA Piper LLP (US)

(57) ABSTRACT

The present invention provides autonomous replication sequences (ARSs) isolated from *Nannochloropsis* that support the replication of episomal DNA molecules (EDMs) in eukaryotic cells. The ARSs and EDMs provided herein can be used for expressing genes in organisms including algae and heterokonts.

28 Claims, 10 Drawing Sheets

Figure 2a

```
                                                                  ******  *******************************
                                                                        AACAAGTTTTGATTTTTGTGTTGTTGTCGTATTTTTACG
GAGGACATCCGG------ATTTTAACAAAACATCGTGAAACAAG-TTTGATTTTTGTGTTTGTGTTGTCGTATTTTTACG
GAGGACATCCGG------ATTTTAACAAAACATCGTGAAACAAG-TTTGATTTTTGTGTTTGTGTTGTCGTATTTTTACG
GAGGACATCCGG------ATTTTAACAAAACATCGTGAAACAAG-TTTGATTTTTGTGTTTGTGTTGTCGTATTTTTACG
                  ------AACAAGAACATCGTGAAACAAG-TTTGATTTTTGTGTTTGTGTTGTCGTATTTTTACG
GAGGACATCCGG------ATTTTAACAAAACATCGTGAAACAAG-TTTGATTTTTGTGTTTGTGTTGTCGTATTTTTACG
GAGGACATCCGG------ATTTTAACAAAACATCGTGAAACAAG-TTTGATTTTTGTGTTTGTGTTGTCGTATTTTTACG
GAGGACATCCGG------ATTTTAACAAAACATCGTGAAACAAG-TTTGATTTTTGTGTTTGTGTTGTCGTATTTTTACG
....760.......770........780........790........800........810........820

************   **********   *********************   ******   ******                                      114
                                                                                                          893
                                                                                                          728
                                                                                                          897
                                                                                                          116
                                                                                                          898
                                                                                                          898
                                                                                                          897
CAGGAAAATGTC--AGCCGATACCTTCGAGCTACCTGGGGTTGTCTTTTTGAAGTCCCAGCATTGTGTTCACCTACTAT
CAGGAAAATGTC--AGCCGATACCTTCGAGCTACCTGGGGTTGTCTTTTTGAAGTCCCAGCATTGTGTTCACCTACTAT
CAGGAAAATGTCAGAGCCGATACATTCGAGCTACCTGGGGTTGTCTTTTT-AGAGTCCCAGCATTGTGTTCACCTACGAT
CAGGAAAATGTCAGAGCCGATACATTCGAGCTACCTGGGGTTGTCTTTTT-AGAGTCCCAGCATTGTGTTCACCTACGAT
CAGGAAAATGTCAGAGCCGATACATTCGAGCTACCTGGGGTTGTCTTTTTAAGAGTCCCAGCATTGTGTTCACCTACGAT
CAGGAAAATGTCAGAGCCGATACATTCGAGCTACCTGGGGTTGTCTTTTTAAGAGTCCCAGCATTGTGTTCACCTACGAT
CAGGAAAATGTCAGAGCCGATACATTCGAGCTACCTGGGGTTGTCTTTTTAAGAGTCCCAGCATTGTGTTCACCTACGAT
CAGGAAAATGTCAGAGCCGATACATTCGAGCTACCTGGGGTTGTCTTTTTAAGAGTCCCAGCATTGTGTTC-CCTACGAT
....830........840........850........860........870........880........890........900
```

Figure 2b

```
*******   *******   ******************   *   **************   ***   ********
          AGTGCACTGCTGCAAGTGAATTGAATTCATTTGCGATAGCCACAAAACTAGCTAAACTATACAACTTACGAATT                264
          AGTGCACTGCTGCAAGTGAATTGAATTCATTTGCGATAGCCACAAAACTAGCTAAACTATACAACTTACGAATT                1043
          AGTGCACTGGCTGCAAGTGAATTAAATTCATTTGCGATAGCCACAAAACTAGCTAAACTATACAACTTACGAATT               862
          AGTGCCATGGCTGCAAGTGAATTAAATTCATTTGCGATAACTAACCACAAAACTAGC----------CAATTTACGAATC          1031
          AGTGCCATGGCTGCAAGTGAATTAAATTCATTTGCGATAACTAACCACAAAACTAGC----------CAATTTACGAATC          250
          AGTGCCATGGCTGCAAGTAAATTCATTTGCGATAAACCACAAAACTAGC----------CAATTTACGAATC                  1032
          AGTGCCATGGCTGCAAGTAAATTCATTTGCGATAACCACAAAACTAGC----------CAATTTACGAATC                   1032
          AGTGCCATGGCTGCAAGTAAATTCATTTGCGATAACCACAAAACTAGC----------CAATTTACGAATC                   1031
          ....910.......920.......930.......940.......950.......960.......970

* *****   *******   *****************   **************   **********   ***   *********
          TATGAAGTTGTTTTTTCGTTCTACGGTCCTCCTTGTGTAACCCATCGATGTTGCTTCAAGAACTTCGATATGGGCTCTG           264
          TATGAAGTTGTTTTTTCGTTCTACGGTCCTCCTTGTGTAACCCATCGATGTTGCTTCAAGAACTTCGATATGGGCTCTG           1043
          TGTGAAGAAGTTTTTCGCGTTCTACGGTCCTCCTTGTAGTAACCCATCGATGTTGCTTCAAGAACTTCGATATGGGCTCTG         862
          TGTGAAGAAGTTTTTCGCGTTCTACGGTCCTCCTTGTAGTAACCCATCGATGTTGCTTCAA------GATATGGGCGCTG          1031
          TGTGAAGAAGTTTTTCGCGTTCTACGGTCCTCCTTGTAGTAACCCATCGATGTTGCTTCAA------GATATGGGCGCTG          250
          TGTGAAGAAGTTTTTCGCGTTCTACGGTCCTCCTTGTAGTAACCCATCGATGTTGCTTCAA------GATATGGGCGCTG          1032
          TGTGAAGAAGTTTTTCGCGTTCTACGGTCCTCCTTGTAGTAACCCATCGATGTTGCTTCAA------GATATGGGCGCTG          1032
          TGTGAAGAAGTTTTTCGCGTTCTACGGTCCTCCTTGTAGTAACCCATCGATGTTGCTTCAA------GATATGGGCGCTG          1031
          ....980.......990......1000......1010......1020......1030......1040......1050
```

Figure 2c

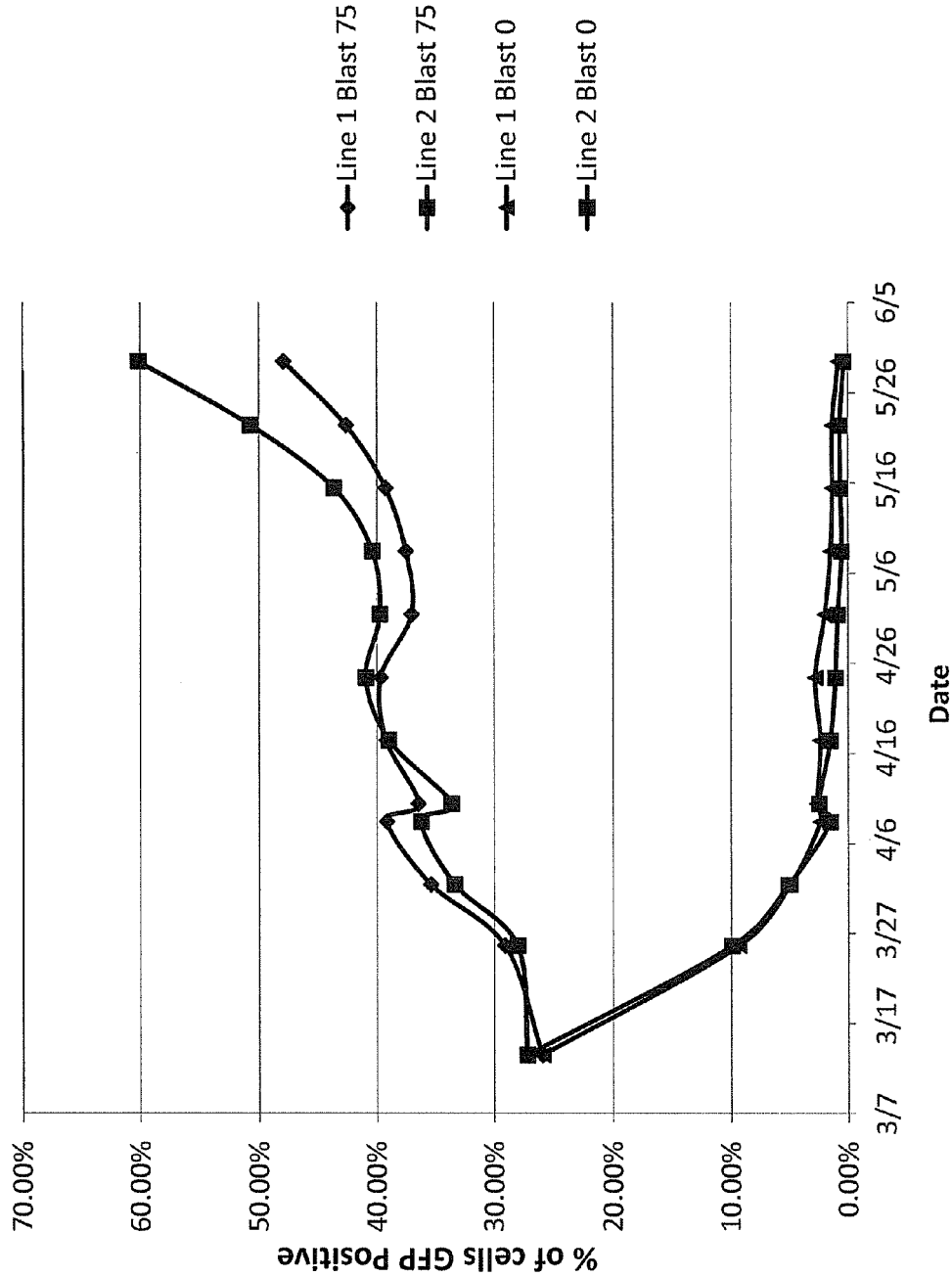

SEQUENCE LISTING

```
<160> NUMBER OF SEQ ID NOS: 27

<210> SEQ ID NO 1
<211> LENGTH: 1627
<212> TYPE: DNA
<213> ORGANISM: Nannochloropsis gaditana
<220> FEATURE:
<221> NAME/KEY: misc_feature
<223> OTHER INFORMATION: NgARS1.6

<400> SEQUENCE: 1
cgtgtgagag aaaaaaacct tttaccatct ttcccacatg agtgtgaagt ggtaagaaaa      60
caatcatccc accaacgtac atccgggtag ctttaaatga aaccctcaga actcgggtca     120
tatgccttcc accagacaag tcctttaact tccccgtctt tatacatccg ggtaactttc     180
gatggatcag cgtctgtatc cgggtagctt ttgcctaatc ttcatttgac atgaagtatc     240
tggacgataa tatttacggg ttcttcgagg acatccgggc attttaacaa aacatcgtga     300
aacaagtttg atttttgtgt tgtcgtattt ttacgcagga aaatgtcaga gccgatacat     360
tcgagctacc tggggttgtc tttttaagag tcccagcatt gtgttcacct acgatagtgc     420
atggctgcaa gtaaattcat tttgcgataa ccacaaaact agccaattta cgaatctgtg     480
aagaagtttt tcgcgttcta cggtcctctt gtagtaaccc atcgatgttg cttcaagata     540
tgggcgctgg tcgatggaaa aaaccacagg actagttaaa atcatagatt ccacgaaatt     600
attaaaatat tattttttcat gctccataca gaaattgccg ataggaaaaa ccactttttt     660
accactctca cattagtgcg agatggtgaa gatagaactt tccctcgaac atacgtccgg     720
gtagctttta ctgaaaagcc ctgagaaccc gtactgtacg agtgtgtcgc gccttccacg     780
ccgacgtcat cttcgtcttg gctgcctttg tacatccggg ttatttctga gacccttcta     840
ttagtcttgc gtatacgatg caaggttaac acttcacatg tcgagtggac atgtcctcca     900
cataaaccac agactcgatg tcgacttacg tcgatgacat gacatgtcat cggttgtctt     960
tcatgtcgac acttctcgac atctgcgaaa agccctgaga acttggatga gtaccccacc    1020
atggattttt tgggaaatt cagcatacat ccggtcgatg gaaacaacca caggactagt    1080
acaaattata gaatacacgg aattattgag gtgtgaattt tcatcctgca tacaaaaaaa    1140
ttccctagtt cgctgttttt tcggaagttg ccatcataac cgagagaggc ctgatgacgg    1200
tattgaagac agcacattcg tgacatggaa tgtcgtgcca tgtcttttta accccaagca    1260
gttaaaattt ctggcggtta atcgatgtca ctgtgcatca tccctctcat gtccaatgtc    1320
```

```
aagcgtataa ccataagcgc tcttgccata agacagcatt ttattcacat gaaataatca    1380
aaaacatgga ggcatgaata agatcttttg caaaggaatt cgactcactt ttcgatggga    1440
tgtgttttct ttcatgcttc aaaactaatg tagtattcac atcgctgttc tataggccct    1500
tttcctaata cccatgcacg agcgagcgtc atgactgagc aaaccactgt agtacctgct    1560
cataattggg cactgtcctc aaatctttc caaccgctga gatggaaacc ggctttgaaa     1620
tggcccg                                                             1627

<210> SEQ ID NO 2
<211> LENGTH: 86
<212> TYPE: DNA
<213> ORGANISM: Nannochloropsis gaditana
<220> FEATURE:
<221> NAME/KEY: misc_feature
<223> OTHER INFORMATION: Repeat Sequence from NgARS1.6

<400> SEQUENCE: 2
ggtcgatgga aaaaccaca ggactagtta aaatcataga ttccacgaaa ttattaaaat      60 attattttc atgctccata cagaaa                                          86

<210> SEQ ID NO 3
<211> LENGTH: 87
<212> TYPE: DNA
<213> ORGANISM: Nannochloropsis gaditana
<220> FEATURE:
<221> NAME/KEY: misc_feature
<223> OTHER INFORMATION: Repeat Sequence from NgARS1.6

<400> SEQUENCE: 3
cggtcgatgg aaacaaccac aggactagta caaattatag aatacacgga attattgagg     60
tgtgaatttt catcctgcat acaaaaa                                        87

<210> SEQ ID NO 4
<211> LENGTH: 87
<212> TYPE: DNA
<213> ORGANISM: Nannochloropsis gaditana
<220> FEATURE:
<221> NAME/KEY: misc_feature
<223> OTHER INFORMATION: ARS repeat consensus sequence

<400> SEQUENCE: 4
cggtcgatgg aaamaaccac aggactagtw maaatyatag awtmcacgra attattrarr     60
trtkawtttt catsctscat acaraaa                                        87

<210> SEQ ID NO 5
<211> LENGTH: 4421
<212> TYPE: DNA
<213> ORGANISM: Nannochloropsis gaditana
<220> FEATURE:
<221> NAME/KEY: misc_feature
<223> OTHER INFORMATION: NgARS1

<400> SEQUENCE: 5
aacaagtttt gatttttgtg ttgtcgtatt tttacgcagg aaaatgtcag ccgatacctt     60
cgagctacct ggggttgtct tttttgaagt cccagcattg tgttcaccta ctatagtgca   120
ctgctgcaag tgaattcatt ttgcgatagc cacaaaacta gctaaactat acaacttacg   180
aatttatgaa gttgtttttt tcgttctacg gtcctcttgt tgtaacccat cgatgttgct   240
tcaagaactt cgatatgggc tctggtcgat ggaaaaaacc acaggactag ttaaaatcat   300
```

```
agattccacg aaattattga aatattattt ttcatgctac atacagaaat tcctgacaga    360
gaaaaaaacc acttttttac cactctcaca tcagtgcgag atggtataga gcgagctatc    420
cctcgaacat acatccgggt agcttttact gaaaagccct gagaacctct actgtacgag    480
cgtgtcgcgc cctccacgcc gacgtcatct tcttggctgc cttttgtacat ccgggttgtt   540 tctgaaacct ttctattagt attgcgtgta cgatgcaagg tttacacttt gacatgtcga    600
gcgtcgacat gtcctcgaca tgaatcacag actcgatatc gacataaatg tagatgacat    660
gacatgtcat catttgtctg taatgtcgac acttctcgac atctatggaa agccttgaga    720
acttcgacga gttcctcacc ttcccatccc gatgcatgta aggaaaatca tctgaactcc    780
agcatatatc cgggtagctt aacgaagcac acttgtgaaa tgtaccgcgt gccccgcctt    840
ccctccaaaa tactcgtcca tctcaacgtt tcctctgatc aaacatccgg ttaccttttaa   900 aaccttactt gtcaggcgac agcgcatcat atgtttccgg gtagttacac gactaccacc    960
ctctatacac ataaatccag gggttttcct agcgtccttt gatttgaaaa tccgggtagc   1020
ttgatgattg tagatattaa gttgtgttcg tttcaaacag caactagaaa gtgcgtttta   1080
agatttggat gatttattcg agaaacagaa gtcaaaaaat gaacttgcca acaaaaattc   1140
gcttaccaaa ctggtcgaac aaatggtttt ttacttctta ctatgaaaaa ttcgttattt   1200
tacaagaacg attaaaaacc tggcctccta tttgagactc tacccttttg agtcctttct   1260
atgtacccct tttcggcccc tggagttatt cttgcaaagt tgtcatcctt ggtcgatttc   1320
gcatttattc tttctcgcct tcctcttccc gacccgccag atctgcatcc attccaccat   1380
ttgcatgatc tccgttgcgc acacgcagta atccgagtcc ctctagcact tcgagagctg   1440
gcccttgggg attcgcgtgg acgagagaag tgattttgcg acgctgaggc ggcgtcagag   1500
caatatcgaa atcgatcatc aattccacca cagacaacgc attttccag ctttcgcacg    1560 agaggagatt ccccaggagc gtggcgagga ggtctggagc agccacatca tttcgctctc   1620
tcatcgctcg gagcaattcc gttaccctgt ccaatctacc gcggtccaca tgacagagcg   1680
cagccacagc cgcggggtct ccaccttgat attcaagcgg catattatga tagacatcga   1740
aagctttctc gatttgtttc ggggccgata accagcagcc tcgcaacaac gaagcataaa   1800
aacctcggtc gggtttccag ccttgctcct cgaccaagcc tataatggtt tctgccgctg   1860
ccacatcggg cggatccaac ttcgcgcaat aaatgaacgt ggcccatcgg tatgtcgagt   1920
acgaggtgtt gggctttaag acgaggtcac ctaagaggtc tcgcgcacgg tctggctggc   1980
ccgcacgcag ggaggcaacg atcacaggaa tccctgagccg ttcctgggaa accagcatct   2040
cccgaggtag ggaggcggcc acgtccacca actcttgaaa gcggcaagct tgtttcaagc   2100
acttgaatag acggcggtag gtaaggggg agggtgcgga ggcctggcct tgcgcaagca    2160
tctcgtggta aagccccaaa gctttctccg ccatgccctc aggatcctct cgcaccaacc   2220
gatacgtggc gtgcagcgct tcgttgtaca tgatcgtatt gggagtccga ccaccagatt   2280
tgaaggtttc taggagcgcg agcgcctcgc gtcgactggc cacatccgcc ttgaccaggg   2340
cgtgcatgtg ggcgccgaac atgacgtcat tccaggtctc ttgcggatca ccagcgaggg   2400
ttctcaggcg tgtcaatagt ccgttcgcaa gagtacggtt cctaaggtcc gcagtcacgc   2460
tgatcaaact gttcaaaacg tacttgtcga cggggatacc ccgccgctcc atttcatcgt   2520
agagggccaa cgcccgatct ggctgccgcg ctctctcaaa gcccgagatg agcatgttga   2580
aagtggtgct gtccatcggt acttgacgca ttctcatctc ttggaaaacc gcctccgctt   2640
cttccaaacg ctccactcgc gaaaacgcgt gcagcacggc gttgtagtga agggtggagg   2700
```

```
gcttggcgtc gcccttgcct tggttcatga catgcaggac tcgtagcgcg tcccccggcc    2760
gcttcgcctg accgaaggcc ttgatcaggt tcatgtatct tgtactgcct tgcgcacatc    2820
cacgtgaccg ttgatcgcag cctggttcac gaggcctctc tgcgtggata cgaacaaatg    2880
aaacaagaca cgacttaact ccatgctgct tgcaagttat gagaggtcgg gtggtttgta    2940
cctgaacagc aaagtcagtc aatgcgcaca gggcttcgtt ggagagccca agtgcctcct    3000
cgtcttgctg ctgcattgta ataataatga acgctttctt cctttctatc tcccgaaaaa    3060
aaattgagaa accacatata ttgcgtgaat gcattggttt cggtatgaga aattgtgtag    3120
aatatcttat tcaaaattcg atagtaccca ttggattaga aagtagctct ttgttccgtg    3180 cgacttttg tgaccaagac ttacagatat tatagaatcg acaatctcat tgtgaatgaa    3240
agagatggat acaaaaacag caaacatttc atgagccctc caagttagtc gcattctcat    3300
aagttctcca gcagtacgcc aaagattgtt tcgtgcgact ttttatgacc aagacttaca    3360
gcgcccattt aacacatgct agtgagctgt ctctcaaaag gatatgacaa gcggtgcatt    3420
cctcttaatg cattgtgttc tttgcgtcgc agcatacaca ccttgccatc tacatcagtg    3480
cgcccaaggg attataggaa cgtatcggtt tcgaattaat ctatcgagag atgtgtgtgt    3540
tcttttgtag tgtcgacatg gtacaataga atattgtctt attgtaacga acatgtgatt    3600
tgactgttga gtgtgtcctg acgcagtgtg caatgttctt ggacaacaag aaggacgtcg    3660
ggtgacggac cgactcggac atgtgtcgac agattttccg gaccatggct ccacacgaat    3720
cgtcaaaatg caagcgattt atgagaagca aaatgacata atgatgacac caatccacgt    3780
ttagaccttt tcatctgttt atatagcgcg agttcgatcc tccaagggtc cctttttcgg    3840
ggtccatcgc cgatccgagt cacgtgtcaa accgtcgcct cggacttccc ccctgtgctc    3900
tcttcatggg agaacgaaga cagcgcgtgg aaacacgatc tgcgtcgtcc ccatgacaca    3960
ctaagcgcga gcgccctgcg gtccgtgaag actgcgagca cgcgccttag gagatgagag    4020
cctctcgaca tctcctgcat acatctgcag acgacaagag agcatcaggg gctaagggag    4080
gcatggaata gcgtcgacac atcgacagct cattccatat tctctctaag ttcccctgtg    4140
gagcgattgc ttcgatcagt gaagatcacc tggccctttc ctcgttgaaa gtgaggctca    4200
ggacggtcgg aaggtgttgt attggtacgc tttgacgtag ccttctcgtt gacactttga    4260
cttgcatacg acccttgtgg cgacggctgc atttgtgcgc tgttgctcca agaactatgc    4320
atcgaaggca cacgccctgg aagccccgac acctctgttt gagacactgc ttcaaatcac    4380
ttgagcagga ctcacaatga gagtacatcg tattgggttt g                       4421
```

<210> SEQ ID NO 6
<211> LENGTH: 770
<212> TYPE: DNA
<213> ORGANISM: Nannochloropsis gaditana
<220> FEATURE:
<221> NAME/KEY: misc_feature
<223> OTHER INFORMATION: NgARS2

<400> SEQUENCE: 6

```
aacaagtttt gattttgtg ttgtcgtatt tttacgcagg aaaatgtcag agccgataca     60
ttcgagctac ctggggttgt cttttttaaga gtcccagcat tgtgttcacc tacgatagtg    120
catggctgca agtaaattca ttttgcgata accacaaaac tagccaattt acgaatctgt    180
gaagaagttt ttcgcgttct acggtcctct tgtagtaacc catcgatgtt gcttcaagat    240
atgggcgctg gtcgatggaa aaaaccacag gactagttaa aatcatagat tccacgaaat    300
```

```
tattaaaata ttattttttca tgccctgcgg tccgtgaaga ctgcgagcac gcgccttagg      360
agatgagagc ctctcgacat ctcctgcata catctgcaga cgacaagaga gcatcagggg      420
ctaagggagg catggaatag cgtcgacaca tcgacagctc attccatatt ctctctaagt      480 tccccctgtgg agcgattgct tcgatcagtg aagatcacct ggcccttttcc tcgttgaaag    540 tgaggctcag gacggtcgga aggtattgta ttggtacgct ttgacgtagc cttctcgttg      600
acactttgac ttgcatacga cccttgtggc gacggctgca tttgtgcgct gttgctccaa     660
gaactatgca tcgaaggcac acgccctgga agccccgaca cctctgtttg agacactgct    720
tcaaatcact tgagcaggac tcacaatgag agtacatcgt attgggtttg               770
```

<210> SEQ ID NO 7
<211> LENGTH: 3777
<212> TYPE: DNA
<213> ORGANISM: Nannochloropsis gaditana
<220> FEATURE:
<221> NAME/KEY: misc_feature
<223> OTHER INFORMATION: NgARS3

<400> SEQUENCE: 7

```
agttttaccc tactgatgag ttgttgtcgc gacagtaata caacttagta cgagaggaac      60
cgttgtttca gataattggt aaatgcggtt ggctgaacag ccagtgccgc gaagctacca    120
tctgtgggat tatgactgaa cgcctctaag tcagaatcct tgctgaagat gcgacgatat    180
tcacctcttc tgatgctacg cgtatcgcga taggcttcgg cccagcatca tacgtcatca    240
tcatttcaat cattagaaga gataaatcct ctgtagacga ctttgatatg aacggggta    300 ttgtaagtgt gagagtaggc tttgtcctac gatccactga gattcagcct cttgttccgt    360
cgatttgttg ttgaaaacac tcctagtgag attgcggaaa ccacacaacg tggaccttcc    420
acgcaattca cgcccccccc acccccctagc acattgctct cccctcaaaa cgaaagggca    480
gagcgtgtga gagaaaaaac catctatcat cttcccacat gagtgtgaaa tggtgagaaa    540
acaatgcacc ccaccaacgt acatccgggt agctttaaat gaaaccctca gaactcgggt    600
catatgcctt ccaccagaca agtccctcaa cttcctcttt atacatccgg gtagctttcg    660
atggatcagc gtctgtatcc gggtagcttt tgcctaatct tcatttgaca tgaagtatct    720
ggacgataat atttacgggt tcttcgagga catcccgggca ttttaacaaa acatcgtgaa    780
acaagttttg attttgtgt tgtcgtatt ttacgcagga aaatgtcagc cgataccttc      840
gagctacctg gggttgtctt ttttgaagtc ccagcattgt gttcacctac tatagtgcac    900
tgctgcaagt gaattcattt tgcgatagcc acaaaactag ctaaactata caacttacga    960
atttatgaag ttgtttttttt cgttctacgg tcctcttgtt gtaacccatc gatgttgctt    1020
caagaacttc gatatgggct ctggtcgatg gaaaaaacca caggactagt taaaatcata   1080
gattccacga aattattgaa atattatttt tcatgctaca tacagaaatt cctgacagag   1140
aaaaaaacca cttttttacc actctcacat cagtgcgaga tggtatagag cgagctatcc   1200
ctcgaacata catccgggta gcttttactg aaaagcccta atttccccat gataggggga   1260
taaaaaggaa cataccatcg tcttcgtggg ttacacatgc gatcccaata catttgcgta   1320
tgctaccaaa atttaccttt ttttgtacac caaactcagt caataactgc tgtccgcgtg   1380
ttagagtttt ctgattattt catgtaactg aagtctgcga atatcgcacc tgttttttgga   1440 aatggataac tgcagtgctg taactctcaa tcctcccacc ttcacctgtt gtgcgctgca   1500
ttgacatccg tcacatcaac tatagcacag actctttcgt cataaaattt gcaactggtc   1560
```

```
caggaccagg aaacatactg ggcaggctgt ggtacaggtg ttgtatggag taagtcccaa    1620
tccgaagcca ccacaatcaa gcttcgattc ggcaagatcg gaatactgtg attttccata    1680
ctgtgacatg aagcttgtac aggcttcagt gttttttat cacaaaccca gcgaataaat     1740 atgtttttc tgccgaggaa tcgagtcaga tcgagatatt gccgtgggaa agcattgaag     1800
tactttctgg ccacagcctc ataaaacagg tggaaagtga tgtacgttat tgcaacgtta    1860
ttatttaata gtagcgaaca tgtgacttta ctgttgagtg tggcctgaca tgcatcggtt    1920
gtaccagctc agttcttccc tttcaactaa tgtgaaagaa gaccacaggc ggtcttgtac    1980
aaaccctagc ccttccactt accagcttgg actctttcga ctacaaagct gctgaagaag    2040
tcgccagagg cagttcaatc ggatttctta ccctgtagtt acctcacgtc gagcggtgct    2100
ctccaaagac caagacttag cgcccattta acacatgcta gtgagctgtc tctcaaaaag    2160
atatgacaag cggtgccaag acttacagat attatagaat cgacaatctc attgtgaatg    2220
aaagagatgg atacaaaaac agcaaacatt tcatgagccc tccaagttag tcgcattctc    2280
ataagttctc cagcagtacg ccaaagatgg tttcgtgcga cttttatga ccaagactta     2340 cagcgcccat ttaacacatg ctagtgagct gtctctcaaa aagatatgac aagcggtgca    2400
ttcctcttaa tgcattgtgt tctttgcgtc gcagcataca caccttgcca tctccatcag    2460
tgcgcccaag ggattatagg aacgtatcgg tttcgaatta atctatcgag agatgtgtgt    2520
gttcttttgt agtgtcgaca tggtacaata gaatattgtc ttattgtaac gaacatgtga    2580
tttgactgtt gagtgtgtcc tgacgcagtg tgcaatgttc ttggacaaca agaaggacgt    2640
cgggtgacgg acggactcgg acatgtgtcg acagattttc cggaccatgg ctccacacga    2700
atcgtcagaa tgcaagcgat ttatgagaag caaaatgata taatgatgac accaatccac    2760
gtttagacct tttcatatgg ctatatggcg cgagttcgat cctccaaggg tccctttttc    2820
ggggtccatc gccgatccga gtcacgtgtc aaaccgtcgc ctcggacttc ccccctgtgc    2880
tctcttcatg ggagaacgaa gacagcgcgt ggaaacacga tctgcgtcgt ccccggtgac    2940
acactaagag cgagcgccct gcggtccgtg aagactgcga gcacgcgcct taggagatga    3000
gagcctctcg acatctcctg catacatctg cagacgacaa gagagcatca ggggctaagg    3060
gaggcatgga atagcgtcga ctgatcaaca gcgcattcca tattctccct aagttcccct    3120
gtggagcgat tgcttcgatc agtgaagatc acctggccct ttcctcgttg aaagtgaggc    3180
tcaggacggt cggaaggtgt tgtattggta cgctttgacg tagccttctc gttgacactt    3240
tgacttgcat acgaccccttg tggcgacggc tgcatttgcg cactgttgcc ccaagaacta    3300
tgcatcgaag gcacacgccc tggaagcccc gacacctctg tttgagacac tgcttcaaat    3360
cacttgagca ggactcacaa tgagagtaca tcatattggg tttgcttcgt atgagcgttg    3420
tgcctggtga agttgcagag aggcctcgga agaaggtgct ctaacactgt cgcgaaagga    3480
cgactccgtg agatcacggt gttgcttcgc gcccaccttg ttaacaatgt tttctcctga    3540
aaatatgtta actagttaca aattaaattg ctgtcctatc agtggcgata ggtgttctcg    3600
gacacggtcg ccctggttga cctcagctgt cgcatcgaga gtctcctctc ctcggaagag    3660
aagagggacg ctggagacgg cagcattcga cgatagcaat ctggttgatt ctgccagtag    3720
tcatacgctt gtctcaaaga ttaagccatg cacgtctgag aataaagagt tttctct       3777
```

<210> SEQ ID NO 8
<211> LENGTH: 3093
<212> TYPE: DNA

<213> ORGANISM: Nannochloropsis gaditana
<220> FEATURE:
<221> NAME/KEY: misc_feature
<223> OTHER INFORMATION: NgARS4

<400> SEQUENCE: 8

```
agttttaccc tactgatgag ttgttgtcgc gacagtaata caacttagta cgagaggaac     60
cgttgtttca gataattggt aaatgcggtt ggctgaacag ccagtgccgc gaagctacca    120
tctgtgggat tatgactgaa cgcctctaag tcagaatcct tgctgaagat gcgacgatat    180
tcacctcttc tgatgctacg cgtatcgcga taggcttcgg cccagcatca tacgtcatca    240
tcatttcaat cattagaaga gataaatcct ctgtagacga ctttgatatg aacgggta     300
ttgtaagtgt gagagtaggc tttgtcctac gatccactga gattcagcct cttgttccgt    360
cgatttgttg ttgaaaacac tcctagtgag attgcggaaa ccacacaacg tggaccttcc    420
acgcaattca cgccccccc  acccctagc acattgctct cccctcaaaa cgaaagggca    480
gagcgtgtga gagaaaaaaa ccttttacca tctttcccac atgagtgtga agtggtaaga    540
aaacaatcat cccaccaacg tacatccggg tagctttaaa tgaaaccctc agaactcggg    600
tcatatgcct tccaccagac aagtccttta acttccccgt ctttatacat ccgggtaact    660
ttcgatggat cagcgtctgt atccgggtag cttttgccta atcttcattt gacatgaagt    720
atctggacga taatatttac gggttcttcg aggacatccg gcattttaa  caaaacatcg    780
tgaaacaagt ttgattttg  tgttgtcgta ttttttacgca ggaaaatgtc agagccgata    840
cattcgagct acctggggtt gtcttttag  agtcccagca ttgtgttcac ctacgatagt    900
gcatggctgc aagtaaattc attttgcgat aactacaaaa ctagccaatt tacgaatctg    960
tgaagaagtt tttcgcgttc tacggtcctc ttgtagtaac ccatcgatgt tgcttcaaga   1020
tatgggcgct ggtcgatgga aaaaaccaca ggactagtta aaatcataga ttccacgaaa   1080
ttattaaaat attattttc  atgctccata cagaaattgc cgataggaaa accactttt    1140
ttaccactct cacattagtg cgagatggtg aagatagaac tttccctcga acatacgtcc   1200
gggtagcttt tactgaaaag ccccgagaac ccgtactgta cgagtgtgtc gcgccttcca   1260
cgccgacatc atcttcgtct tggctgcctt tgtacatccg ggttatttct gagacccttc   1320
tattagtctt gcgtatacga tgcaaggtta acccttgaca tgtcgagtgg acatgtcctc   1380
cacataaacc acagactcga tgtcgactta cgtcgatgac atgacatgtc atcggttgtc   1440
tttcatgtcg acacttctcg acatctgcga aaagccctga gaacttggat gagtacccca   1500
ccatggtttt ttttgggaaa ttcagtatac atccggtcga tggaaacaac cacaggacta   1560
gtacaaatta tagaaaacac ggaattattg aggtatgaat tttcatgctg catacaaaaa   1620
aaatccctag ttcgctgttt tttcggaagg tgccatcata accgagagag gcccgatgac   1680
ggtattgaag acagcacatt cgtgacatgg aatgtcgtgc catgtctttt taaccccaag   1740
caattaaaat ttctggcggt taatcgatgt cactgtgcat catccctctc atgtccaatg   1800
tcaagcgtat aaccataagc gctcttgcca taagactaaa atgctttcac atgaaataat   1860
caaaaatatg gaggcatgaa taagatcttt tgcaaaggaa ttctactcac ttttcgatgg   1920
aatgtgtgtt tctttcatgc ttcaaaacta atgtagcatt cacatcgctg ttctataggc   1980
ccttttttcta ataccatgc  acgagcgagc gtcatgactg agcaaaccac tgtagtacct   2040
gctcataatt gggcactgtc ctcaaatctt tttttaaccg ctgagatgga aaccggcttt   2100
gaaatggccc gccgcgctat tttcatcaaa tcctcggcct tgacctcgtc aatcttgcga   2160
```

```
cacaaggcct caggagcctc gcgatgcccg tacgtgatca tctgccggcc aatgtctcga    2220
agagaatgat tcgagatcca agctgtgtca agacattgca cttcagcatg ttcctcgccc    2280
gggacaattc tacaggatca accggcgtca aggcgagttt gcagatttgc gtacagaatt    2340
cgtgcatgag ctgaccggca agagcggcct cgcaggcacc tgcaatcccc aggaccccg    2400 tctcattggt tcacaaaggc ctcggctccc tctacccagt agtaccgatt caaaagttcc    2460
ctatatagcc gtgagtacat gcctttccca ggcccgcctg cggagaaaga gtccccacca    2520
cccaggagga tttgcatcac gcacatggct accaggtcct tgtcatgcca tcccgccacc    2580
tcgaagccca cggccacgcg agtaaatggg tctatgctgt caggctgctc aatccgcttc    2640 tcgccccct gataaagggc ccgtgcgcgc ttgtgagcgc cttctcctgc tggcaagcgc    2700
ccgaaatgct ttttcgcaag gtcaacaaat gcttcgtgct ccacacccgc gcggccagc    2760 accatgctcc tcgccgtaaa atgccgcgtc tggaatgcct tgagtccctc ggcgctgagc    2820
ctaaggagat attggagcaa cactgtgagc tgtaattctg tcgtgtatcg ccaccccaca    2880
ctcagcttct ccccaatccc cacgtccgcc aacttacccc gacagagtct caggcgtcac    2940
gaagtgcggc ctacccagcg cctgtccagg gtacgccgcc tcttgtatgg cctccttgac    3000
caggagctcg ggcgctatgc tgtccaaatg aaggcctagg atagtcttgg attcttcgat    3060
atcctgcgcg tctgagaata aagagttttc tct                                3093

<210> SEQ ID NO 9
<211> LENGTH: 3722
<212> TYPE: DNA
<213> ORGANISM: Nannochloropsis gaditana
<220> FEATURE:
<221> NAME/KEY: misc_feature
<223> OTHER INFORMATION: NgARS5

<400> SEQUENCE: 9
gcgacgatat tcacctcttc tgatgctacg cgtatcgcga taggcttcgg cccagcatca      60
tacgtcatca tcatttcaat cattagaaga gataaatcct ctgtagacga ctttgatatg     120
gaacggggta ttgtaagtgt gagagtaggc tttgtcctac gatccactga gattcagcct     180
cttgttccgt cgatttgttg ttgaaaacac tcctagtgag attgcggaaa ccacacaacg     240
tggaccttcc acgcaattca cgccccccc accccctagc acattgctct cccctcaaaa     300
cgaaagggca gagcgtgtga gagaaaaaaa ccttttacca tctttcccac atgagtgtga     360
agtggtaaga aaacaatcat cccaccaacg tacatccggg tagctttaaa tgaaaccctc     420
agaactcggg tcatatgcct tccaccagac aagtccttta acttcccgt ctttatacat      480 ccgggtaact ttcgatggat cagcgtctgt atccgggtag ctttttgccta atcttcattt     540 gacatgaagt atctggacga taatatttac gggttcttcg aggacatccg gcatttta      600 caaacatcg tgaaacaagt ttgattttg tgttgtcgta tttttacgca ggaaaatgtc       660
agagccgata cattcgagct acctgggggtt gtctttttaa gagtcccagc attgtgttca    720
cctacgatag tgcatggctg caagtaaatt cattttgcga taaccacaaa actagccaat     780
ttacgaatct gtgaagaagt ttttcgcgtt ctacggtcct cttgtagtaa cccatcgatg     840
ttgcttcaag atatgggcgc tggtcgatgg aaaaaaccac aggactagtt aaaatcatag     900
attccacgaa attattaaaa tattatttt catgctccat acagaaattg ccgataggaa      960
aaaccacttt tttaccactc tcacattagt gcgagatggt gaagatagaa ctttccctcg    1020
aacatacgtc cgggtagctt ttactgaaaa gccctgagaa cccgtactgt acgagtgtgt    1080
```

```
cgcgccttcc acgccgacgt catcttcgtc ttggctgcct ttgtacatcc gggttatttc    1140 tgagacccett ctattagtct tgcgtatacg atgcaaggtt aacacttcac atgtcgagtg    1200
gacatgtcct ccacataaac cacagactcg atgtcgactt acgtcgatga catgacatgt    1260
catcggttgt cttcatgtc gacacttctc gacatctgcg aaaagccctg agaacttgga    1320
tgagtacccc accatggatt tttttgggaa attcagcata catccggtcg atggaaacaa    1380
ccacaggact agtacaaatt atagaataca cggaattatt gaggtgtgaa ttttcatcct    1440
gcatacaaaa aaattcccta gttcgctgtt ttttcggaag ttgccatcat aaccgagaga    1500
ggcctgatga cggtattgaa gacagcacat tcgtgacatg gaatgtcgtg ccatgtcttt    1560
ttaaccccaa gcagttaaaa tttctggcgg ttaatcgatg tcactgtgca tcatccctct    1620
catgtccaat gtcaagcgta taaccataag cgctcttgcc ataagacagc attttattca    1680
catgaaataa tcaaaaacat ggaggcatga ataagatctt ttgcaaagga attcgactca    1740
cttttcgatg ggatgtgttt tcttcatgc ttcaaaacta atgtagtatt cacatcgctg    1800
ttctataggc cctttccta ataccatgc acgagcgagc gtcatgactg agcaaaccac    1860
tgtagtacct gctcataatt gggcactgtc ctcaaatctt ttccaaccgc tgagatggaa    1920
accggctttg aaatggcccg ccgcgctatt ttcatcaaat cctcggcctt gacctcgtca    1980
atcttgcgac acaaggcctc aggagcctcg cgatgcccgt acgtgatcat ctgccggcca    2040
atgtcttcga agagaatgat tcgagattca agctgtgtca agacattgca cttcagcatg    2100
ttcctcgccc gggacaattc tacaggatca accggcgtca aggcgagttt gcagatttgc    2160
gcacagaatt cgtgcatgag ctgaccggca cgagcggcct cgcaggcacc tgcaatcccc    2220 aggaccccg tctcattatg aaggttcaca aaggcctcgg ctccctctac ccagtagtac    2280
cgattcaaaa gttccctata taccgtgag tacatgcctt tcccaggccc gcctgcggag    2340
aaagagtccc caccacccag gaggatttgc atcacgcaca tggctaccag gtccttgtca    2400
tgccatcccg ccacctcgaa gcccacggcc acgcgagtaa atgggtctat gctgtcaggc    2460
tgctcaatcc gcttctcgcc cccctgataa agggcccgtg cgcgcttgtg agcgccttct    2520
cctgccggca agcgcccgaa atgcttttc gcaaggtcaa caaatgcttc gtgctccaca    2580
cccgccgcgg ccagcaccat gctcctcgcc gtaaaatgcc gcgtctggaa tgccttgagt    2640
ccctcggcgc tgagcctaag gagatattgg agcaacactg tgagctgtac ttctgtcgtg    2700
tatcgccacc ccacactcag cttctcccca atccccacgt ccgccaactt acctcggcag    2760
agtctcaggc gtcacgaagt gcggcctacc cagcgcctgt ccagggtacg ccgcctcttg    2820
tatggcctcc tgaccaggag ctcgggcgct atgctgtcca aatgaaggcc taggatagtc    2880
ttggattctt cgatatcctg cgcgtctgag ggggtaccaa ggaaagccag aaggatcaaa    2940
aacaggaaac gaaatgagtg ctttctttat gcagcgtagg tttccttgaa catgaattct    3000
cgcccacgcc cgtcgtaact ccaatgccct ctacttccgt gtcgtgaccc acctatttc    3060 ggattgagaa ctgcgtcccc gaagatctca agagcctcgg gaagggagtt ccgcaacacg    3120
tcgatggata gaagcatctg ttcacgcgag gagttggccg tgggaatcgc acccaggtcg    3180
tccaaagcgc tgactactc cttgtggctc ctcttctccg tgccccggaa agccgtggcc    3240
tcgaacaggt ggcacacgcc gtcctcccgc cctgccaatt cgtcgcggct gcctgcatct    3300
accaccacac cgaaagtgca gagctgtatc gcaagcggga atgtttcacc gaattaaaca    3360
aggaattgac tcatcgatat cattgccacc acgacatgtg tgaggatcaa gtgtgccaga    3420
ccggacgcca tgggcaccgt tttatatttt ttctcaagaa cgataaacat gtcaggatat    3480
```

```
ttcaaagtaa ctcaccgcgc cgtatgtctc ttgcgtggca actcgtaaac cgttgtccag    3540
cgtggtgatt tttgtgacgg gtgcttgcaa ttcgctcaag ggcttcgtgg gaggcacgtc    3600
tatacttgaa tgaattacag tgcgtgagga gaggcttgct gtcggacgca gcgagaaatt    3660
ggacctacct gacgggacag tatccatgcc aaaacgagca acccggtatt gtggtgaatc    3720
at                                                                   3722
```

<210> SEQ ID NO 10
<211> LENGTH: 2543
<212> TYPE: DNA
<213> ORGANISM: Nannochloropsis gaditana
<220> FEATURE:
<221> NAME/KEY: misc_feature
<223> OTHER INFORMATION: NgARS7

<400> SEQUENCE: 10

```
agttttaccc tactgatgag ttgttgtcgc gacagtaata caacttagta cgagaggaac      60
cgttgtttca gataattggt aaatgcggtt ggctgaacag ccagtgccgc gaagctacca     120
tctgtgggat tatgactgaa cgcctctaag tcagaatcct tgctgaagat gcgacgatat     180
tcacctcttc tgatgctacg cgtatcgcga taggcttcgg cccagcatca tacgtcatca     240
tcatttcaat cattagaaga gataaatcct ctgtagacga cttttgatatg aacggggta     300 ttgtaagtgt gagagtaggc tttgtcctac gatccactga gattcagcct cttgttccgt     360
cgatttgttg ttgaaaacac tcctagtgag attgcggaaa ccacacaacg tggaccttcc     420
acgcaattca cgcccccccc acccctagc acattgctct cccctcaaaa cgaaagggca     480
gagcgtgtga gagaaaaaaa ccttttacca tctttcccac atgagtgtga agtggtaaga     540
aaacaatcat cccaccaacg tacatccggg tagctttaaa tgaaaccctc agaactcggg     600
tcatatgcct tccaccagac aagtcccttta acttccccgt ctttatacat ccgggtaact     660
ttcgatggat cagcgtctgt atccgggtag cttttgccta atcttcattt gacatgaagt     720
atctggacga taatatttac gggttcttcg aggacatccg ggcattttaa caaaacatcg     780
tgaaacaagt ttgattttttg tgttgtcgta ttttacgca ggaaaatgtc agagccgata     840
cattcgagct acctggggtt gtcttttttaa gagtcccagc attgtgttca cctacgatag     900
tgcatggctg caagtaaatt cattttgcga taaccacaaa actagccaat ttacgaatct     960
gtgaagaagt ttttcgcgtt ctacggtcct cttgtagtaa cccatcgatg ttgcttcaag    1020
atatgggcgc tggtcgatgg aaaaaaccac aggactagtt aaaatcatag attccacgaa    1080
attattaaaa tattattttt catgctccat acagaaattg ccgataggaa aaaccacttt    1140
tttaccactc tcacattagt gcgagatggt gaagatagaa ctttccctcg aacatacgtc    1200
cgggtagctt ttactgaaaa gccccgagaa cccgtactgt acgagtgtgt cgcgccttcc    1260
acgccgacat catcttcgtc ttggctgcct ttgtacatcc gggttatttc tgagacccctt    1320 ctattagtct tgcgtatacg atgcaaggtt aacccttgac atgtcgagtg acatgtcct     1380 ccacataaac cacagactcg atgtcgactt acgtcgatga catgacatgt catcggttgt    1440
ctttcatgtc gacacttctc gacatctgcg aaaagccctg agaacttgga tgagtacccc    1500
accatggttt ttttggga attcagtata catccggtcg atggaaacaa ccacaggact    1560
agtacaaatt atagaaaaca cggaattatt gaggtatgaa ttttcatgct gcatacaaaa    1620
aaaatcccta gttcgctgtt ttttcggaag gtgccatcat aaccgagaga ggcccgatga    1680
cggtattgaa gacagcacat tcgtgacatg gaatgtcgtg ccatgtcttt ttaaccccaa    1740
```

```
gcaattaaaa tttctggcgg ttaatcgatg tcactgtgca tcatccctct catgtccaat    1800
gtcaagcgta taaccataag cgctcttgcc ataagactaa aatgctttca catgaaataa    1860
tcaaaaatat ggaggcatga ataagatctt ttgcaaagga attctactca cttttcgatg    1920
gaatgtgtgt ttctttcatg cttcaaaact aatgtagcat tcacatcgct gttctatagg    1980
cccttttcct aatacccatg cacgagcgag cgtcatgact gagcaaacca ctgtagtacc    2040
tgctcataat tgggcactgt cctcaaatct ttttttaacc gctgagatgg aaaccggctt    2100
tgaaatggcc cgccgcgcta ttttcatcaa atcctcggcc ttgacctcgt caatcttgcg    2160
acacaaggcc tcaggagcct cgcgatgccc gtacgtgatc atctgccggc caatgtcttc    2220
gaagagaatg attcgagatc caagctgtgt caagacattg cacttcagca tgttcctcgc    2280
ccgggacaat tctacaggat caaccggcgt caaggcgagt ttgcagattt gcgtacagaa    2340
ttcgtgcatg agctgaccgg caagagcggc ctcgcaggca cctgcaatcc ccaggacccc    2400
cgtctcattg gttcacaaag gcctcggctc cctctaccca gtagtaccga ttcaaaagtt    2460
ccctatatag ccgtgagtac atgcctttcc caggcccgcc tgcggagaaa gagtccccac    2520
cacccaggag gatttgcatc acg                                            2543

<210> SEQ ID NO 11
<211> LENGTH: 2474
<212> TYPE: DNA
<213> ORGANISM: Nannochloropsis gaditana
<220> FEATURE:
<221> NAME/KEY: misc_feature
<223> OTHER INFORMATION: NgARS8

<400> SEQUENCE: 11
caaacccaat acgatgtact cccaattgca tcctggatgc tggtccagcg gtctccgacg      60
tcgaatgaat agttgagaca aaattatcgt aatacaaaaa ggacgtcaac tgctctccag     120
taatctgacg ttgcatggcc gcgcgtgccc ccatgccagc acgcaagctt gcagggccgt     180
ttgcaaatct cgaacaagag agcaataaac accgtggccc agatcgtggc tttctagcat     240
gttcgagaat ctcgaacaag agagcaataa acaccgtggc ccagatcgtg gctctctagc     300
atgttcgagg tattgtgaag ctcggcaccg taacgagcaa gctcttggcc ctccccccg      360 tgcgagcgga cgacacggac taatgacaag acctggccag ccacagcatt tgccttggcg     420
agtgactcct gactgcgtcg acccatccgg cggatgaact caccatggag ggtagtcagg     480
gcaatcacga ggaagatacc cgcgattgtc acgaaagcga ggccacgatg aaaacgaaac     540
aagaaaatgc tcctaccgat cagctagatg actgtcgcag caacacgtcc gcgtgcgacg     600
aaaccacgct ggaaaattca gaacaatcta ttcaaagtcg attcgtcact tcatctgaat     660
ctacgctttc cacgaaagcc acattttgct taagcaacgg ttccaaaagc taggactgag     720
cacaaagtgc gacgcctgta ccaatgaaga atggacgcga acgaaagtca aggcgggaaa     780
aaccaggccc aatacgacaa ctgcatagac cgcccgttga aattcctgca tcttaccacc     840
cactacggcg cattaggcct aggaagaaaa atgcgggacg gctacatcgc agatggcggc     900
tctgaccaat gcgaatgtgc tgaagcaaaa atatttgcgt tcgttcaagc tcgataaaat     960
tgaagctatc ccttttggtc tgactctccc tgcctatgct gtgaccccct tccgcggctga   1020 accagtactc ccgaccccga agcactcaat ggctcgaagg cggaagaaaa ttccatggac    1080
accagaaagt cgcggtctcg cgtggaatca cctccattc ccacgatacg agcaaagcca    1140
gagaatgtat ggtcattatc gtggttattt ttgaggagat cgagacgatg ccgtcggccg    1200
```

```
tactgcccgt gatgcggctt cccattggga aggcctcgag gcgatcattt gtacccatct    1260
tatagaatcg acaacctcat tgtgaatgaa agagatggat acaaaaacag caaacatttc    1320
atgagccctc caagtgaatc gcattctcat aagttctcca gcagtacgcc aagattgttc    1380
cgtgcgactt tttgtgacca agacttacag cgcccattta acacatgcta gtgagctgtc    1440
tctcaaaaag acatgataag cggcgcattc ctcttaatgc attgtgttct ttgcgtcgca    1500
gcatatataa acacctagcc atctacatca gtgcgcccaa gggattatag gaacgtatcg    1560
gtttcgaatt aatctatcga gagatgtgcg tgttcttttg tagtgtcgac atggtacaat    1620
agaatattgt cttattgtaa cgaacatgtg atttgactgt tgagtgtgtc ctgacgcagt    1680
gtgcaatgtt cttggacaac aagaaggacg tcgggtgacg gaccgactcg gacatgtgtc    1740
gacagatttt ccggaccatg gctccacacg aatcgtcaaa atgcaagcga tttatgagaa    1800
gcaaaatgac ataatgatga caccaatcca cgtttagacc ttttcatctg tttatatagc    1860
gcgagttcga tcctccaagg gtcccttttt cggggtccat cgccgatccg agtcacgtgt    1920
caaaccgtcg cctcggactt cccccctgtg ctctcttcat gggagaacga agacagcgcg    1980
tggaaacacg atctgcgtcg tccccatgac acactaagcg cgagcgccct gcggtccgtg    2040
aagactgcga gcacgcgcct taggagatga gagcctctcg acatctcctg catacatctg    2100
cagacgacaa gagagcatca ggggctaagg gaggcatgga atagcgtcga cacatcgaca    2160
gctcattcca tattctctct aagttcccct gtggagcgat tgcttcgatc agtgaagatc    2220
acctggccct ttcctcgttg aaagtgaggc tcaggacggt cggaaggtgt tgtattggta    2280
cgctttgacg tagccttctc gttgacactt tgacttgcat acgacccttg tggcgacggc    2340
tgcatttgtg cgctgttgct ccaagaacta tgcatcgaag gcacacgccc tggaagcccc    2400
gacacctctg tttgagacac tgcttcaaat cacttgagca ggactcacaa tgagagtaca    2460
tcgtattggg tttg                                                      2474
```

<210> SEQ ID NO 12
<211> LENGTH: 1183
<212> TYPE: DNA
<213> ORGANISM: Nannochloropsis gaditana
<220> FEATURE:
<221> NAME/KEY: misc_feature
<223> OTHER INFORMATION: NgARS-Sm

<400> SEQUENCE: 12

```
agaactcggg tcatatgcct tccacttacc agcttggact ctttcgacta caaagctgct     60
gaagaagtcg ccagaggcag ttcaatcgga tttcttaccc tgtagttacc tcacgtcgag    120
cggtgctctc caaagaccaa gacttagcgc ccatttaaca catgctagtg agctgtctct    180 caaaagata tgacaagcgg tgccaagact tacagatatt atagaatcga caatctcatt    240
gtgaatgaaa gagatggata caaaaacagc aaacatttca tgagccctcc aagttagtcg    300
cattctcata agttctccag cagtacgcca agatggtttt cgtgcgactt tttatgacca    360
agacttacag cgcccattta acacatgcta gtgagctgtc tctcaaaaag atatgacaag    420
cggtgcattc ctcttaatgc attgtgttct ttgcgtcgca gcatacacac cttgccatct    480
ccatcagtgc gcccaaggga ttataggaac gtatcggttt cgaattaatc tatcgagaga    540
tgtgtgtgtt cttttgtagt gtcgacatgg tacaatagaa tattgtctta ttgtaacgaa    600
catgtgattt gactgttgag tgtgtcctga cgcagtgtgc aatgttcttg gacaacaaga    660
aggacgtcgg gtgacggacg gactcggaca tgtgtcgaca gattttccgg accatggctc    720
```

```
cacacgaatc gtcagaatgc aagcgattta tgagaagcaa aatgatataa tgatgacacc    780
aatccacgtt tagacctttt catatggcta tatggcgcga gttcgatcct ccaagggtcc    840 cttttcggg gtccatcgcc gatccgagtc acgtgtcaaa ccgtcgcctc ggacttcccc     900
cctgtgctct cttcatggga gaacgaagac agcgcgtgga aacacgatct gcgtcgtccc    960
cggtgacaca ctaagagcga gcgccctgcg gtccgtgaag actgcgagca cgcgccttag   1020
gagatgagag cctctcgaca tctcctgcat acatctgcag acgacaagag agcatcaggg   1080
gctaagggag gcatggaata gcgtcgactg atcaacagcg cattccatat tctccctaag   1140
ttcccctgtg gagcgattgc ttcgatcagt gaagatcacc tgg                      1183
```

<210> SEQ ID NO 13
<211> LENGTH: 323
<212> TYPE: DNA
<213> ORGANISM: Nannochloropsis gaditana
<220> FEATURE:
<221> NAME/KEY: misc_feature
<223> OTHER INFORMATION: Homology sequence 1 from NgARS2

<400> SEQUENCE: 13

```
aacaagtttt gattttgtg ttgtcgtatt tttacgcagg aaaatgtcag agccgataca     60
ttcgagctac ctggggttgt cttttaaga gtcccagcat tgtgttcacc tacgatagtg    120
catggctgca agtaaattca ttttgcgata accacaaaac tagccaattt acgaatctgt   180
gaagaagttt ttcgcgttct acggtcctct tgtagtaacc catcgatgtt gcttcaagat   240
atgggcgctg gtcgatggaa aaaccacag gactagttaa aatcatagat tccacgaaat    300
tattaaaata ttatttttca tgc                                            323
```

<210> SEQ ID NO 14
<211> LENGTH: 448
<212> TYPE: DNA
<213> ORGANISM: Nannochloropsis sp.
<220> FEATURE:
<221> NAME/KEY: misc_feature
<223> OTHER INFORMATION: Homology sequence 2 from NgARS2

<400> SEQUENCE: 14

```
ccctgcggtc cgtgaagact gcgagcacgc gccttaggag atgagagcct ctcgacatct     60
cctgcataca tctgcagacg acaagagagc atcaggggct aagggaggca tggaatagcg   120
tcgacacatc gacagctcat tccatattct ctctaagttc ccctgtggag cgattgcttc   180
gatcagtgaa gatcacctgg cccttttcctc gttgaaagtg aggctcagga cggtcggaag   240
gtattgtatt ggtacgcttt gacgtagcct tctcgttgac actttgactt gcatacgacc   300
cttgtggcga cggctgcatt tgtgcgctgt tgctccaaga actatgcatc gaaggcacac   360
gccctggaag ccccgacacc tctgtttgag acactgcttc aaatcacttg agcaggactc   420
acaatgagag tacatcgtat tgggtttg                                       448
```

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15

```
gttgctgtga tcctcctcca c                                               21
```

<210> SEQ ID NO 16
<211> LENGTH: 24
<212> TYPE: DNA
<213> ORGANISM: Artificial Sequence
<220> FEATURE:
<223> OTHER INFORMATION: Primer

<400> SEQUENCE: 16
catgaccaac aagatgaaga gcac                                          24

<210> SEQ ID NO 17
<211> LENGTH: 1029
<212> TYPE: DNA
<213> ORGANISM: Artificial Sequence
<220> FEATURE:
<223> OTHER INFORMATION: Synthetic nucleic acid sequence
<220> FEATURE:
<223> OTHER INFORMATION: Hygromycin Resistance Gene

<400> SEQUENCE: 17
atggggaaga aaccggaact gaccgctacg tccgtggaga aattccttat tgagaagttc      60
gactctgtct ccgacttgat gcaactgagc gagggagagg agagtagggc gttctcgttt     120
gacgtagggg gtcggggata cgtgttgagg gttaatagtt gtgcggacgg gttctacaag     180
gatcggtatg tctaccgtca tttcgcctcc gccgctctcc ccataccaga ggtactggac     240
attggggagt ttagcgaatc tctcacgtac tgcatctcgc gccgagccca gggagtgacg     300
ttgcaagatc tgcccgaaac tgaattgcct gccgttttgc aacccgtggc cgaggccatg     360
gacgcgatcg ctgccgcaga tctgtctcag acgtccggct ttggaccttt tgggccccag     420
ggcatcgggc agtacacgac ctggcgagac ttcatctgcg ccattgccga tcctcacgtc     480
tatcattggc agacagtcat ggatgacacc gtgtctgcat ccgtggccca agcactggac     540
gaactcatgt tgtgggccga ggattgccct gaggtcaggc acctggtgca cgcggatttc     600
ggcagcaata acgtacttac agacaatggt cggattactg ctgtcatcga ctggtccgaa     660
gcgatgtttg gtgatagcca atacgaagtg gcgaacatat tcttctggcg tccctggttg     720
gcgtgcatgg agcagcagac acgctacttt gaacggaggc acccgagct  ggccggctcc    780 ccacgactcc gcgcctatat gttgcgtatc ggactcgatc agctttacca gtctctcgtc     840
gacggcaact cgacgacgc cgcgtgggcg cagggccgct cgacgcgat agtccgcagc      900 ggggctggga cggtgggtcg gacccaaatc gcacgccggt cggctgcggt gtggacagac     960
ggctgtgttg aggtgcttgc ggactcgggc aaccgtaggc cgagcacccg accgcgtgca    1020
aaggagtga                                                           1029

<210> SEQ ID NO 18
<211> LENGTH: 1002
<212> TYPE: DNA
<213> ORGANISM: Nannochloropsis gaditana
<220> FEATURE:
<221> NAME/KEY: misc_feature
<223> OTHER INFORMATION: TCTP Promoter

<400> SEQUENCE: 18
cgtgcaggtg tacagattga aggaaacaat ggagatatct ttggcagttg aaaaccgtgt      60
tcgaatcatg cttttctact ctccaactga gacgaaattt atagcgccat gtcgcttctg     120
actaccaggc ttaggaaggc ctcatcacaa gctggatcgg ttcgaattaa gcaggcactg     180
aagccaagct tgcaagacag ccacctttta attccctcaa aacactttct caattcagcc     240

```
cggtaaatat gccgattcac agcggccaag atagagggga ggttagcaag aatgttgcga    300
tccctcccca gtcgttgcct cgcacacaac ctaggccttc acctttccat ggaaaattga    360
gaagtgaata ttggttttct tacggcatat cagatgaaat catgacccct aaacatgaag    420
agctgcaggc aaaacacctg ctctggacga gcacgatgaa atctcgagaa cccgccgtac    480
ttcagttgat cccgcatgat gacggccgcc attgaaataa gccacctcac tttattctag    540
caccgatttc caccgttgtg agggccgaac gaggacaatt tcgtgcgaaa caagcacgaa    600
cacgcacacg attagtagta cagacgagca gatcgatggc atgcggcacg tctcgcgtt     660 ctcggcgacc aggacaacgg agcagaggga ggcctgccga gttccgaggg cattttagt     720 ccaaaattgt gttgacacgt gaacaagtgg cttgaaaaga ggaaggaaat gcctgggttt    780
cccttcgaga gcgggaactc gcttgtgcgt catcctagct acccatggtc cctttgtggg    840
ggaggctgtt tcgtcctacc gaatgtgtgg cgctccatgc atcttctgcc tcccaaacca    900
ccaacatgag cacgcgaagg aaggagaaaa aagtggccgc aacgttctct tctcatatt     960 attgtctcat cacaaacata ggtacataat acaacaatca tg                       1002

<210> SEQ ID NO 19
<211> LENGTH: 399
<212> TYPE: DNA
<213> ORGANISM: Artificial Sequence
<220> FEATURE:
<223> OTHER INFORMATION: Synthetic gene from Streptoalloteichus
      hindustanus codon optimized for N. gaditana
<220> FEATURE:
<223> OTHER INFORMATION: Blast 150- blastocidin S-deaminase blastocidin
      resistance gene

<400> SEQUENCE: 19
atggccaagc ctttgtccca agaggaatcc acgctgatcg aacgtgcaac tgcgaccatc     60
aacagcatac ctattagcga ggactactcg gtggccagtg cagccctctc gtccgacggt    120
cggatcttta ccggcgtgaa tgtatatcat ttcaccggag gccatgcgc ggagctcgtg     180 gtcctcggaa cggccgctgc ggctgctgcc ggaaatctga cgtgcatagt ggccatcggg    240
aacgaaaacc gcggcattct gtctccgtgc gggcgatgtc ggcaggtgct gcttgacttg    300 caccccgggga tcaaggcaat tgtcaaagat tccgatgggc agcccacagc ggttggcatc    360
agggagttgc ttccctctgg ctacgtctgg gagggttga                            399

<210> SEQ ID NO 20
<211> LENGTH: 485
<212> TYPE: DNA
<213> ORGANISM: Nannochloropsis gaditana
<220> FEATURE:
<221> NAME/KEY: misc_feature
<223> OTHER INFORMATION: Alpha tubulin terminator

<400> SEQUENCE: 20
agatcctcac tctgtcgcgc tgttggcgcc actactttgg gggtacgagt ttaggctgcc      60
ttggctggga taaagaatga taagtttaca taatttgtat tggaaatcca tcgagttttg    120
gattcagttg acgtctcctg cgttactatg tcttcattct ctccagtatc aatgcctatg    180
gttcgtcgac attgagcaca tttctttcat cagcgcgatg catgcaatca tcacttcgca    240
atcttgacaa acatcctcaa tgattcctcc acctctccca acaaagtcaa tgcattcatc    300
cttggatctt ctcctccacc gaacggccgt gaagccgact ccattagtgc atccagtcca    360
tcaaaatacc gtatgaattc ccgaaaagat tcacttgcca agtactgttt gtcatcctcc    420
```

| tcttcaggta tctcatcaat gagtgcattt gcagctatac gaatctttga ctcggaaatc | 480 |
| aatcc | 485 |

<210> SEQ ID NO 21
<211> LENGTH: 702
<212> TYPE: DNA
<213> ORGANISM: Artificial Sequence
<220> FEATURE:
<223> OTHER INFORMATION: Synthetic sequence
<220> FEATURE:
<223> OTHER INFORMATION: Turbo GFP

<400> SEQUENCE: 21

| atgttggaga gcgacgagag cggcctgccc gccatggaga tcgagtgccg catcaccggc | 60 |
| accctgaacg gcgtggagtt cgagctggtg ggcggcggag agggcacccc cgagcagggc | 120 |
| cgcatgacca acaagatgaa gagcaccaaa ggcgccctga ccttcagccc ctacctgctg | 180 |
| agccacgtga tgggctacgg cttctaccac ttcggcacct accccagcgg ctacgagaac | 240 |
| cccttcctgc acgccatcaa caacggcggc tacaccaaca cccgcatcga gaagtacgag | 300 |
| gacggcggcg tgctgcacgt gagcttcagc taccgctacg aggccggccg cgtgatcggc | 360 |
| gacttcaagg tgatgggcac cggcttcccc gaggacagcg tgatcttcac cgacaagatc | 420 |
| atccgcagca acgccaccgt ggagcacctg caccccatgg gcgataacga tctggatggc | 480 |
| agcttcaccc gcaccttcag cctgcgcgac ggcggctact acagctccgt ggtggacagc | 540 |
| cacatgcact tcaagagcgc catccacccc agcatcctgc agaacggggg ccccatgttc | 600 |
| gccttccgcc gcgtggagga ggatcacagc aacaccgagc tgggcatcgt ggagtaccag | 660 |
| cacgccttca agaccccgga tgcagatgcc ggtgaagaat aa | 702 |

<210> SEQ ID NO 22
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: 5303630 Promoter

<400> SEQUENCE: 22

| aataagcata catcatatga atacaattca gcttaaattt atcatacaaa gatgtaagtg | 60 |
| cagcgtgggt ctgtaacgat cgggcgtaat ttaagataat gcgagggacc gggggaggtt | 120 |
| ttggaacgga atgaggaatg ggtcatggcc cataataata atatgggttt ggtcgcctcg | 180 |
| cacagcaacc gtacgtgcga aaaaggaaca gatccattta ataagttgaa cgttattctt | 240 |
| tcctatgcaa tgcgtgtatc ggaggcgaga gcaagtcata ggtggctgcg cacaataatt | 300 |
| gagtctcagc tgagcgccgt ccgcgggtgg tgtgagtggt catcctcctc ccggcctatc | 360 |
| gctcacatcg cctctcaatg gtggtggtgg ggcctgatat gacctcaatg ccgacccata | 420 |
| ttaaacccca gtaaagcatt caccaacgaa cgagggggctc ttttgtgtgt gttttgagta | 480 |
| tgattttaca cctctttgtg catctctctg gtcttccttg gttcccgtag tttgggcatc | 540 |
| atcactcacg cttccctcga ccttcgttct tcctttacaa ccccgacaca ggtcagagtt | 600 |
| ggagtaatca aaaaggggt gcacgaatga gatacattag attttgacag atatcctttt | 660 |
| actggagagg gttcaaggga tcaaatgaac agcgggcgtt ggcaatctag ggagggatcg | 720 |
| gaggttggca gcgagcgaaa gcgtgtccat cctttggct gtcacacctc acgaaccaac | 780 |
| tgttagcagg ccagcacaga tgacatacga gaatctttat tatatcgtag accttatgtg | 840 |

| | |
|---|---|
| gatgaccttt ggtgctgtgt gtctggcaat gaacctgaag gcttgatagg gaggtggctc | 900 |
| ccgtaaaccc tttgtccttt ccacgctgag tctcccccgc actgtccttt atacaaattg | 960 |
| ttacagtcat ctgcaggcgg tttttctttg gcaggcaaac | 1000 |

```
<210> SEQ ID NO 23
<211> LENGTH: 318
<212> TYPE: DNA
<213> ORGANISM: Nannochloropsis gaditana
<220> FEATURE:
<221> NAME/KEY: misc_feature
<223> OTHER INFORMATION: Elf3 terminator

<400> SEQUENCE: 23
```

| | |
|---|---|
| ggcactgtaa ccccggttcc gctcgacgaa ggctgggagc gcccctttcgg tgggataaaa | 60 |
| tggatgcttt accgctgcgc ttcggctgag gaagagagaa atgcgagcgg ggatcggggt | 120 |
| cctagaaacg aagaaaggag aacaagttcc tggccaaaga aaaacaagac aaataccctc | 180 |
| tccaggcctg gcccattac ttttttttgc tgtttcttat acctgcactc gtgcttctct | 240 |
| agtctgtcga gaccttacct gatcttcctc cctccatcgc tccccgcccc cccatccga | 300 |
| gcaaccgtcg accatacg | 318 |

```
<210> SEQ ID NO 24
<211> LENGTH: 1215
<212> TYPE: DNA
<213> ORGANISM: Cyclotella sp.
<220> FEATURE:
<221> NAME/KEY: misc_feature
<223> OTHER INFORMATION: Enoyl ACP Reductase gene

<400> SEQUENCE: 24
```

| | |
|---|---|
| atgatcgcgc tgtcatctcc agttttcttt tcctttctta gtcgtcgctc ccccacaaaa | 60 |
| tcaatttcga aactatcgtc gagactatca atcgagagca ccatgatgtt ccgccgtagc | 120 |
| accgtattcg ccgccgccgc ggctcttgtt tatggcgcat cctctgtagc agcctttgca | 180 |
| ccgtgcacat ctgttggcaa catcgtatcc aagaccaacc cggccaccat tcagcaacaa | 240 |
| tcgcaatctc gtcaatacag ttctacgcag cttcaaatgg caggacctgc tcaagttgat | 300 |
| ttaaccggaa aagttgccctt tgttgctggt gttgccgact cttctggata cggttgggcc | 360 |
| attgctcgtg cattggccag cgctggcgcc actattattg taggaacatg gccaccggtt | 420 |
| ctgaaaattt ttgaaagcgg gcttaggaag ggctcgtttg atgaggattc gattcttcca | 480 |
| gatggtagca agatgaatat cgagaaggtc taccctctcg atgctgtgtt tgatactgct | 540 |
| gatgatgtac ccgatgaaat caaagaaaac aaacgttatg ctggactctc tggatacact | 600 |
| attgaagagg ttgctaaggc aattgaggct gattatggca aaatcgacat ccttgttcac | 660 |
| tcgcttgcca acggtcctga agttaccaag ccactcctag aaacctcccg caaaggatac | 720 |
| cttgcggcat cctctgcctc tgcctactcc gccgtgtccc ttctccaaaa atttggcccc | 780 |
| atcatgaacg agggtggaaa catgctctcc cttacctaca ttgcatctga aaagtcatt | 840 |
| cctggctatg gaggcggcat gtcttctgct aaagctcagc ttgagtctga cacccgtaca | 900 |
| ctggcatacg aagctggaag gaagtggaag cttcgcgtca acactatttc agctggccca | 960 |
| ctcaaatcgc gtgcagcttc tgctattgga aaggaacctg gtcagaagac tttcattgag | 1020 |
| tacgccattg attactctaa ggcgaatgcc ccactggctc aggacttgta caatgaagac | 1080 |
| gttggaaatt cagcgttatt cctctgctct ggacttgcga gaaccgtgac tggtgttact | 1140 |
| ttgtacgttg ataatggtct tcatgctatg gaatggctc ttgacagtga atctatgtct | 1200 |

```
gacagaaatg tataa                                                    1215
```

<210> SEQ ID NO 25
<211> LENGTH: 1000
<212> TYPE: DNA
<213> ORGANISM: Nannochloropsis gaditana
<220> FEATURE:
<221> NAME/KEY: misc_feature
<223> OTHER INFORMATION: eIF3a Promoter

<400> SEQUENCE: 25

```
tcataatcaa agatgagcca gccacgaagc taccggagaa ttctgtaaga aaaatgttta     60
aagttgaaaa tgctaacagt gaagtgatat ccttttttaa tggagtgttg aggtgaagtc    120
tagcatcgta ggggaaaaca ggattctgtg tcttccattc tactccttga taaagcgaag    180
aaatccgaca aaaccaaaga gattgttcaa gtttaagatt tgtaagcgta caactatgaa    240
cttcttctct ttgtaggcct gagtggtcgt atgcatacga ttcatgaagt gaatcagtat    300
cgctggattt tgcttaggag taaagcacaa ctaagaaaat atgctgcctg gcaggcatcc    360
tgagacatga ggcaagcgac gtagcaattg aatcctaatt taagccaggg catctgtatg    420
actctgttag ttaattgatg aaccaatgag ctttaaaaaa aaatcgttgc gcgtaatgta    480
gttttaattc tccgccttga ggtgcggggc catttcggac aaggttcttt ggacggagat    540
ggcagcatgt gtcccttctc caaattggtc cgtgtggtag ttgagatgct gccttaaaat    600
tctgctcggt catcctgcct tcgcattcac tcctttcgag ctgtcgggtt cctcacgagg    660
cctccgggag cggattgcgc agaaaggcga cccggagaca cagagaccat acaccgacta    720
aattgcactg gacgatacgg catggcgacg acgatggcca agcattgcta cgtgattatt    780
cgccttgtca ttcagggaga aatgatgaca tgtgtggac ggtctttata tgggaagagg    840
gcatgaaaat aacatggcct ggcgggatgg agcgtcacac ctgtgtatgc gttcgatcca    900
caagcaactc accatttgcg tcggggcctg tctccaatct gctttaggct acttttctct    960
aatttagcct attctataca gacagagaca cacagggatc                        1000
```

<210> SEQ ID NO 26
<211> LENGTH: 163
<212> TYPE: DNA
<213> ORGANISM: Nannochloropsis gaditana
<220> FEATURE:
<221> NAME/KEY: misc_feature
<223> OTHER INFORMATION: T9 Terminator

<400> SEQUENCE: 26

```
gagtcaaggg ggaaggtgca tagtgtgcaa caacagcatt aacgtcaaag aaaactgcac     60
gttcaagccc gcgtgaacct gccggtcttc tgatcgccta catatagcag atactagttg    120
tacttttttt tccaaaggga acattcatgt atcaatttga aat                     163
```

<210> SEQ ID NO 27
<211> LENGTH: 11825
<212> TYPE: DNA
<213> ORGANISM: Artificial Sequence
<220> FEATURE:
<221> NAME/KEY: misc_feature
<223> OTHER INFORMATION: synthetic construct
<220> FEATURE:
<221> NAME/KEY: misc_feature
<223> OTHER INFORMATION: pSGE-6067 construct

<400> SEQUENCE: 27

-continued

```
aacaagtttt gattttgtgt ttgtcgtatt tttacgcagg aaaatgtcag agccgataca        60
ttcgagctac ctggggttgt cttttaaga gtcccagcat tgtgttcacc tacgatagtg        120
catggctgca agtaaattca ttttgcgata accacaaaac tagccaattt acgaatctgt       180
gaagaagttt ttcgcgttct acggtcctct tgtagtaacc catcgatgtt gcttcaagat       240
atgggcgctg gtcgatggaa aaaccacag gactagttaa aatcatagat tccacgaaat        300
tattaaaata ttatttttca tgccctgcgg tccgtgaaga ctgcgagcac gcgccttagg       360
agatgagagc ctctcgacat ctcctgcata catctgcaga cgacaagaga gcatcagggg      420
ctaagggagg catggaatag cgtcgacaca tcgacagctc attccatatt ctctctaagt      480
tcccctgtgg agcgattgct tcgatcagtg aagatcacct ggcccttcc tcgttgaaag      540 tgaggctcag gacggtcgga aggtattgta ttggtacgct ttgacgtagc ctttctcgttg     600 acactttgac ttgcatacga cccttgtggc gacggctgca tttgtgcgct gttgctccaa      660
gaactatgca tcgaaggcac acgccctgga agccccgaca cctctgtttg agacactgct      720
tcaaatcact tgagcaggac tcacaatgag agtcatcgt attgggtttg tcccggagac       780
ggtcacagct tgtctgtaag cggatgccgg gagcagacaa gcccgtcagg gcgcgtcagc      840
gggtgttggc gggtgtcggg gctggcttaa ctatgcggca tcagagcaga ttgtactgag      900
agtgcaccat aaattcccgt tttaagagct tggtgagcgc taggagtcac tgccaggtat      960
cgtttgaaca cggcattagt cagggaagtc ataacacagt cctttcccgc aattttcttt    1020
ttctattact cttggcctcc tctagtacac tctatatttt tttatgcctc ggtaatgatt   1080
ttcatttttt ttttccacc tagcggatga ctctttttt ttcttagcga ttggcattat    1140
cacataatga attatacatt atataaagta atgtgatttc ttcgaagaat atactaaaaa      1200
atgagcagga aagataaacg aaggcaaaga tgacagagca gaaagcccta gtaaagcgta     1260
ttacaaatga aaccaagatt cagattgcga tctcttttaaa gggtggtccc ctagcgatag   1320
agcactcgat cttcccagaa aaagaggcag aagcagtagc agaacaggcc acacaatcgc     1380
aagtgattaa cgtccacaca ggtataggggt ttctggacca tatgatacat gctctggcca   1440
agcattccgg ctggtcgcta atcgttgagt gcattggtga cttacacata gacgaccatc    1500
acaccactga agactgcggg attgctctcg gtcaagcttt taaagaggcc ctaggggccg   1560
tgcgtggagt aaaaaggttt ggatcaggat ttgcgccttt ggatgaggca cttttccagag   1620 cggtggtaga tcttcgaac aggccgtacg cagttgtcga acttggtttg caaagggaga    1680
aagtaggaga tctctcttgc gagatgatcc cgcattttct tgaaagcttt gcagaggcta   1740
gcagaattac cctccacgtt gattgtctgc gaggcaagaa tgatcatcac cgtagtgaga   1800
gtgcgttcaa ggctcttgcg gttgccataa gagaagccac ctcgcccaat ggtaccaacg   1860
atgttccctc caccaaaggt gttcttatgt agtgacaccg attatttaaa gctgcagcat   1920
acgatatata tacatgtgta tatatgtata cctatgaatg tcagtaagta tgtatacgaa   1980
cagtatgata ctgaagatga caaggtaatg catcattcta tacgtgtcat tctgaacgag   2040
gcgcgctttc ctttttttctt tttgcttttt cttttttttt ctcttgaact cgacggatct   2100
atgcggtgtg aaataccgca cagatgcgta aggagaaaat accgcatcag gaaattgtaa    2160
cgttaatatt ttgttaaaat tcgcgttaaa tttttgttaa atcagctcat tttttaacca   2220
ataggccgaa atcggcaaaa tcccgtatg gtcgacggtt gctcggatgg gggggcggg    2280 gagcgatgga gggaggaaga tcaggtaagg tctcgacaga ctagagaagc acgagtgcag   2340
gtataagaaa cagcaaaaaa aagtaatggg cccaggcctg gagagggtat ttgtcttgtt    2400
```

```
tttctttggc caggaacttg ttctcctttc ttcgtttcta ggaccccgat ccccgctcgc    2460
atttctctct tcctcagccg aagcgcagcg gtaaagcatc cattttatcc caccgaaagg    2520
gcgctcccag ccttcgtcga gcggaaccgg ggttacagtg ccatttaaat ttattcttca    2580
ccggcatctg catccggggt cttgaaggcg tgctggtact ccacgatgcc cagctcggtg    2640
ttgctgtgat cctcctccac gcggcggaag gcgaacatgg ggccccgtt ctgcaggatg     2700 ctggggtgga tggcgctctt gaagtgcatg tggctgtcca ccacggagct gtagtagccg    2760
ccgtcgcgca ggctgaaggt gcgggtgaag ctgccatcca gatcgttatc gcccatgggg    2820
tgcaggtgct ccacggtggc gttgctgcgg atgatcttgt cggtgaagat cacgctgtcc    2880
tcggggaagc cggtgcccat caccttgaag tcgccgatca cgcggccggc ctcgtagcgg    2940
tagctgaagc tcacgtgcag cacgccgccg tcctcgtact tctcgatgcg ggtgttggtg    3000
tagccgccgt tgttgatggc gtgcaggaag gggttctcgt agccgctggg gtaggtgccg    3060
aagtggtaga agccgtagcc catcacgtgg ctcagcaggt aggggctgaa ggtcagggcg    3120
cctttggtgc tcttcatctt gttggtcatg cggccctgct cggggggtgcc ctctccgccg    3180 cccaccagct cgaactccac gccgttcagg gtgccggtga tgcggcactc gatctccatg    3240
gcgggcaggc cgctctcgtc gctctccaac atgtttgcct gccaaagaaa aaccgcctgc    3300
agatgactgt aacaatttgt ataaaggaca gtgcggggga gactcagcgt ggaaaggaca    3360
aagggtttac gggagccacc tccctatcaa gccttcaggt tcattgccag acacacagca    3420
ccaaaggtca tccacataag gtctacgata taataaagat tctcgtatgt catctgtgct    3480
ggcctgctaa cagttggttc gtgaggtgtg acagccaaaa ggatggacac gctttcgctc    3540
gctgccaacc tccgatccct ccctagattg ccaacgcccg ctgttcattt gatcccttga    3600
accctctcca gtaaaaggat atctgtcaaa atctaatgta tctcattcgt gcaccccttt    3660
tttgattact ccaactctga cctgtgtcgg ggttgtaaag gaagaacgaa ggtcgaggga    3720
agcgtgagtg atgatgccca aactacggga accaaggaag accagagaga tgcacaaaga    3780
ggtgtaaaat catactcaaa acacacacaa aagagcccct cgttcgttgg tgaatgcttt    3840
actgggtttt aatatgggtc ggcattgagg tcatatcagg ccccaccacc accattgaga    3900
ggcgatgtga gcgataggcc gggaggagga tgaccactca caccaccgc ggacggcgct    3960 cagctgagac tcaattattg tgcgcagcca cctatgactt gctctcgcct ccgatacacg    4020
cattgcatag gaaagaataa cgttcaactt attaaatgga tctgttcctt tttcgcacgt    4080
acggttgctg tgcgaggcga ccaaacccat attattatta tgggccatga cccattcctc    4140
attccgttcc aaaacctccc ccggtccctc gcattatctt aaattacgcc cgatcgttac    4200
agacccacgc tgcacttaca tctttgtatg ataaatttaa gctgaattgt attcatatga    4260
tgtatgctta ttatcaaaag aatagaccga gatagggttg agtgttgttc cagtttggaa    4320
caagagtcca ctattaaaga acgtggactc caacgtcaaa gggcgaaaaa ccgtctatca    4380
gggcgatggc ccactacgtg aaccatcacc ctaatcaagt ttttggggt cgaggtgccg     4440 taaagcacta aatcggaacc ctaaagggag cccccgattt agagcttgac ggggaaagcc    4500
ggcgaacgtg gcgagaaagg aagggaagaa agcgaaagga gcgggcgcta gggcgctggc    4560
aagtgtagcg gtcacgctgc gcgtaaccac cacacccgcc gcgcttaatg cgccgctaca    4620
gggcgcgtcc attcgccatt caggctgcgc aactgttggg aagggcgatc ggtgcgggcc    4680
tcttcgctat tacgccagct ggcgaaaggg ggatgtgctg caaggcgatt aagttgggta    4740
```

```
acgccagggt tttcccagtc acgacgttgt aaaacgacgg ccagtgaatt gtaatacgac    4800
tcactatagg gcgaattgga gctccaccgc ggtggcggcc gccgtgcagg tgtacagatt    4860
gaaggaaaca atggagatat ctttggcagt tgaaaaccgt gttcgaatca tgcttttcta    4920
ctctccaact gagacgaaat ttatagcgcc atgtcgcttc tgactaccag gcttaggaag    4980
gcctcatcac aagctggatc ggttcgaatt aagcaggcac tgaagccaag cttgcaagac    5040
agccaccttt taattccctc aaaacacttt ctcaattcag cccggtaaat atgccgattc    5100
acagcggcca agatagaggg gaggttagca agaatgttgc gatccctccc cagtcgttgc    5160
ctcgcacaca acctaggcct tcaccttccc atggaaaatt gagaagtgaa tattggtttt    5220
cttacggcat atcagatgaa atcatgaccc ctaaacatga agagctgcag gcaaaacacc    5280
tgctctggac gagcacgatg aaatctcgag aacccgccgt acttcagttg atcccgcatg    5340
atgacggccg ccattgaaat aagccacctc actttattct agcaccgatt ccaccgttg    5400 tgagggccga acgaggacaa tttcgtgcga acaagcacg aacacgcaca cgattagtag    5460
tacagacgag cagatcgatg gcatgcggca cggtctcgcg ttctcggcga ccaggacaac    5520
ggagcagagg gaggcctgcc gagttccgag gggcatttta gtccaaaatt gtgttgacac    5580
gtgaacaagt ggcttgaaaa gaggaaggaa atgcctgggt ttcccttcga gagcgggaac    5640
tcgcttgtgc gtcatcctag ctacccatgg tcccttttgtg ggggaggctg tttcgtccta    5700
ccgaatgtgt ggcgctccat gcatcttctg cctcccaaac caccaacatg agcacgcgaa    5760
ggaaggagaa aaaagtggcc gcaacgttct cttctcatat ttattgtctc atcacaaaca    5820
taggtacata atacaacaat catggatccc cgggtaccga gctcgatggc caagcctttg    5880
tcccaagagg aatccacgct gatcgaacgt gcaactgcga ccatcaacag catacctatt    5940
agcgaggact actcggtggc cagtgcagcc ctctcgtccg acggtcggat ctttaccggc    6000
gtgaatgtat atcatttcac cggagggcca tgcgcggagc tcgtggtcct cggaacggcc    6060 gctgcgctg ctgccggaaa tctgacgtgc atagtggcca tcgggaacga aaaccgcggc    6120
attctgtctc cgtgcgggcg atgtcggcag gtgctgcttg acttgcaccc ggggatcaag    6180
gcaattgtca aagattccga tgggcagccc acagcggttg gcatcaggga gttgcttccc    6240
tctggctacg tctgggaggg ttgaagatcc tcactctgtc gcgctgttgg cgccactact    6300 ttggggggtac gagtttaggc tgccttggct gggataaaga atgataagtt tacataattt    6360
gtattggaaa tccatcgagt tttggattca gttgacgtct cctgcgttac tatgtcttca    6420
ttctctccag tatcaatgcc tatggttcgt cgacattgag cacatttctt tcatcagcgc    6480
gatgcatgca atcatcactt cgcaatcttg acaaacatcc tcaatgattc ctccacctct    6540
cccaacaaag tcaatgcatt catccttgga tcttctcctc caccgaacgg ccgtgaagcc    6600
gactccatta gtgcatccag tccatcaaaa taccgtatga attcccgaaa agattcactt    6660
gccaagtact gtttgtcatc ctcctcttca ggtatctcat caatgagtgc atttgcagct    6720
atacgaatct ttgactcgga aatcaatccg cggccgcttc ataatcaaag atgagccagc    6780
cacgaagcta ccggagaatt ctgtaagaaa aatgtttaaa gttgaaaatg ctaacagtga    6840
agtgatatcc ttttttaatg gagtgttgag gtgaagtcta gcatcgtagg ggaaaacagg    6900
attctgtgtc ttccattcta ctccttgata aagcgaagaa atccgacaaa accaaagaga    6960
ttgttcaagt ttaagatttg taagcgtaca actatgaact tcttctcttt gtaggcctga    7020
gtggtcgtat gcatacgatt catgaagtga atcagtatcg ctggattttg cttaggagta    7080
aagcacaact aagaaaatat gctgcctggc aggcatcctg agacatgagg caagcgacgt    7140
```

```
agcaattgaa tcctaattta agccagggca tctgtatgac tctgttagtt aattgatgaa    7200
ccaatgagct ttaaaaaaaa atcgttgcgc gtaatgtagt tttaattctc cgccttgagg    7260
tgcggggcca tttcggacaa ggttctttgg acggagatgg cagcatgtgt cccttctcca    7320
aattggtccg tgtggtagtt gagatgctgc cttaaaattc tgctcggtca tcctgccttc    7380
gcattcactc ctttcgagct gtcgggttcc tcacgaggcc tccgggagcg gattgcgcag    7440
aaaggcgacc cggagacaca gagaccatac accgactaaa ttgcactgga cgatacggca    7500
tggcgacgac gatggccaag cattgctacg tgattattcg ccttgtcatt cagggagaaa    7560
tgatgacatg tgtgggacgg tctttatatg ggaagagggc atgaaaataa catggcctgg    7620
cgggatggag cgtcacacct gtgtatgcgt tcgatccaca agcaactcac catttgcgtc    7680
ggggcctgtc tccaatctgc tttaggctac ttttctctaa tttagcctat tctatacaga    7740
cagagacaca cagggatcgg taccatgatc gcgctgtcat ctccagtttt cttttccttt    7800
cttagtcgtc gctcccccac aaaatcaatt tcgaaactat cgtcgagact atcaatcgag    7860
agcaccatga tgttccgccg tagcaccgta ttcgccgccg ccgcggctct tgtttatggc    7920
gcatcctctg tagcagcctt tgcaccgtgc acatctgttg caacatcgt atccaagacc    7980 aacccggcca ccattcagca acaatcgcaa tctcgtcaat acagttctac gcagcttcaa    8040
atggcaggac ctgctcaagt tgatttaacc ggaaaagttg cctttgttgc tggtgttgcc    8100
gactcttctg gatacggttg ggccattgct cgtgcattgg ccagcgctgg cgccactatt    8160
attgtaggaa catggccacc ggttctgaaa atttttgaaa gcgggcttag gaagggctcg    8220
tttgatgagg attcgattct tccagatggt agcaagatga atatcgagaa ggtctaccct    8280
ctcgatgctg tgtttgatac tgctgatgat gtacccgatg aaatcaaaga aaacaaacgt    8340
tatgctggac tctctggata cactattgaa gaggttgcta aggcaattga ggctgattat    8400
ggcaaaatcg acatccttgt tcactcgctt gccaacggtc ctgaagttac caagccactc    8460
ctagaaacct cccgcaaagg ataccttgcg gcatcctctg cctctgccta ctccgccgtg    8520
tcccttctcc aaaaatttgg ccccatcatg aacgagggtg gaaacatgct ctcccttacc    8580
tacattgcat ctgagaaagt cattcctggc tatggaggcg gcatgtcttc tgctaaagct    8640
cagcttgagt ctgacacccg tacactggca tacgaagctg gaaggaagtg gaagcttcgc    8700
gtcaacacta tttcagctgg cccactcaaa tcgcgtgcag cttctgctat tggaaaggaa    8760
cctggtcaga agactttcat tgagtacgcc attgattact ctaaggcgaa tgccccactg    8820
gctcaggact tgtacaatga agacgttgga aattcagcgt tattcctctg ctctggactt    8880
gcgagaaccg tgactggtgt tactttgtac gttgataatg gtcttcatgc tatgggaatg    8940
gctcttgaca gtgaatctat gtctgacaga aatgtataag agtcaagggg gaaggtgcat    9000
agtgtgcaac aacagcatta acgtcaaaga aaactgcacg ttcaagcccg cgtgaacctg    9060
ccggtcttct gatcgcctac atatagcaga tactagttgt acttttttt ccaaagggaa    9120 cattcatgta tcaatttgaa attctagaac tagtggatcc cccgggctgc aggaattcga    9180
tatcaagctt atcgataccg tcgacctcga ggggggggccc ggtaccagct tttgttccct    9240
ttagtgaggg ttaatttcga gcttggcgta atcatggtca tagctgtttc ctgtgtgaaa    9300
ttgttatccg ctcacaattc cacacaacat acgagccgga agcataaagt gtaaagcctg    9360
```

```
gggtgcctaa tgagtgagct aactcacatt aattgcgttg cgctcactgc ccgctttcca    9420
gtcgggaaac ctgtcgtgcc agctgcatta atgaatcggc caacgcgcgg ggagaggcgg    9480
tttgcgtatt gggcgctctt ccgcttcctc gctcactgac tcgctgcgct cggtcgttcg    9540
gctgcggcga gcggtatcag ctcactcaaa ggcggtaata cggttatcca cagaatcagg    9600
ggataacgca ggaaagaaca tgtgagcaaa aggccagcaa aaggccagga accgtaaaaa    9660
ggccgcgttg ctggcgtttt tccataggct ccgcccccct gacgagcatc acaaaaatcg    9720
acgctcaagt cagaggtggc gaaacccgac aggactataa agataccagg cgtttccccc    9780
tggaagctcc ctcgtgcgct ctcctgttcc gaccctgccg cttaccggat acctgtccgc    9840
ctttctccct tcgggaagcg tggcgctttc tcatagctca cgctgtaggt atctcagttc    9900
ggtgtaggtc gttcgctcca agctgggctg tgtgcacgaa ccccccgttc agcccgaccg    9960
ctgcgcctta tccggtaact atcgtcttga gtccaacccg gtaagacacg acttatcgcc   10020
actggcagca gccactggta acaggattag cagagcgagg tatgtaggcg gtgctacaga   10080
gttcttgaag tggtggccta actacggcta cactagaaga acagtatttg gtatctgcgc   10140
tctgctgaag ccagttacct tcggaaaaag agttggtagc tcttgatccg gcaaacaaac   10200
caccgctggt agcggtggtt tttttgtttg caagcagcag attacgcgca gaaaaaaagg   10260
atctcaagaa gatcctttga tcttttctac ggggtctgac gctcagtgga acgaaaactc   10320
acgttaaggg attttggtca tgagattatc aaaaaggatc ttcacctaga tccttttaaa   10380
ttaaaaatga agttttaaat caatctaaag tatatatgag taaacttggt ctgacagtta   10440
ccaatgctta atcagtgagg cacctatctc agcgatctgt ctatttcgtt catccatagt   10500
tgcctgactc cccgtcgtgt agataactac gatacgggag ggcttaccat ctggccccag   10560
tgctgcaatg ataccgcgag acccacgctc accggctcca gatttatcag caataaacca   10620
gccagccgga agggccgagc gcagaagtgg tcctgcaact ttatccgcct ccatccagtc   10680
tattaattgt tgccgggaag ctagagtaag tagttcgcca gttaatagtt tgcgcaacgt   10740
tgttgccatt gctacaggca tcgtggtgtc acgctcgtcg tttggtatgg cttcattcag   10800
ctccggttcc caacgatcaa ggcgagttac atgatccccc atgttgtgca aaaaagcggt   10860
tagctccttc ggtcctccga tcgttgtcag aagtaagttg gccgcagtgt tatcactcat   10920
ggttatggca gcactgcata attctcttac tgtcatgcca tccgtaagat gcttttctgt   10980
gactggtgag tactcaacca agtcattctg agaatagtgt atgcggcgac cgagttgctc   11040
ttgcccggcg tcaatacggg ataataccgc gccacatagc agaactttaa aagtgctcat   11100
cattggaaaa cgttcttcgg ggcgaaaact ctcaaggatc ttaccgctgt tgagatccag   11160
ttcgatgtaa cccactcgtg cacccaactg atcttcagca tcttttactt tcaccagcgt   11220
ttctgggtga gcaaaaacag gaaggcaaaa tgccgcaaaa aagggaataa gggcgacacg   11280
gaaatgttga atactcatac tcttcctttt tcaatattat tgaagcattt atcagggtta   11340
ttgtctcatg agcggataca tatttgaatg tatttagaaa aataaacaaa tagggggttcc   11400 gcgcacattt ccccgaaaag tgccacctga cggatcgctt gcctgccatg gtaacttaca   11460
cgcgcctcgt atctttaat gatggaataa tttgggaatt tactctgtgt ttatttattt   11520
ttatgttttg tatttggatt ttagaaagta aataaagaag gtagaagagt tacggaatga   11580
agaaaaaaaa ataaacaaag gtttaaaaaa tttcaacaaa aagcgtactt tacatatata   11640
tttattagac aagaaaagca gattaaatag atatacattc gattaacgat aagtaaaatg   11700
```

```
taaaatcaca ggattttcgt gtgtggtctt ctacacagac aagatgaaac aattcggcat    11760
taatacctga gagcaggaag agcaagataa aaggtagtat ttgttggcga tccccctaga    11820
gtctt                                                                11825
```

US 9,447,422 B2

AUTONOMOUS REPLICATION SEQUENCES AND EPISOMAL DNA MOLECULES

CROSS-REFERENCE TO RELATED APPLICATIONS

This application claims priority under U.S.C. §119(e) to U.S. Provisional Patent Application No. 61/734,285 filed Dec. 6, 2012, the entire contents of which is herein incorporated by reference.

REFERENCE TO A SEQUENCE LISTING

This application contains references to nucleic acid sequences which have been submitted concurrently herewith as the sequence listing text file "Sequence Listing_SGI-060.20US.txt", file size 4 kilobytes (kb), created on 6 Dec. 2012. The aforementioned sequence listing is hereby incorporated by reference in its entirety pursuant to 37 C.F.R. §1.52(e)(iii)(5).

FIELD OF THE INVENTION

The present invention relates, in some embodiments, to genetic elements for the manipulation of eukaryotic cells in biotech applications. The present invention also relates, in some embodiments, to methods of identifying ARS elements from organisms of interest.

BACKGROUND

An Autonomously Replicating Sequence (ARS) is a sequence that serves as an origin of DNA replication on eukaryotic chromosomes. An ARS is required for DNA replication during cell division, and is a necessary part of a functional synthetic chromosome (Gilbert (2001) *Science* 294:96-100). Additionally, some ARS sequences have been shown to function as matrix attachment regions (MARs), which can improve heterologous genes' amount of expression, consistency of expression over time, and degree of repression by heterochromatin formation (Kim et al. 2007).

While DNA sequences that constitute the origins of DNA replication are readily identifiable in bacteria, origins of replication in eukaryotes have been more difficult to identify (Gilbert 2001). ARS primary sequences are not significantly conserved, either within or across eukaryotic species, although the location of some ARS elements is conserved across species (Gilbert 2001). For example, *Saccharomyces cerevisiae* (budding yeast) (Smith & Boeke (1997) *Genes Dev.* 11:241-54) and *Pisum sativum* (garden pea) (Van't Hof (1996) "DNA Replication in Eukaryotic Cells," CSHL Press) both have an ARS between the 18S and 5S ribosomal RNA genes in their respective ribosomal repeat regions.

The current methodology for acquiring non-*Saccharomyces cerevisiae* ARS elements for use in artificial chromosomes is through random acquisition with large (~100 kbp) pieces of genomic DNA (Basu et al. (2005) *BMC Biotechnol.* 5:21). This process is both inefficient and liable to import sequences that are deleterious to optimal industrial performance, but which happen to be located proximal on a chromosome to an ARS. Once an ARS is located, it can be placed into artificial chromosomes or plasmids to permit those constructs to replicate in a host of interest (Henning et al. (1999) *Proc. Nat'l. Acad. Sci. USA* 96:592-97). At present, there are no known *Nannochloropsis* sp.—or heterokont—ARS elements available.

SUMMARY

The present invention provides a number of nucleic acid sequences that were isolated from the *Nannochloropsis* genome by analyzing the region of ribosomal RNA gene repeats (see Example 1) and identifying AT-rich relative to surrounding sequences. Insertion of these sequences into plasmids that carried selectable marker genes demonstrated that the sequences were necessary and sufficient for replication of plasmids (Episomal DNA Molecules or EDMs) in cells maintained under selection. Genes maintained on EDMs were demonstrated to have better expression of the encoded polypeptides than genes integrated into the genome.

The sequences were tested characterized as Autonomously Replicating Sequences (ARSs) by their ability to transform *Nannochloropsis* and to allow for 1) recovery of DNA molecules from uncut genomic DNA that a) migrated as circular molecules in gel electrophoresis, b) persisted in algal cultures under selection, and c) were intact. EDMs that included these ARSs were recovered from uncut isolated DNA from EDM-transformed cells were used to transform *E. coli*, where the EDMs were also found to reside intact.

Thus, provided herein are ARSs isolated from *Nannochloropsis* sp. that can support independent replication of episomal DNA molecules (EDMs) in eukaryotic cells, including microorganisms such as algae and heterokonts. Also provided are EDMs that include an ARS as provided herein, and methods of their use in expressing genes in algae and heterokonts.

In a first aspect, provided herein is an isolated or recombinant nucleic acid molecule that includes an ARS having a nucleic acid sequence having at least 85% identity to SEQ ID NO:13 or SEQ ID NO:14. The nucleic acid molecule that includes the ARS further includes at least one nucleic acid sequence that is heterologous with respect to the ARS, for example, where the ARS is identical to a naturally-occurring sequence of an organism, the ARS is not adjacent to sequences it is found adjacent to in the organism from which the sequence is isolated. For example, if identical to a naturally-occurring genomic sequence, the ARS can be provided in a nucleic acid molecule where the ARS is juxtaposed with at least one nucleic acid sequence not isolated from the rDNA region of the genome of the organism from which ARS has been isolated. A nucleic acid molecule as provided herein that includes a sequence having at least 85% identity to SEQ ID NO:13 or SEQ ID NO:14 can further comprise, for example, a reporter gene, selectable marker gene, a gene encoding a polypeptide of interest, or a gene encoding a functional RNA that is not a ribosomal RNA, where any of the foregoing may not be from genome of the organism from which the ARS has been isolated. The ARS that includes a nucleic acid sequence having at least 85% identity to SEQ ID NO:13 or SEQ ID NO:14 can have, for example, at least 90%, at least 95%, at least 96%, at least 97%, at least 98%, at least 99%, or 100% identity to SEQ ID NO:13 or SEQ ID NO:14. In some examples, an isolated or recombinant nucleic acid molecule includes an ARS having a nucleic acid sequence having at least 85% identity to SEQ ID NO:13 and a nucleic acid sequence having at least 85% identity to SEQ ID NO:14 juxtaposed with at least one nucleic acid sequence that is heterologous with respect to SEQ ID NO:13 and/or SEQ ID NO:14.

An ARS as provided herein is functional in a eukaryotic cell, for example, a microbial cell such as a fungal, algal, or heterokont cell. In various examples, an ARS supports replication of an episomal DNA molecule (EDM) in diatom and/or Eustigmatophyte cells.

In some examples, a nucleic acid molecule provided herein includes an ARS having at least 85%, at least 90%, at least 95%, at least 96%, at least 97%, at least 98%, at least 99%, or 100% identity to at least 150 contiguous nucleotides of SEQ ID NO:1, SEQ ID NO:5; SEQ ID NO:6; SEQ ID NO:7; SEQ ID NO:8; SEQ ID NO:9; or SEQ ID NO:10, in which the nucleic acid sequence also has at least 85% identity to SEQ ID NO:13. In some examples, a nucleic acid molecule provided herein includes an ARS having at least 85%, at least 90%, at least 95%, at least 96%, at least 97%, at least 98%, at least 99%, or 100% identity to at least 150 contiguous nucleotides of SEQ ID NO:5; SEQ ID NO:6; SEQ ID NO:7; SEQ ID NO:11; or SEQ ID NO:12 and also has at least 85% identity to SEQ ID NO:14.

A nucleic acid molecule as provided herein in various examples can include a nucleic acid sequence having at least 85% identity to SEQ ID NO:5; SEQ ID NO:6; SEQ ID NO:7; SEQ ID NO:11; or SEQ ID NO:12, juxtaposed with a heterologous nucleic acid sequence, e.g., juxtaposed with a nucleic acid sequence not derived from the rDNA region of the genome of an organism, such as the rDNA region of the genome of *Nannochloropsis*.

In another aspect, provided herein are episomal DNA molecules (EDMs) that include an ARS having at least 85% identity to at least 150 contiguous nucleotides of SEQ ID NO:1; at least 150 contiguous nucleotides of SEQ ID NO:5; at least 150 contiguous nucleotides of SEQ ID NO:6; at least 150 contiguous nucleotides of SEQ ID NO:7; at least 150 contiguous nucleotides of SEQ ID NO: 8; at least 150 contiguous nucleotides of SEQ ID NO:9; at least 150 contiguous nucleotides of SEQ ID NO:10; at least 150 contiguous nucleotides of SEQ ID NO:11; or at least 150 contiguous nucleotides of SEQ ID NO:12. For example, an EDM as provided herein can include an ARS having at least 90%, at least 95%, at least 96%, at least 97%, at least 98%, at least 99%, or 100% identity to at least 150 contiguous nucleotides of SEQ ID NO:1; at least 150 contiguous nucleotides of SEQ ID NO:5; at least 150 contiguous nucleotides of SEQ ID NO:6; at least 150 contiguous nucleotides of SEQ ID NO:7; at least 150 contiguous nucleotides of SEQ ID NO:8; at least 150 contiguous nucleotides of SEQ ID NO:9; at least 150 contiguous nucleotides of SEQ ID NO:10; at least 150 contiguous nucleotides of SEQ ID NO:11; or at least 150 contiguous nucleotides of SEQ ID NO:12. An EDM as provided herein can be circular. The EDM can replicate autonomously in a eukaryotic host cell, such as a cell of a microorganism, such as, for example, a fungal, heterokont, or algal cell.

In various examples, an EDM as provided herein can include an ARS having at least 85%, at least 90%, at least 95%, at least 96%, at least 97%, at least 98%, at least 99%, or 100% identity at least 200, at least 250, at least 300, at least 350, at least 400, at least 450, at least 500, at least 600, at least 700, or at least 750 contiguous nucleotides of SEQ ID NO:1, SEQ ID NO:5, SEQ ID NO:6, SEQ ID NO:7, SEQ ID NO:8, SEQ ID NO:9, SEQ ID NO:10, SEQ ID NO:11, or SEQ ID NO:12. For example, an EDM as provided herein can include an ARS having at least 85%, at least 90%, at least 95%, at least 96%, at least 97%, at least 98%, at least 99%, or 100% identity at least 200, at least 250, at least 300, at least 350, at least 400, at least 450, at least 500, at least 600, at least 700, or at least 750 contiguous nucleotides of SEQ ID NO:1, SEQ ID NO:5, SEQ ID NO:6, SEQ ID NO:7, SEQ ID NO:10, or SEQ ID NO:12. In various examples, an EDM as provided herein can include an ARS having the sequence of SEQ ID NO:1, SEQ ID NO:5, SEQ ID NO:6, SEQ ID NO:7, SEQ ID NO:10, or SEQ ID NO:12.

An EDM as provided herein can further comprise a nucleic acid sequence encoding a polypeptide. For example, an EDM can include a nucleic acid sequence encoding a reporter protein, such as a fluorescent protein or signal-producing enzyme, or selectable marker protein, such as a protein that confers resistance to a drug, antibiotic, toxin, or herbicide or a protein that allows autotrophic growth on stringent media.

Alternatively or in addition, an EDM as provided herein can include a gene encoding a metabolic enzyme, structural protein, kinase, phosphatase, nucleotide cyclase, phosphodiesterase, transcriptional regulator, transcriptional activator, transporter, secretory protein, ion channel, receptor, photosynthetic protein, chaperonin, ribosomal protein, or nuclear scaffold protein. In various examples, an EDM as provided herein can include a gene encoding a meganuclease, a zinc finger nuclease, a TALEN protein, a cas protein, a recombinase, a topoisomerase, or a transposase.

Further alternatively or additionally, an EDM as provided herein can comprise a nucleic acid sequence encoding a functional RNA, such as, for example, an interfering RNA or a precursor thereof, an antisense RNA, a ribozyme, a micro RNA, or a guide RNA of a CRISPR system. Preferably, the functional RNA is not a ribosomal RNA. In various examples, the functional RNA can be a functional RNA designed to attenuate expression of a targeted gene.

In further examples, alternatively or in addition to any of the above, an EDM can include sequences for mediating homologous or site specific recombination, wherein the sequences for homologous recombination include genomic sequences that flank or comprise at least a portion of a gene targeted for gene replacement or disruption, or can include sequences recognized by site-specific recombination systems.

In another aspect of the invention, methods are provided for propagating a gene of interest through at least 8 generations of cell division, in which the method includes incorporating the gene of interest into an EDM as provided herein, transforming the EDM into a host cell, and propagating the host cell for at least 8 generations. In exemplary embodiments, the EDM includes a selectable marker gene, and the host cell is propagated under selection. The host cell can be, in various examples, an algal, heterokont, plant, animal, fungal, or yeast cell, and may be a diatom or Eustigmatophyte cell, for example, a *Nannochloropsis* cell.

In yet another aspect of the invention, methods are provided for expressing a gene or sequence of interest in a host cell, comprising transforming an EDM as provided herein that includes a gene or sequence of interest into a host cell and culturing the host cell under conditions in which the gene or sequence is expressed. In exemplary embodiments the EDM includes a selectable marker gene in addition to the gene or sequence of interest, and the host cell is cultured in the presence of a selective agent for one or more generations. In some examples, the method is for transiently expressing the gene or sequence of interest in a host strain. For example, the host cell transformed with the EDM may be cultured in the presence of the selective agent for one or more generations during which the gene or sequence of interest is expressed, and subsequently cultured in the absence of the selective agent for one or more additional generations, during or after which the gene or sequence of interest is not expressed.

In yet a further aspect a method is provided for isolating an autonomous replication sequence (ARS) in a species of interest, in which the method includes sequencing an sequence amplified from a region of the species' genome between 35S ribosomal DNA (rDNA) repeats and a 28S rDNA repeat; and selecting a portion of the amplified sequence with the lowest percentage guanidine/cytosine content, in which the selected portion is at least 100 nucleotides, at least 200 nucleotides, at least 500 nucleotides, or at least 700 nucleotides in length. The method can further include testing the ARS for the ability to support replication of an EDM in a host cell. Also provided herein are methods for effecting homologous recombination in a host cell of interest, in which the method includes introducing an EDM that includes a selectable marker and a construct for homologous recombination into a host cell.

BRIEF DESCRIPTION OF THE DRAWINGS

FIG. 2 shows an alignment of portions of putative ARSs isolated from *Nannochloropsis gaditana*. The aligned ARSs are, from top to bottom: NgARS1 (SEQ ID NO:5), NgARS3 (SEQ ID NO:7), NgARS5 (SEQ ID NO:9), NgARS4 (SEQ ID NO:8), NgARS2 (SEQ ID NO:6), NgARS7 (SEQ ID NO:10), NgARS7 (SEQ ID NO:10), and NgARS8 (SEQ ID NO:11).

FIG. 8 is a graph showing that *Nannochloropsis* lines transformed with an EDM that included NgARS2 retained the EDM when maintained under blasticidin selection, as evaluated by the expression of the GFP protein, and lost expression of the GFP protein when blasticidin selection was removed.

DETAILED DESCRIPTION

Definitions

Figure 1:
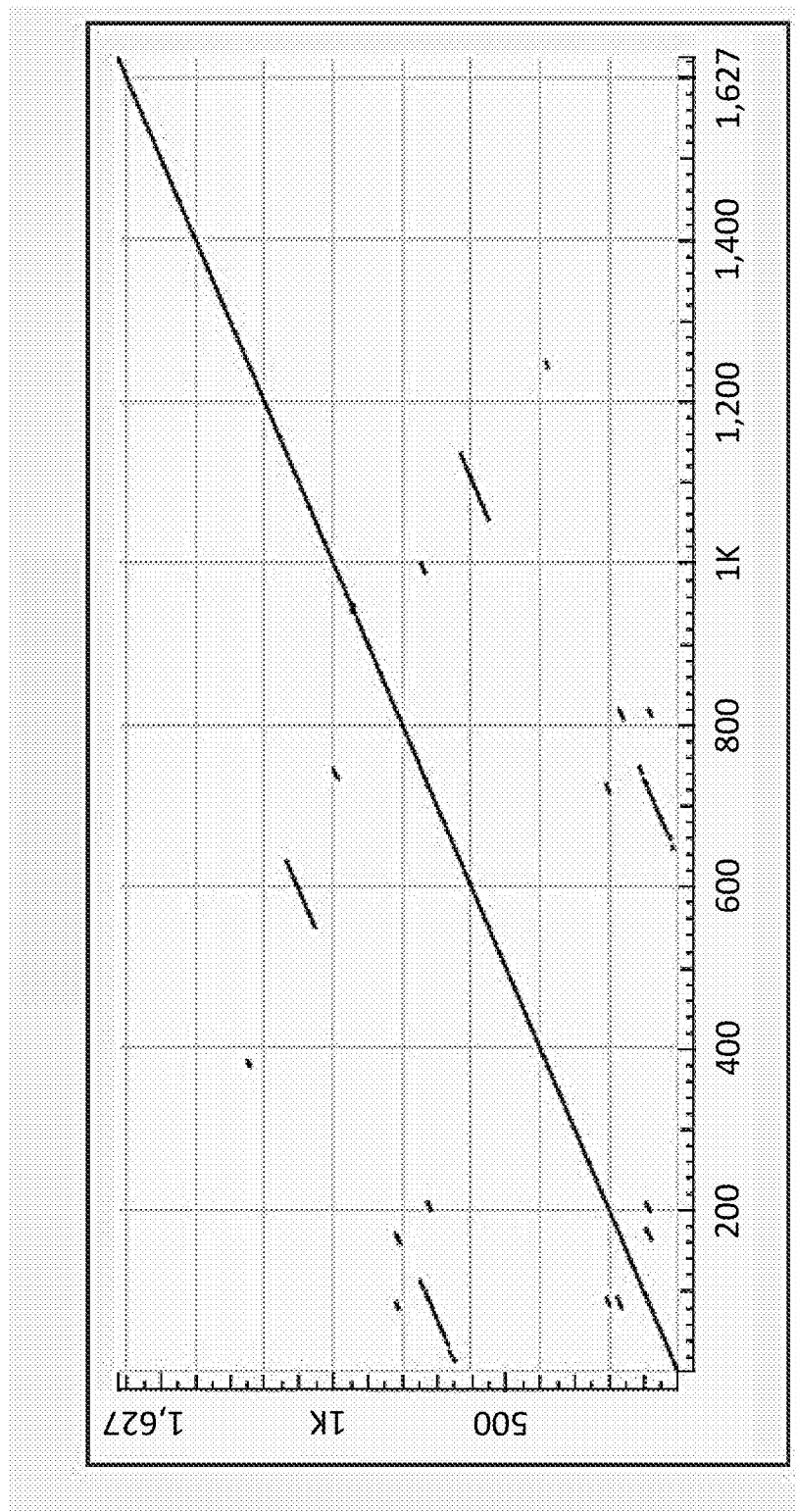
FIG. 1 is a graph depicting a BLAST alignment of regions from the *Nannochloropsis* sp. putative ARS elements. The minor lines in parallel of the major diagonal line are indicative of tandem repeats. An inverted repeat would appear at a 90 degree angle to the major diagonal line.

Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those skilled in the art.

The singular form "a", "an", and "the" include plural references unless the context clearly dictates otherwise. For example, the term "a cell" includes one or more cells, including mixtures thereof. "A and/or B" is used herein to include all of the following alternatives: "A", "B", and "A and B".

"About" means within plus or minus 10% of the provided value, inclusive of the provided value. Where ranges are provided, they are inclusive of the boundary values.

As used herein, "amino acid" refers to naturally-occurring and synthetic amino acids, as well as amino acid analogs and amino acid mimetics that function in a manner similar to the naturally-occurring amino acids. Naturally-occurring amino acids are those encoded by the genetic code, including D/L optical isomers, as well as those amino acids that are later modified, e.g., hydroxyproline, y-carboxyglutamate, and O-phosphoserine. Amino acid analogs refer to compounds that have the same basic chemical structure as a naturally-occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally-occurring amino acid. Amino acid mimetics, as used herein, refer to chemical compounds that have a structure that is different from the general chemical structure of an amino acid, but that functions in a manner similar to a naturally-occurring amino acid.

An "Autonomously Replicating Sequence" or "ARS", sometimes referred to as an "Autonomous Replication Sequence" is a sequence that serves as an origin of DNA replication on eukaryotic chromosomes. An ARS, when incorporated into a DNA molecule, supports replication of the DNA molecule by binding a protein complex that unwinds and replicates the DNA. An ARS can be confirmed (functionally validated) by incorporating the sequence into a DNA molecule that is not self-replicating in a given host and demonstrating that the DNA molecule replicates autonomously in the host only when the ARS is present.

A "nucleic acid construct", "DNA construct" or simply "construct" is a nucleic acid molecule produced by recombinant means that includes at least two operably linked nucleic acid sequences that are not operably linked to one another in nature.

An "episomal DNA molecule" or "EDM" is an independently replicating nucleic acid molecule that is not integrated into the genome of the host organism in which the EDM resides and replicates. An EDM may be stable, in which it persists for many generations or unstable, where the EDM is gradually diluted out of the population by successive cell divisions. A stable EDM may be maintained in a cell population by selective pressure (e.g., the presence of an antibiotic).

A "detectable marker" is a gene or the polypeptide encoded by the gene that confers some detectable phenotype on a cell that expresses the gene. Detection can be colorometric (for example, the blue color by expression of beta galactosidease or beta-glucorinidase in the present of a colorometric substrate) or by detection of luminescence or fluorescence. A detectable marker generally encodes a detectable polypeptide, for example, a green fluorescent protein or a signal producing enzyme such as luciferase, which, when contacted with an appropriate agent (a particular, wavelength of light or luciferin, respectively) generates a signal that can be detected by eye or using appropriate instrumentation (Giacomin, *Plant Sci.* 116:59-72, 1996; Scikantha, J. Bacteriol. 178:121, 1996; Gerdes, *FEBS Lett.* 389:44-47, 1996; see, also, Jefferson, *EMBO J.* 6:3901-3907, 1997, fl-glucuronidase).

The term or "selectable marker" or "selection marker" refers to a gene (or the encoded polypeptide) that confers a phenotype that allow the organism expressing the gene to survive under selective conditions. For example, a selectable marker generally is a molecule that, when present or expressed in a cell, provides a selective advantage (or disadvantage) to the cell containing the marker, for example, the ability to grow in the presence of an agent that otherwise would kill the cell, or the ability to grow in the absence of a particular nutrient.

A "cDNA" is a DNA molecule that comprises at least a portion the nucleotide sequence of an mRNA molecule, with the exception that the DNA molecule substitutes the nucleobase thymine, or T, in place of uridine, or U, occurring in the mRNA sequence. A cDNA can be single-stranded or double-stranded, and can be the complement of the mRNA sequence. In preferred embodiments, a cDNA does not include one or more intron sequences that occur in the naturally-occurring gene (in the genome of an organism) that the cDNA corresponds to. For example, a cDNA can have sequences from upstream (5') of an intron of a naturally-occurring gene juxtaposed to sequences downstream (3') of the intron of the naturally-occurring gene, where the upstream and downstream sequences are not juxtaposed in a DNA molecule (i.e., the naturally occurring gene) in nature. A cDNA can be produced by reverse transcription of mRNA molecules by a polymerase (e.g., a reverse transcriptase), or can be synthesized, for example, by chemical synthesis and/or by using one or more restriction enzymes, one or more ligases, one or more polymerases (including, but not limited to, high temperature tolerant polymerases that can be used in polymerase chain reactions (PCRs)), one or more recombinases, etc., based on knowledge of the cDNA sequence, where the knowledge of the cDNA sequence can optionally be based on the identification of coding regions from genome sequences or compiled from the sequences of multiple partial cDNAs.

A "coding sequence" or "coding region", as used herein in reference to an mRNA or DNA molecule, refers to the portion of the mRNA or DNA molecule that codes for a polypeptide. It typically consists of the nucleotide residues of the molecule which are matched with an anticodon region of a transfer RNA molecule during translation of the mRNA molecule or which encode a stop codon. The coding sequence may thus include nucleotide residues corresponding to amino acid residues which are not present in the mature protein encoded by the mRNA molecule (e.g., amino acid residues in a protein export signal sequence).

"Down-regulation" refers to regulation that decreases production of expression products (mRNA, polypeptide, biological activity, or combinations of any thereof) relative to basal or native states.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting there from. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

The term "endogenous," within the context of the present disclosure refers to any polynucleotide, polypeptide or protein sequence which is a natural part of a cell or organism.

"Exogenous" with respect to a nucleic acid or gene indicates that the nucleic acid or gene is part of a recombinant nucleic acid construct and is not in its natural environment. For example, an exogenous nucleic acid or gene is from one species and has been introduced ("transformed") into another organism, microorganism, or cell by human intervention. Typically, such an exogenous nucleic acid or gene into a cell or organism via a recombinant nucleic acid construct. An exogenous nucleic acid can be a sequence from one species introduced into another species, i.e., a heterologous nucleic acid. An exogenous nucleic acid can also be a sequence that is native or endogenous to an organism (i.e., the nucleic acid sequence occurs naturally in that species or encodes a polypeptide that occurs naturally in the host species) and that has been reintroduced into cells of that organism. An exogenous nucleic acid that includes an endogenous sequence can often be distinguished from the naturally-occurring sequence by the presence of non-natural sequences linked to the exogenous nucleic acid, e.g., non-native regulatory sequences flanking an endogenous gene sequence in a recombinant nucleic acid construct. Alternatively or in addition, a stably transformed exogenous nucleic acid can be detected or distinguished from a native gene by its juxtaposition to sequences in the genome where it has integrated. A nucleic acid is considered exogenous if it has been introduced into a progenitor of the cell, organism, or strain under consideration.

As used herein, "expression" refers to the process of converting genetic information of a polynucleotide into RNA through transcription, which is typically catalyzed by an enzyme, RNA polymerase, and into protein, through translation of mRNA on ribosomes.

"Expression cassette" as used herein means a DNA sequence capable of directing expression of a particular nucleotide sequence in an appropriate host cell, comprising a promoter operably linked to a nucleotide sequence of interest, which is—optionally—operably linked to termination signals and/or other regulatory elements. An expression cassette may also comprise sequences required for proper translation of the nucleotide sequence. The coding region usually codes for a protein of interest but may also code for a functional RNA of interest, for example antisense RNA or a non-translated RNA, in the sense or antisense direction. The expression cassette comprising the nucleotide sequence of interest may be chimeric, meaning that at least one of its components is heterologous with respect to at least one of its other components. The expression cassette may also be one, which is naturally occurring but has been obtained in a recombinant form useful for heterologous expression. An expression cassette may be assembled entirely extra-cellularly (e.g., by recombinant cloning techniques). However, an expression cassette may also be assembled using in part endogenous components. For example, an expression cassette may be obtained by placing (or inserting) a promoter sequence upstream of an endogenous sequence, which thereby becomes functionally linked and controlled by said promoter sequences. The expression of the nucleotide sequence in the expression cassette may be under the control of a constitutive promoter or of an inducible promoter which initiates transcription only when the host cell is exposed to some particular external stimulus.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Examples of expression vectors known in the art include cosmids, plasmids (e.g., naked or contained in liposomes) and viruses (e.g., retroviruses, lentiviruses, adenoviruses, and adeno-associated viruses) that incorporate the recombinant polynucleotide.

"Fragment", as applied to a nucleic acid, refers to a clone or any part of a polynucleotide molecule that retains a usable, functional characteristic. Useful fragments include oligonucleotides and polynucleotides that may be used in hybridization or amplification technologies or in the regulation of replication, transcription or translation. In the context of the present disclosure, a fragment may ordinarily be any subsequence of a nucleic acid, typically of at least about 9 consecutive nucleotides, at least about 12 consecutive nucleotides, at least about 14 consecutive nucleotides, at least about 16 consecutive nucleotides, more typically from about 10 to 18 consecutive nucleotides, typically from at least about 12 to 16 consecutives nucleotides, even more typically from at least about 10 to 16 consecutive nucleotides, of any one of the nucleotide sequences provided herein in the Sequence Listing.

An "oligonucleotide", as used herein, is a nucleic acid molecule 200 or fewer nucleotides in length. An oligonucleotide can be RNA, DNA, or a combination of DNA and RNA, a nucleic acid derivative, or a synthetic nucleic acid, for example, an oligonucleotide can be a peptide nucleic acid or a locked nucleic acid, and can be single-stranded, double-stranded, or partially single-stranded and partially double-stranded. An oligonucleotide can be, for example, between about 4 and about 200 nucleotides in length, between about 6 and about 200 nucleotides in length, between about 10 and about 200 nucleotides in length, between about 15 and about 200 nucleotides in length, between about 17 and about 200 nucleotides in length, between about 20 and about 200 nucleotides in length, or between about 40 and about 200 nucleotides in length. In additional examples, an oligonucleotide can be between about 15 and about 180 nucleotides in length, between about 15 and about 160 nucleotides in length, between about 15 and about 140 nucleotides in length, between about 15 and about 120 nucleotides in length, between about 17 and about 100 nucleotides in length, between about 17 and about 80 nucleotides in length, or between about 17 and about 70 nucleotides in length, for example between about 20 and about 65 nucleotides in length.

When used in reference to a polynucleotide, a gene, a nucleic acid, a polypeptide, or an enzyme, the term "heterologous" refers to a polynucleotide, gene, a nucleic acid, polypeptide, or an enzyme not derived from the host species, e.g., is from a different species with respect to the host cell. For example, a transgenic *Nannochloropsis* microorganism transformed with the coding sequence for a fatty acid desaturase from a *Tetraselmis* microorganism or from a plant is transformed with a heterologous desaturase gene. When referring to nucleic acid sequences operably linked or otherwise joined to one another ("juxtaposed") in a nucleic acid construct or molecule, "heterologous sequences", as used herein, are those that are not operably linked or are not in proximity or contiguous to each other in nature. As such, elements operably linked or contiguous to each other in nature are not heterologous to each other. For example, a promoter from *Tetraselmis* sp. is considered heterologous to a *Nannochloropsis* coding region sequence. Also, a promoter from a gene encoding a tubulin gene from *Nannochloropsis* is considered heterologous to a sequence encoding a *Nannochloropsis* fatty acid desaturase. Similarly, when referring to a gene regulatory sequence or to an auxiliary nucleic acid sequence used for maintaining or manipulating a gene sequence (e.g. a 5' un-translated region, 3' un-translated region, Kozak sequence, poly A addition sequence, intron sequence, splice site, ribosome binding site, internal ribosome entry sequence, genome homology region, recombination site, etc.), "heterologous" means that the regulatory sequence or auxiliary sequence is from a different source (e.g., different gene, whether from the same or different species as the host organisms) than the gene with which the regulatory or auxiliary nucleic acid sequence is juxtaposed in a construct, genome, chromosome, or episome.

The term "hybridization", as used herein, refers generally to the ability of nucleic acid molecules to join via complementary base strand pairing. Such hybridization may occur when nucleic acid molecules are contacted under appropriate conditions and/or circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, nucleic acid molecules are said to exhibit "complete complementarity" when every nucleotide of one of the molecules is complementary to its base pairing partner nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional stringency conditions are described by Sambrook et al., 1989, supra), and by Haymes et al. In: *Nucleic Acid Hybridization, A Practical Approach*, IRL Press, Washington, D.C. (1985). Departures from complete complementarity are therefore permissible, as long as such departures do not completely preclude the capacity of the molecules to form a double-stranded structure. Thus, in order for a nucleic acid molecule or fragment thereof of the present invention to serve as a primer or probe it needs only be sufficiently complementary in sequence to be able to form a stable double-stranded structure under the particular solvent and salt concentrations employed.

Appropriate stringency conditions which promote DNA hybridization include, for example, 6.0× sodium chloride/sodium citrate (SSC) at about 45° C., followed by a wash of 2.0×SSC at about 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. These conditions are known to those skilled in the art, or can be found in *Current Protocols in Molecular Biology*, John Wiley & Sons, N.Y. (1989), 6.3.1-6.3.6. For example, low stringency conditions may be used to select nucleic acid sequences with lower sequence identities to a target nucleic acid sequence. One may wish to employ conditions such as about 0.15 M to about 0.9 M sodium chloride, at temperatures ranging from about 20° C. to about 55° C. High stringency conditions may be used to select for nucleic acid sequences with higher degrees of identity to the disclosed nucleic acid sequences (Sambrook et al., 1989, supra). In one embodiment of the present invention, high stringency conditions involve nucleic acid hybridization in about 2×SSC to about 10×SSC (diluted from a 20×SSC stock solution containing 3 M sodium chloride and 0.3 M sodium citrate, pH 7.0 in distilled water), about 2.5× to about 5×Denhardt's solution (diluted from a 50× stock solution containing 1% (w/v) bovine serum albumin, 1% (w/v) ficoll, and 1% (w/v) polyvinylpyrrolidone in distilled water), about 10 mg/mL to about 100 mg/mL fish sperm DNA, and about 0.02% (w/v) to about 0.1% (w/v) SDS, with an incubation at about 50° C. to about 70° C. for several hours to overnight. High stringency conditions are typically provided by 6×SSC, 5×Denhardt's solution, 100 mg/mL fish sperm DNA, and 0.1% (w/v) SDS, with incubation at 55×C for several hours. Hybridization is generally followed by several wash steps. The wash compositions generally comprise 0.5×SSC to about 10×SSC, and 0.01% (w/v) to about 0.5% (w/v) SDS with an incubation for 15-min at about 20° C. to about 70° C. Typically, the nucleic acid segments remain hybridized after washing at least one time in 0.1×SSC at 65° C.

"Percentage of sequence identity," as used herein, is determined by comparing two optimally locally aligned sequences over a comparison window defined by the length of the local alignment between the two sequences. The amino acid sequence in the comparison window may comprise additions or deletions (e.g., gaps or overhangs) as compared to the reference sequence (which does not comprise additions or deletions) for optimal alignment of the two sequences. Local alignment between two sequences only includes segments of each sequence that are deemed to be sufficiently similar according to a criterion that depends on the algorithm used to perform the alignment (e.g. BLAST). The percentage identity is calculated by determining the number of positions at which the identical nucleic acid base or amino acid residue occurs in both sequences to yield the number of matched positions, dividing the number of matched positions by the total number of positions in the window of comparison and multiplying the result by 100. Optimal alignment of sequences for comparison may be conducted by the local homology algorithm of Smith and Waterman (*Add. APL. Math.* 2:482, 1981), by the global homology alignment algorithm of Needleman and Wunsch (*J. Mol. Biol.* 48:443, 1970), by the search for similarity method of Pearson and Lipman (*Proc. Natl. Acad. Sci. USA* 85: 2444, 1988), by heuristic implementations of these algorithms (NCBI BLAST, WU-BLAST, BLAT, SIM, BLASTZ), or by inspection. GAP and BESTFIT, for example, can be employed to determine their optimal alignment of two sequences that have been identified for comparison. Typically, the default values of 5.00 for gap weight and 0.30 for gap weight length are used. The term "substantial sequence identity" between polynucleotide or polypeptide sequences refers to polynucleotide or polypeptide comprising a sequence that has at least 50% sequence identity, for example, at least 70%, at least 80%, at least 85%, at least 90%, at least 95%, or at least 96%, 97%, 98% or 99% sequence identity compared to a reference sequence using the programs. In addition, pairwise sequence homology or sequence similarity, as used refers to the percentage of residues that are similar between two sequences aligned. Families of amino acid residues having similar side chains have been well defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

For example, query nucleic acid and amino acid sequences can be searched against subject nucleic acid or amino acid sequences residing in public or proprietary databases. Such searches can be done using the National Center for Biotechnology Information Basic Local Alignment Search Tool (NCBI BLAST v 2.18) program. The NCBI BLAST program is available on the interne from the National Center for Biotechnology Information (blast.ncbi.nlm.nih.gov/Blast.cgi). Exemplary parameters for NCBI BLAST include: Filter options set at "default", the Comparison Matrix set to "BLOSUM62", the Gap Costs set to "Existence: 11, Extension: 1", the Word Size set to 3, the Expect (E threshold) set to 1e-3, and the minimum length of the local alignment set to 50% of the query sequence length. Sequence identity and similarity may also be determined using GENOMEQUEST™ software (Gene-IT, Worcester, Mass. USA).

As used herein, an "isolated" nucleic acid or protein is removed from its natural milieu or the context in which the nucleic acid or protein exists in nature. For example, an isolated protein or nucleic acid molecule is removed from the cell or organism with which it is associated in its native or natural environment. As such, an "isolated" nucleic acid typically is free of sequences that naturally flank the nucleic acid (i.e., sequences located at the 5' and 3' ends of the nucleic acid) in the cell of the organism from which the nucleic acid is derived. An isolated nucleic acid or protein can be, in some instances, partially or substantially purified, but no particular level of purification is required for isolation. For example, an isolated nucleic acid molecule can be a nucleic acid sequence that has been excised from the chromosome, genome, or episome that it is integrated into in nature. Thus, an isolated nucleic acid includes, without limitation, a nucleic acid that exists as a purified molecule, or a nucleic acid molecule that is incorporated into a vector or a recombinant cell.

A "purified" nucleic acid molecule or nucleotide sequence is substantially free of cellular material and cellular components. The purified nucleic acid molecule may be free of chemicals beyond buffer or solvent, for example. "Substantially free" is not intended to mean that other components beyond the novel nucleic acid molecules are undetectable. In some circumstances "substantially free" may mean that the nucleic acid molecule or nucleotide sequence is free of at least 95% (w/w) of cellular material and components.

The term "mis-expression" refers to an increase or decrease in the transcription of a coding region into a complementary RNA sequence as compared to the parental wild-type, for example, alga or plant. This term also encompasses expression of a gene or coding region for a different time period as compared to the wild-type and/or from a non-natural location within the parental genome. The term "overexpression" or "increased expression" as used herein refers to a greater expression level of a gene, a polynucleotide sequence, or a polypeptide, in a host cell compared to a wild-type cell or a wild-type organism, at any developmental or temporal stage. Methods for increasing expression of genes or gene products are well documented in the art and include, for example, overexpression driven by appropriate promoters (e.g. constitutive promoters), the use of transcription enhancers or translation enhancers. Overexpression may also under control of an inducible or a growth-phase specific promoter. These or other inducible or phase-specific promoters may be incorporated into an expression cassette comprising a transcription factor polynucleotide of the invention, where the promoter is operably linked to the transcription factor polynucleotide, can be envisioned and produced. Thus, overexpression may occur throughout an algal cell for example, in specific growth phases of the algal cell or in the presence or absence of particular environmental signals, depending on the promoter used.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome, or genes endogenous to the host organism that are in a locus of the genome other than that where they naturally occur.

In reference to a nucleic acid molecule or a polypeptide, the term's "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

The term's "nucleic acid molecule" and "polynucleotide molecule" are used interchangeably herein, and refer to both DNA and RNA molecule, including cDNA, genomic DNA, synthetic DNA, and DNA or RNA containing nucleic acid analogs. Polynucleotides can have any three-dimensional structure. Polynucleotides can be natural-occurring or synthetic origin. A nucleic acid molecule can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

As used herein, "operably linked" is intended to mean a functional linkage between two or more sequences such that activity at or on one sequence affects activity at or on the other sequence(s). For example, an operable linkage between a polynucleotide of interest and a regulatory sequence (e.g., a promoter) is a functional link that allows for expression of the polynucleotide of interest. In this sense, the tend "operably linked" refers to the positioning of a regulatory region and a coding sequence to be transcribed so that the regulatory region is effective for regulating transcription or translation of the coding sequence of interest. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site. Operably linked elements may be contiguous or non-contiguous. When used to refer to the joining of two protein coding regions, by "operably linked" is intended that the coding regions are in the same reading frame. When used to refer to the effect of an enhancer, "operably linked" indicated that the enhancer increases the expression of a particular polypeptide or polynucleotides of interest. "Juxtaposed with" in the context of nucleic acid sequences, means the referenced sequences are part of the same continuous nucleic acid molecule.

The tends "polynucleotide sequence" and "nucleic acid sequence" as used herein interchangeably refer to a sequence of a polynucleotide molecule, and can refer, for example, to DNA or RNA sequences. The nomenclature for nucleotide bases as set forth in 37 CFR §1.822 is used herein.

A "promoter" refers to a transcription control sequence that is capable of initiating transcription in a host cell and can drive or facilitate transcription of a nucleotide sequence or fragment thereof of the instant invention. Such promoters need not be of naturally-occurring sequences. In addition, it will be understood that such promoters need not be derived from the target host cell or host organism.

"Polypeptide" and "protein" are used interchangeably herein and refer to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition. In various embodiments the polypeptides can have at least 10 amino acids or at least 25, or at least 50 or at least 75 or at least 100 or at least 125 or at least 150 or at least 175 or at least 200 amino acids.

As used herein "progeny" means a descendant, offspring, or derivative of an organism. For example, daughter cells from a transgenic alga are progeny of the transgenic alga. Because certain modifications may occur in succeeding generations due to mutations or environmental influences, such progeny, descendant, or derivatives may not, in fact, be identical to the parent cell, but are still included within the scope of the term as used herein.

The terms "recombinant" or "engineered" as used herein in reference to a nucleic acid molecule, refer to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence.

The term "recombinant protein" as used herein refers to a protein produced by genetic engineering, for example, by expression of a genetically engineered nucleic acid molecule in a cell.

The term "regulatory region" "regulatory sequence", "regulatory element", or "regulatory element sequence", as used in the present invention, refer to a nucleotide sequence that influences transcription or translation initiation or rate, and stability and/or mobility of a transcription or translation product. Such regulatory regions need not be of naturally-occurring sequences. Regulatory sequences include but are not limited to promoter sequences, enhancer sequences, response elements, protein recognition sites, inducible elements, protein binding sequences, 5' and 3' un-translated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR).

As used herein, "transgenic organism" refers to an organism which comprises a heterologous polynucleotide. When applied to organisms, the terms "transgenic" or "recombinant" or "engineered" or "genetically engineered," used interchangeably herein, refer to organisms that have been manipulated by introduction into the organism of an exogenous or recombinant nucleic acid sequence. Generally, the heterologous polynucleotide is stably integrated within the genome such that the polynucleotide is passed on to successive generations, although it can also be present on an episome, and may be present on a synthetic chromosome of the transgenic organism. The non-native polynucleotide may be integrated into the genome alone or as part of a recombinant expression cassette. In additional examples, a transgenic microorganism can include an introduced exogenous regulatory sequence operably linked to an endogenous gene of the transgenic microorganism. Non-limiting examples of such manipulations include gene knockouts, targeted mutations and gene replacement, promoter replacement, deletion, or insertion, as well as introduction of transgenes into the organism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases, zinc finger nucleases, or Crisper nucleases. As used herein, "recombinant microorganism" or "recombinant host cell" includes progeny or derivatives of the recombinant microorganisms of the invention. Because certain modifications may occur in succeeding generations from either mutation or environmental influences, such progeny or derivatives may not, in fact, be identical to the parent cell, but are still included within the scope of the term as used herein.

For nucleic acids and polypeptides, the term "variant" is used herein to denote a polypeptide, protein, or polynucleotide molecule with some differences, generated synthetically or naturally, in their base or amino acid sequences as compared to a reference polypeptide or polynucleotide, respectively, such that the variant has at least 70% sequence identity with the reference polypeptide or polynucleotide. In other embodiments the variant can have at least 80% or at least 90% or at least 95% or at least 97% or at least 98% or at least 99% sequence identity with the reference polypeptide or polynucleotide. For example, these differences include substitutions, insertions, deletions or any desired combinations of such changes in a reference polypeptide or polypeptide. Polypeptide and protein variants can further consist of changes in charge and/or post-translational modifications (such as glycosylation, methylation. phosphorylation, etc.). When the term "variant" is used in reference to a microorganism, it typically refers to a strain microbial strain having identifying characteristics of the species to which it belongs, while having at least one nucleotide sequence variation or identifiably different trait with respect to the parental strain, where the trait is genetically based (heritable). For example, for a *Nannochloropsis* strain, identifiable traits include the lack of chlorophyll b and c, which is different from other related microalgae.

A "vector" is any genetic element capable of serving as a vehicle of genetic transfer, expression, or replication for a foreign polynucleotide in a host cell. For example, a vector may be an artificial chromosome or a plasmid, and may be capable of stable integration into a host cell genome, or it may exist as an independent genetic element (e.g., episome, plasmid). A vector may exist as a single polynucleotide or as two or more separate polynucleotides. Vectors may be single copy vectors or multicopy vectors when present in a host cell. Preferred vectors for use in the present invention are expression vector molecules in which one or more functional genes can be inserted into the vector molecule, in proper orientation and proximity to expression control elements resident in the expression vector molecule so as to direct expression of one or more proteins when the vector molecule resides in an appropriate (e.g. homologous) host cell.

All publications and patent applications mentioned in this specification are herein incorporated by reference to the same extent as if each individual publication or patent application was specifically and individually indicated to be incorporated by reference.

No admission is made that any reference constitutes prior art. The discussion of the references states what their authors assert, and the applicants reserve the right to challenge the accuracy and pertinence of the cited documents. It will be clearly understood that, although a number of prior art publications are referred to herein; this reference does not constitute an admission that any of these documents forms part of the common general knowledge in the art.

The discussion of the general methods given herein is intended for illustrative purposes only. Other alternative methods and embodiments will be apparent to those of skill in the art upon review of this disclosure.

Autonomously Replicating Sequences (ARSs)

The invention provides ARSs isolated from the heterokont (stramenopile) alga *Nannochloropsis*.

In a first aspect, provided herein is an isolated or recombinant nucleic acid molecule that includes an ARS, in which the ARS includes a nucleic acid sequence having at least 85% identity to SEQ ID NO:13 or SEQ ID NO:14. The ARS can be juxtaposed with or adjacent to at least one heterologous nucleic acid sequence, i.e., a sequence not juxtaposed with or adjacent to the ARS in the genomic of the organism from which the ARS is derived. In some examples, provided herein is a nucleic acid molecule that includes an ARS having a nucleic acid sequence with at least 85% identity to SEQ ID NO:13 or SEQ ID NO:14 that also includes one or more nucleic acid sequence s that are not derived from the organism from with the ARS is derived. For example, an ARS as provided herein can be juxtaposed with or adjacent to a nucleic acid sequence not isolated or derived from an rDNA repeat region of the genome of an organism from which the ARS is derived. In this context, juxtaposed means the ARS is on the same nucleic acid molecule, i.e., is part of the same nucleotide polymer that includes the heterologous sequence. For example an ARS having a nucleic acid sequence having homology to SEQ ID NO:13 or SEQ ID NO:14 can be directly or indirectly linked to a heterologous sequence such as a reporter gene, a selectable marker gene, a gene encoding a polypeptide of interest, or a gene encoding a functional RNA that is preferably not a ribosomal RNA. The nucleic acid sequence having at least 85% identity to SEQ ID NO:13 or SEQ ID NO:14 can have, for example, at least 90%, at least 95%, at least 96%, at least 97%, at least 98%, at least 99%, or 100% identity to SEQ ID NO:13 or SEQ ID NO:14. In some examples, an isolated or recombinant nucleic acid molecule includes a nucleic acid sequence having at least 85% identity to SEQ ID NO:13 and additionally includes a nucleic acid sequence having at least 85% identity to SEQ ID NO:14. The nucleic acid molecule can be a DNA molecule.

An ARS having at least 85% identity to SEQ ID NO:13 or SEQ ID NO:14 can be a naturally-occurring sequence, for example, a nucleic acid sequence isolated from a plant, animal, fungal, algal, or heterokont cell, or can be a variant of a naturally-occurring sequence. For example, an ARS as provided herein can be a naturally-occurring sequence isolated from an algal or heterokont species. Isolated sequences can be tested for ARS function using methods provided herein, and can be truncated to test for ARS function of fragments of reduced size.

An ARS as provided herein is functional in a eukaryotic cell, for example, a microbial cell such as a plant, animal, fungal, algal, or heterokont cell. For example, an ARS as provided herein and may be functional in a diatom or Eustigmatophyte cell, for example, a *Nannochloropsis* cell.

Nonlimiting examples of algal cells in which an ARS as provided herein can be functional include *Amphora, Ankistrodesmus, Aplanochytrium, Asteromonas, Boekelovia, Bolidomonas, Borodinella, Botrydium, Botryococcus, Bracteococcus, Carteria, Chaetoceros, Chlamydomonas, Chlorella, Chlorococcum, Chlorogonium, Chrococcidiopsis, Chroomonas, Chrysophyceae, Chrysosphaera, Colwellia, Cricosphaera, Crypthecodinium, Cryptococcus, Cryptomonas, Cunninghamella, Cyclotella, Desmodesmus, Dunaliella, Elina, Ellipsoidon, Emiliania, Eremosphaera, Ernodesmius, Euglena, Eustigmatos, Fragilaria, Fragilariopsis, Franceia, Gloeothamnion, Haematococcus, Hantzschia, Heterosigma, Hymenomonas, Isochrysis, Japanochytrium, Labrinthula, Labyrinthomyxa, Labyrinthula, Lepocinclis, Micractinium, Monodus, Monoraphidium, Moritella, Mortierella, Mucor, Nannochloris, Nannochloropsis, Navicula, Neochloris, Nephrochloris, Nephroselmis, Nitzschia, Ochromonas, Oedogonium, Oocystis, Ostreococcus, Parachlorella, Parietochloris, Pascheria, Pavlova, Pelagomonas, Phaeodactylum, Phagus, Pichia, Picochlorum, Pithium, Platymonas, Pleurochrysis, Pleurococcus, Porphyridium, Prototheca, Pseudochlorella, Pseudoneochloris, Pseudostaurastrum, Pyramimonas, Pyrobotrys, Rhodosporidium, Scenedesmus, Schizochlamydella, Schizochytrium, Skeletonema, Spirulina, Spyrogyra, Stichococcus, Tetrachlorella, Tetraselmis, Thalassiosira, Thraustochytrium, Tribonema, Ulkenia, Vaucheria, Vibrio, Viridiella, Vischeria,* and *Volvox.*

Heterokont species in which an ARS as disclosed herein may be functional include, but are not limited to, species of the taxonomic groups Bacillariophytes (diatoms), Eustigmatophytes, Labrinthulids, and Thraustochytrids. In some examples, a strain used in the invention may be a species of Labrinthulid or Thraustochytrid such as *Labryinthula, Labiyinthuloides, Thraustochytrium, Schizochytrium, Aplanochytrium, Aurantiochytrium, Japonochytrium, Diplophrys,* or *Ulkenia.*

Exemplary diatoms may include members of the genera *Achnanthes, Amphora, Chaetoceros, Coscinodiscus, Cylindrotheca, Cyclotella, Cymbella, Hantzschia, Navicula, Nitzschia, Pavlova, Pseudo-Nitzschia, Phaeodactylum, Psammodictyon, Skeletonema, Thalassionema,* and *Thallasiosira.* Eustigmatophytes that can be used for genetic modification or nucleic acid isolation include, for example, species of *Eustigmatos, Monodus, Nannochloropsis,* and *Vischeria.* For example, microorganisms for genetic modification or nucleic acid isolation as disclosed herein include members of the genus *Nannochloropsis.* Particularly suitable species include *N. gaditana, N. granulata, N. limnetica, N. maritime, N. oceanica, N. oculata,* and *N. salina.* Preferred species within the genus *Nannochloropsis* include, but are not limited to, *N. gaditana, N. oceanica, N. oculata,* and *N. salina.*

Functionality of an ARS can be tested using the methods provided in the Examples herein, for example, an ARS can be tested by inserting the ARS into a circular vector that includes a selectable marker, and verifying that the circular vector replicates independently (i.e., is an EDM) with, but not without, the ARS. For example, an independently replicating vector having a selectable marker can be tested by isolating uncut DNA from the host grown under selection and demonstrating transformation of *E. coli* with the vector (where the vector also includes an origin of replication and selectable marker functional in *E. coli*), demonstration by gel electrophoresis that the vector is maintained in the host in circular form, and/or demonstration (by PCR or DNA sequencing) that vector sequences are maintained intact in the host.

In some examples, the nucleic acid molecule that includes an ARS that includes a nucleic acid sequence having at least 85% identity to SEQ ID NO:13 is an ARS having at least 85%, at least 90%, at least 95%, at least 96%, at least 97%, at least 98%, at least 99%, or 100% identity to SEQ ID NO:1, SEQ ID NO:5; SEQ ID NO:6; SEQ ID NO:7; SEQ ID NO:8; SEQ ID NO:9; or SEQ ID NO:10. In some examples, the nucleic acid molecule includes an ARS that includes a nucleic acid sequence that has at least 85% identity to SEQ ID NO:14 and has at least 85%, at least 90%, at least 95%, at least 96%, at least 97%, at least 98%, at least 99%, or 100% identity to SEQ ID NO:5; SEQ ID NO:6; SEQ ID NO:7; SEQ ID NO:11; or SEQ ID NO:12.

For example, a nucleic acid molecule as provided herein in various examples can include an ARS having at least 85% or at least 90% identity to SEQ ID NO:5; SEQ ID NO:6; SEQ ID NO:7; SEQ ID NO:11; or SEQ ID NO:12, juxtaposed with a heterologous nucleic acid sequence, e.g., a nucleic acid sequence not derived from the rDNA region of the genome of an organism, such as the rDNA region of the genome of *Nannochloropsis*. In exemplary embodiments, a nucleic acid molecule as provided herein can include an ARS having at least 95%, at least 96%, at least 97%, at least 98%, at least 99%, or 100% identity to SEQ ID NO:5; SEQ ID NO:6; SEQ ID NO:7; SEQ ID NO:11; or SEQ ID NO:12, juxtaposed with a heterologous nucleic acid sequence, e.g., a nucleic acid sequence not derived from the rDNA region of the genome of an organism, such as the rDNA region of the genome of *Nannochloropsis*. In various examples, the ARS has at least 95%, at least 96%, at least 97%, at least 98%, at least 99%, or 100% identity to SEQ ID NO:6.

In another aspect, provided herein are episomal DNA molecules (EDMs) that include an ARS having at least 85% identity to at least 150 contiguous nucleotides of SEQ ID NO:1; at least 150 contiguous nucleotides of SEQ ID NO:5; at least 150 contiguous nucleotides of SEQ ID NO:6; at least 150 contiguous nucleotides of SEQ ID NO:7; at least 150 contiguous nucleotides of SEQ ID NO:8; at least 150 contiguous nucleotides of SEQ ID NO:9; at least 150 contiguous nucleotides of SEQ ID NO:10; at least 150 contiguous nucleotides of SEQ ID NO:11; or at least 150 contiguous nucleotides of SEQ ID NO:12. For example, an EDM as provided herein can include an ARS having at least 90%, at least 95%, at least 96%, at least 97%, at least 98%, at least 99%, or 100% identity to at least 150 contiguous nucleotides of SEQ ID NO:1; at least 150 contiguous nucleotides of SEQ ID NO:5; at least 150 contiguous nucleotides of SEQ ID NO:6; at least 150 contiguous nucleotides of SEQ ID NO:7; at least 150 contiguous nucleotides of SEQ ID NO:8; at least 150 contiguous nucleotides of SEQ ID NO:9; at least 150 contiguous nucleotides of SEQ ID NO:10; at least 150 contiguous nucleotides of SEQ ID NO:11; or at least 150 contiguous nucleotides of SEQ ID NO:12. An EDM as provided herein can be circular. The EDM can further include a selectable marker gene. The EDM can replicate autonomously in a eukaryotic host cell, such as a plant or animal cell or a cell of a microorganism, such as, for example, a fungal, heterokont, or algal cell, including but not limited to those disclosed hereinabove.

In various examples, an EDM as provided herein can include an ARS having at least 85%, at least 90%, at least 95%, at least 96%, at least 97%, at least 98%, at least 99%, or 100% identity to at least 200, at least 250, at least 300, at least 350, at least 400, at least 450, at least 500, at least 600, at least 700, or at least 750 contiguous nucleotides of SEQ ID NO:1, SEQ ID NO:5, SEQ ID NO:6, SEQ ID NO:7, SEQ ID NO:8, SEQ ID NO:9, SEQ ID NO:10, SEQ ID NO:11, or SEQ ID NO:12. For example, an EDM as provided herein can include an ARS having at least 85%, at least 90%, at least 95%, at least 96%, at least 97%, at least 98%, at least 99%, or 100% identity to at least 200, at least 250, at least 300, at least 350, at least 400, at least 450, at least 500, at least 600, at least 700, or at least 750 contiguous nucleotides of SEQ ID NO:1, SEQ ID NO:5, SEQ ID NO:6, SEQ ID NO:7, SEQ ID NO:10, or SEQ ID NO:12. In particular examples, an EDM as provided herein can include an ARS having at least 95%, at least 96%, at least 97%, at least 98%, at least 99%, or 100% identity to at least at least 300, at least 350, at least 400, at least 450, at least 500, at least 600, at least 700, or at least 750 contiguous nucleotides of SEQ ID NO:1, SEQ ID NO:5, SEQ ID NO:6, SEQ ID NO:7, SEQ ID NO:10, or SEQ ID NO:12. In further examples, an EDM as provided herein can include an ARS having at least 95%, at least 96%, at least 97%, at least 98%, at least 99%, or 100% identity to SEQ ID NO:1, SEQ ID NO:5, SEQ ID NO:6, SEQ ID NO:7, SEQ ID NO:10, or SEQ ID NO:12. In yet further examples, an EDM can include the ARS of SEQ ID NO:1, SEQ ID NO:5, SEQ ID NO:6, SEQ ID NO:7, SEQ ID NO:10, or SEQ ID NO:12. For example, provided herein is an EDM comprising the ARS of SEQ ID NO:6.

An EDM as provided herein can further comprise a nucleic acid sequence encoding a polypeptide. For example, an EDM can include a nucleic acid sequence encoding a reporter protein, such as a fluorescent protein or signal-producing enzyme, or a selectable marker protein, such as a protein that confers resistance to a drug, antibiotic, toxin, or herbicide or a protein that allows autotrophic growth on stringent media.

Detectable markers or reporter genes can include genes encoding a variety of fluorescent proteins, including without limitation green, cyan, blue, yellow, and red fluorescent proteins and their variants. Other fluorescent or chromogenic markers that have been used include luciferase (Falciatore et al., *J. Mar. Biotechnol.*, 1: 239-251, 1999; Fuhrmann et al., *Plant Mol. Biol.*, 2004; Jarvis and Brown, *Curr. Genet.*, 19: 317-322, 1991), β-glucuronidase (Chen et al., 2001, supra; Cheney et al., 2001, supra; Chow and Tung, 1999, supra; El-Sheekh, 1999, supra; Falciatore et al., 1999, supra; Kubler et al., *J. Mar. Biotechnol.*, 1:165-169, 1994), β-galactosidase (Gan et al., *J. Appl. Phycol.*, 15:345-349, 2003; Jiang et al., *Plant Cell Rep.*, 21:1211-1216, 2003; Qin et al., *High Technol. Lett.*, 13:87-89, 2003). Further nonlimiting examples of enzymes that can be used for detecting a colored or labeled product include aryl sulfatase and chloramphenicol acetyl transferase.

A selectable marker can provide a means to obtain heterokont cells, algal cells, yeast cell, plant cells or any combination that express the marker and, therefore, include the EDM and can therefor be useful as a component of an EDM of the present disclosure (see, for example, Bock, supra, 2001). Examples of selectable markers include deaminase, such as the deaminase from *Aspergillus terreus*, which confers resistance to Blasticidin S (Tamura, *Biosci. Biotechnol. Biochem.* 59:2336-2338, 1995), as well as genes conferring resistance to antibiotics such as bleomycin, gentamycin, glyphosate, hygromycin, kanamycin, neomycin, phleomycin, puromycin, spectinomycin, and streptomycin. For example, neomycin phosphotransferase confers resistance to the aminoglycosides neomycin, kanamycin and paromycin (Herrera-Estrella, *EMBO J.* 2:987-995, 1983)

and the "hygro" gene confers resistance to hygromycin (Marsh, *Gene* 32:481-485, 1984). Several different antibiotic resistance genes have been used successfully for selection of microalgal transformants, including blastocydin, bleomycin (see, for example, Apt et al., 1996, supra; Fischer et al., 1999, supra; Fuhrmann et al., *Plant J.,* 19, 353-61, 1999, Lumbreras et al., *Plant J.,* 14(4):441-447, 1998; Zaslayskaia et al., *J. Phycol.,* 36:379-386, 2000), spectinomycin (Cerutti et al., *Genetics,* 145: 97-110, 1997; Doetsch et al., *Curr. Genet.,* 39, 49-60, 2001; Fargo, *Mol. Cell. Biol.,* 19:6980-90, 1999), streptomycin (Berthold et al., *Protist,* 153:401-412, 2002), paromomycin (Jakobiak et al., *Protist,* supra.; Sizova et al., *Gene,* 277:221-229, 2001), nourseothricin (Zaslayskaia et al., 2000, supra), G418 (Dunahay et al., 1995, supra; Poulsen and Kroger, *FEBS Lett.,* 272:3413-3423, 2005, Zaslayskaia et al., 2000, supra), hygromycin (Berthold et al., 2002, supra), chloramphenicol (Poulsen and Kroger, 2005, supra), and many others. Additional selectable markers for use in microalgae such as *Chlamydomonas* can be markers that provide resistance to kanamycin and amikacin resistance (Bateman, *Mol. Gen. Genet.* 263:404-10, 2000), zeomycin and phleomycin (e.g., ZEOCIN™ pheomycin D1) resistance (Stevens, *Mol. Gen. Genet.* 251:23-30, 1996), and paramomycin and neomycin resistance (Sizova et al., 2001, supra).

Also considered are genes conferring resistance to antimetabolites such as methotrexate, e.g., genes encoding dihydrofolate reductase, (Reiss, *Plant Physiol.* (Life Sci. Adv.) 13:143-149, 1994); trpB, which allows cells to utilize indole in place of tryptophan; hisD, which allows cells to utilize histinol in place of histidine (Hartman, *Proc. Natl. Acad. Sci.,* USA 85:8047, 1988); mannose-6-phosphate isomerase which allows cells to utilize mannose (WO 94/20627); ornithine decarboxylase, which confers resistance to the ornithine decarboxylase inhibitor, 2-(difluoromethyl)-DL-ornithine (DFMO; McConlogue, 1987, In: *Current Communications in Molecular Biology,* Cold Spring Harbor Laboratory ed.). Additional selectable markers include those that confer herbicide resistance, for example, phosphinothricin acetyltransferase gene, which confers resistance to phosphinothricin (White et al., *Nucl. Acids Res.* 18:1062, 1990; Spencer et al., *Theor. Appl. Genet.* 79:625-631, 1990), a mutant EPSPV-synthase, which confers glyphosate resistance (Hinchee et al., *BioTechnology* 91:915-922, 1998), a mutant acetolactate synthase, which confers imidazoline or sulfonylurea resistance (Lee et al., *EMBO J.* 7:1241-1248, 1988), a mutant psbA, which confers resistance to atrazine (Smeda et al., *Plant Physiol.* 103:911-917, 1993), or a mutant protoporphyrinogen oxidase (see U.S. Pat. No. 5,767,373), or other markers conferring resistance to an herbicide such as glufosinate, sulfonamide, or phosphinotricin and sulfonylurea resistance (see, for example, Maliga et al., *Methods in Plant Molecular Biology,* Cold Spring Harbor Laboratory Press, 1995, page 39). Genes conferring resistance to antibiotics such as tetracycline; ampicillin, kanamycin, and chloramphenicol can be used for selection of the plasmid in prokaryotes such as *E. coli.*

Auxotrophic markers are selectable markers that can be used in a host having a mutation in a gene encoding a metabolic enzyme, such as, for example, arginosuccinate lyase, for arginine synthesis, nitrate reductase for nitrogen assimilation (ability to utilize nitrate), thi10 for thiamine biosynthesis, and nic for nicotinamide biosynthesis.

Negative selection markers that may be included on an EDM include, without limitation, thymidine kinase (Lupton et al. (1991) *Molecular and Cellular Biology* 11: 3374-3378), DAOO (Erikson et al. (2004) *Nature Biotechnology* 22: 455-458) URA, and sacB (Quenee et al. (2005) *Biotechniques* 38: 63-67).

Alternatively or in addition to including a reporter gene or selectable marker gene, an EDM as provided herein can include a gene encoding a metabolic enzyme, structural protein, kinase, phosphatase, nucleotide cyclase, phosphodiesterase, transcriptional regulator, transcriptional activator, transporter, secretory protein, ion channel, receptor, photosynthetic protein, chaperonin, ribosomal protein, or nuclear scaffold protein. In various examples, an EDM as provided herein can include a gene encoding a meganuclease, a zinc finger nuclease, a TALEN protein, a cas protein, a recombinase, a topoisomerase, or a transposase.

Further alternatively or additionally, an EDM as provided herein can comprise a nucleic acid sequence encoding a functional RNA, such as, for example, an interfering RNA or a precursor thereof, an antisense RNA, a ribozyme, a micro RNA, or a guide RNA of a CRISPR system. Preferably, the functional RNA is not a ribosomal RNA. In various examples, the functional RNA is designed to attenuate expression of a targeted gene.

In further examples, alternatively or in addition to any of the above, an EDM can include sequences for mediating homologous or site specific recombination, wherein the sequences for homologous recombination include genomic sequences that flank or comprise at least a portion of a gene targeted for gene replacement or disruption, or can include sequences recognized by site-specific recombination systems.

The ARSs of the present invention may be used in DNA constructs to enhance replication. Therefore, methods of enhancing replication are also provided herein utilizing the ARSs described herein. A method of enhancing replication of a DNA construct can comprise, for example: (1) providing an ARS of the present invention in a DNA construct; and (2) transforming the DNA construct into a host cell.

The ARSs of the present invention may be used in artificial chromosomes and episomal nucleic acid molecules such as plasmids to facilitate their replication in host cells. ARS elements can often function in non-native species (Kim et al. (2007) *Plasmid* 58:228-39). Therefore, ARSs or consensus ARS elements disclosed herein may facilitate replication of a chromosome (synthetic or naturally derived) or plasmid (synthetic or naturally derived) in species beyond those of the *Nannochloropsis* genus.

For example, a host cell for an artificial chromosome or EDM comprising an ARS of the present invention may optionally be an algal cell, such as a cell of a species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Ghroomonas, Chrysosphaera, Cricosphaera, Cryptheco-dinium, Cryptomonas, Cyclotella, Dunaliella, Ellipsoidon, Emiliania, Eremosphaera, Ernodesmius, Euglena, Eustigmatos, Franceia, Fragilaria, Fragilaropsis, Gloeothamnion, Haematococcus, Halocafeteria, Heterosigma, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudone-ochloris, Pseudostaurastrum, Pyramimonas, Pyrobotrys,*

*Scenedesmus, Skeletonema, Spyrogyra, Stichococcus, Tetraselmis, Thalassiosira, Tribonema, Vaucheria, Viridiella, Vischeria,* or *Volvox*.

Exemplary diatoms include members of the genera *Achnanthes, Amphora, Chaetoceros, Coscinodiscus, Cylindrotheca, Cyclotella, Cymbella, Fragilaria, Fragilaropsis, Hantzschia, Navicula, Nitzschia, Pavlova, Pseudo-Nitzschia, Phaeodactylum, Psammodictyon, Skeletonema, Thalassionema, Thallasiosira,* and *Vischeria*. Examples of eustigmatophytes that may be hosts for a nucleic acid construct that includes an ARS as provided herein include not only *Nannochloropsis* species but also species of *Monodus* and *Eustigmatos*. In some examples, an alga of a species of the genus *Nannochloropsis* such as, but are not limited to, *N. gaditana, N. granulata, N. limnetica, N. oceanica, N. oculata,* and *N. salina* is transformed with a nucleic acid construct that includes an ARS as provided herein.

Alternatively or in addition, a host cell for an artificial chromosome or EDM comprising an ARS of the present invention may optionally be a heterokont cell, an animal cell, a plant cell, a yeast cell, a fungal cell, or a protist. For example, heterokonts include not only eustigmatophytes and diatoms such as those listed above but also chytrid species, including labrinthulids. In some examples, heterokont species considered for use in the invention include, but are not limited to, Bacillariophytes, Eustigmatophytes, Labrinthulids, and Thraustochytrids. In some examples, the strain may be a species of *Labryinthula, Labryinthuloides, Thraustochytrium, Schizochytrium, Aplanochytrium, Aurantiochytrium, Japonochytrium, Diplophrys,* or *Ulkenia*. For example, the strain may be a species of *Thraustochytrium, Schizochytrium,* or *Aurantiochytrium*.

For example, an ARS sequence or variant, including a truncated variant of a validated ARS, or a region of DNA that includes a known or putative ARS can be assessed for function in a host species of interest by incorporating the known ARS, ARS sequence variant, or putative ARS into a circular DNA construct that includes a selectable marker functional in the host species of interest, and also includes, preferably an origin of replication for a bacterial strain that does not function in the host species of interest as well as a selectable marker that is functional in the bacterial strain. The circular DNA construct that includes the putative ARS or ARS variant can then be transformed into the host species of interest and transformants can be selected. Transformants can be analyzed to verify the presence of the circular molecule, for example, using PCR, restriction mapping, and/or Southern hybridization. Preferably the transformants are analyzed after multiple generations to verify the persistence of the construct, and further, the replication of the circular molecule can be further verified by isolating DNA from host species transformants under conditions in which circular DNA remains largely intact, transforming the isolated DNA into cells of the bacterial strain (for which the construct includes an origin of replication) and selecting bacterial transformants.

DNA can then be isolated from the bacterial transformants and analyzed by restriction digests and/or PCR for circular conformation, and used to retransform either or both of bacteria and the host species of interest. The persistence of the construct in cells of the host of interest together with the ability to transform bacteria (e.g., *E. coli*) with DNA isolated from the host species after multiple generations, indicates that the construct has been maintained in a non-integrated state, and therefore was able to replicate autonomously in the host species of interest.

Methods of Expressing a Gene

Methods are provided herein for propagating a gene of interest through at least eight generations of cell division, in which the method includes incorporating the gene of interest into and EDM as provided herein, transforming the EDM into a host organism, and propagating the host organism for at least eight generations under conditions in which the gene is expressed. In exemplary embodiments, the EDM includes a selectable marker gene, and the host organism is propagated under selection. The host organism can be, in various examples, an algal, heterokont, plant, animal, fungal organism, as described herein. For example, the host organism can be a microorganism, and may be a heterokont microorganism or microalga, including a diatom or Eustigmatophyte, for example, the microorganism may be a species of *Nannochloropsis*. In these methods, the EDM preferably includes a selectable marker gene, and the host organism is preferably propagated under selection, for example, in the presence of an antibiotic or toxin to which the selectable marker gene confers resistance.

In a related aspect of the invention, methods are provided for transiently expressing a gene or sequence of interest in a host cell, comprising transforming an EDM as provided herein into a host cell and culturing the host cell under conditions in which the gene or sequence is expressed. In exemplary embodiments the EDM includes a selectable marker gene, and the host cell is cultured in the presence of a selective agent for one or more generations. For example, the host cell may be cultured in the presence of the selective agent for one or more generations during which the gene or sequence of interest is expressed, and subsequently cultured in the absence of the selective agent for one or more additional generations, during or after which the gene or sequence of interest is not expressed.

EDM constructs that include a gene of interest for expression in a host cell can include regulatory sequences such as but not limited to promoter sequences and terminator sequences that are operably linked to the gene of interest. Such regulatory sequences, for example, promoter sequences, may be regulatable, e.g., inducible by environmental conditions or media components. Where a promoter is inducible, the method can further include inducing expression of the gene of interest. The promoters may be from the same genus or species as the host organism, or may be of a different species than the host organism.

A variety of known promoter sequences can be usefully deployed for transformation systems of microalgal and heterokont species. For example, the promoters commonly used to drive transgene expression in microalgae include various versions of the of cauliflower mosaic virus promoter 35S (CaMV35S), which has been used in both dinoflagellates and chlorophyta (Chow et al, *Plant Cell Rep.*, 18:778-780, 1999; Jarvis and Brown, *Curr. Genet.*, 317-321, 1991; Lohuis and Miller, *Plant J.*, 13:427-435, 1998). The SV40 promoter from simian virus has also reported to be active in several algae (Gan et al., *J. Appl. Phycol.*, 151 345-349, 2003; Qin et al., *Hydrobiologia* 398-399, 469-472, 1999). The promoters of RBCS2 (ribulose bisphosphate carboxylase, small subunit) (Fuhrmann et al., *Plant J.*, 19:353-361, 1999) and PsaD (abundant protein of photosystem I complex; Fischer and Rochaix, *FEBS Lett.* 581:5555-5560, 2001) from *Chlamydomonas* can also be useful. The fusion promoters of HSP70A/RBCS2 and HSP70A/β2TUB (tubulin) (Schroda et al., *Plant J.*, 21:121-131, 2000) can also be useful for an improved expression of transgenes, in which HSP70A promoter may serve as a transcriptional activator when placed upstream of other promoters. High-level expression of a gene of interest can also be achieved in heterokonts, for example diatoms species, under the control of a promoter of an fcp gene encoding a diatom fucoxanthin-chlorophyll a/b binding protein (Falciatore et al., *Mar. Biotechnol.*, 1:239-251, 1999; Zaslayskaia et al., *J. Phycol.* 36:379-386, 2000) or the vcp gene encoding a eustigmatophyte violaxanthin-chlorophyll a/b binding protein (see U.S. Pat. No. 8,318,482). If so desired, inducible promoters can provide rapid and tightly controlled expression of genes in transgenic microalgae. For example, promoter regions of the NR genes encoding nitrate reductase can be used as such inducible promoters. The NR promoter activity is typically suppressed by ammonium and induced when ammonium is replaced by nitrate (Poulsen and Kroger, *FEBS Lett* 272: 3413-3423, 2005), thus gene expression can be switched off or on when macroalgal cells are grown in the presence of ammonium/nitrate. Other regulatable promoters from *Nannochloropsis* include those disclosed in U.S. Patent Appl. Pub. No. US 2013/0023035, incorporated by reference herein. Additional *Nannochloropsis* algal promoters that can find use in the constructs and transformation systems provided herein include those disclosed in U.S. patent application Ser. No. 13/486,930, filed Jun. 1, 2012; U.S. patent application Ser. No. 13/693,585, filed Dec. 4, 2012; and U.S. patent application Ser. No. 13/915,522, filed Jun. 11, 2013, all incorporated by reference herein.

The gene of interest can be any gene of interest, including, without limitation, a growth regulator, a photosynthetic protein, a metabolic enzyme, a structural protein, a kinase, a phosphatase, a nucleotide cyclase, a phosphodiesterase, a transcriptional regulator, a transcriptional activator, a transporter, a secretory protein, an ion channel protein, a receptor, a chaperonin, a ribosomal protein, or a nuclear scaffold protein. Additional genes that can be included on an EDM as provided herein include genes encoding proteins that can be used to modify the genome. For example, a meganuclease, a zinc finger nuclease, a TALEN protein, a cas protein, a recombinase, a topoisomerase, or a transposase.

Also provided herein are methods for effecting homologous recombination or site-specific recombination in a host cell of interest, in which the method includes introducing an EDM that includes a selectable marker and a construct for homologous recombination or site specific recombination into a host cell. A construct for homologous recombination can include, for example, a nucleic acid sequence from a genetic locus of interest having at least one alteration with respect to the locus of interest. For example, a construct for homologous recombination can include at least 200, at least 300, at least 400, at least 500, at least 600, at least 700, at least 800, at least 900, at least 1000, at least 1200, at least 1400, at least 1600, at least 1800, at least 2000, at least 2200, at least 2400, at least 2600 at least 2800, or at least 3000 base pairs of sequence from the genomic locus to be targeted, where the genomic sequence differs from the native sequence by at least one mutation, deletion, or insertion. For example, the genomic sequence in the homologous recombination construct can be interrupted by a selectable marker gene. A construct for site specific recombination can include, for example, sites recognized by recombinases, such as but not limited to lox or frt sequences, that may flank a gene sequence that may be mutated with respect to the native gene of the host organism. An EDM that includes a homologous recombination construct can be propagated in a host cell for multiple generations, for example, 10, 20, 30, 40, 50, or more generations, for example, by using selective media on which the EDM confers the ability to grow. Selection can be removed to allow the recombination construct to be lost from the cultured cells, and the cultured cells can be tested for the presence of the integrated gene knock out or gene replacement construct, for example, by PCR, Southern blot, and/or DNA sequencing. Optionally, the recombination construct can include a second selectable marker and selection for integration of the construct can be performed using the second marker, subsequent to removing selection for the presence of the EDM.

Methods of Identifying ARS Elements

The present invention also provides methods of identifying ARS elements from organisms of interest. A method for identifying an ARS element can comprise, for example: (1) sequencing the region between the 18S and 28S repeats in a chromosome from an organism of interest; and (2) selecting a portion, for example 5 kbp or less, 4 kbp or less, 2 kbp or less, or 1 kbp or less, of a nucleic acid sequence having the lowest guanidine/cytosine content within the sequenced region. For example, the methods of the present invention may optionally be used to identify an ARS from an algal cell, such as a cell of a species of *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria,* or *Volvox*. Alternatively or in addition, the methods of the present invention may optionally be used to identify an ARS from a heterokont, an animal, a plant, a fungus, or a protist.

For example, the method may be used to isolate an ARS from a heterokont such as a Eustigmatophyte (including, but not limited to a species of *Eustigmatos, Monodus, Nannochloropsis,* or *Vischeria*); a diatom (including, but not limited to a species of *Achnanthes, Amphora, Chaetoceros, Cyclotella, Fragilaria, Navicula, Nitzschia, Phaeodactylum,* or *Thalassiosira. Monodus, Nannochloropsis,* or *Vischeria*); or a labrinthulid or thraustochytrid, such as, but not limited to a species of *Labryinthula, Labryinthuloides, Thraustochytrium, Schizochytrium, Aplanochytrium, Aurantiochytrium, Japonochytrium, Diplophrys,* or *Ulkenia*.

The following examples illustrate but do not limit the invention.

EXAMPLES

These examples describe a novel process used to identify ARS elements in a species of interest. It was hypothesized that an ARS exists between the 18S, 5.8S, and 28S rDNA repeat regions, known as 35S rDNA repeat units, in *Nannochloropsis* genomes. These types of repeat regions cannot be assembled in genome sequence databases because of their repetitive nature and the general inability to integrate repetitive elements into genome assemblies. The examples further demonstrate the functionality of these sequences in supporting autonomous replication of an episomal DNA molecule (EDM) in *Nannochloropsis*, and various uses of the EDM for delivery and expression of transgenes.

Example 1

Identification of Algal Autonomous Replication Sequences

Whole genomic DNA of *Nannochloropsis gaditana* was prepared for shotgun 454-pyrosequencing. Genomic DNA was used for library construction according to the recommended protocol (454 Life Sciences) for single long reads. The sequences were generated by GS FLX Titanium series sequencing runs. Mate-pair and paired-end genomic DNA library construction was also performed for Illumina short-read (100 bp) sequencing of the *Nannochloropsis* genome. Genome sequence assemblies were carried out using Newbler assembler version 2.0.00.20 for the 454-sequence data and using ALLPATHS-LG for the Illumina mate-pair and paired-end data.

A repetitive ribosomal DNA region of the genome that was assembled as a unit was found to lack 5S ribosomal DNA sequences that typically are found between the ribosomal RNA gene repeat units that include the 18S, 5.8S, and 28S ribosomal RNA genes, referred to as 35S ribosomal RNA gene repeats. To isolate the 5S ribosomal DNA region that is typically found between 35S ribosomal DNA repeat units, the region between *Nannochloropsis gaditana* 35S ribosomal DNA gene repeat units was amplified from genomic DNA by PCR, isolated, and sequenced. As anticipated, several slightly different DNA sequences were acquired, at least one of which included a sequence having homology to the *Cyanidioschyzon merolae* (red alga) 5S rDNA sequence (Genbank: NC_010138 REGION: 84222 . . . 84389). The GC content of the isolated inter-35S rDNA repeat DNA sequences showed regions with high AT. content, a characteristic of some ARSs, adjacent to GC-rich regions that included 5S rDNA-homologous sequences. A ~1.6 kpb A/T rich region (SEQ ID NO:1) of one of the inter-35S rDNA repeat amplified regions was isolated for further characterization.

The 1.6 kbp sequence, referred to as "NgARS1.6" (SEQ ID NO:1), was analyzed for internal repeats by comparing the sequence with itself using the National Center for Biotechnology Information (NCBI) BLAST program (graphically depicted in FIG. 1). This demonstrated that the sequence included imperfect tandem repeats of approximately 85 bp. Imperfect tandem sequence repeats are also found in the *S. cerevisiae* ARS cluster, indicating, along with the localization to the inter-35S rDNA repeat region of the genome, that SEQ ID NO:1 included an ARS. Two approximately 85 bp regions of the AT-rich putative *Nannochloropsis* ARS with significant primary sequence identity (SEQ ID NO:2 and SEQ ID NO:3; consensus sequence provided as SEQ ID NO:4) were found to make up part of a repetitive and low GC area found in the 5S rDNA sequence region.

Example 2

Characteristics of Algal Autonomous Replication Sequences

Additional sequences (SEQ ID NOs: 5, 6, 7, 8, 9, 10, 11, and 12) isolated from *Nannochloropsis gaditana* genomic DNA by amplification of genome regions between the 35S rDNA repeat units ranged in size from 770 bp (NgARS2; SEQ ID NO:6) to 4421 bp (NgARS1; SEQ ID NO:5). See Table 1.

Figure 2C:
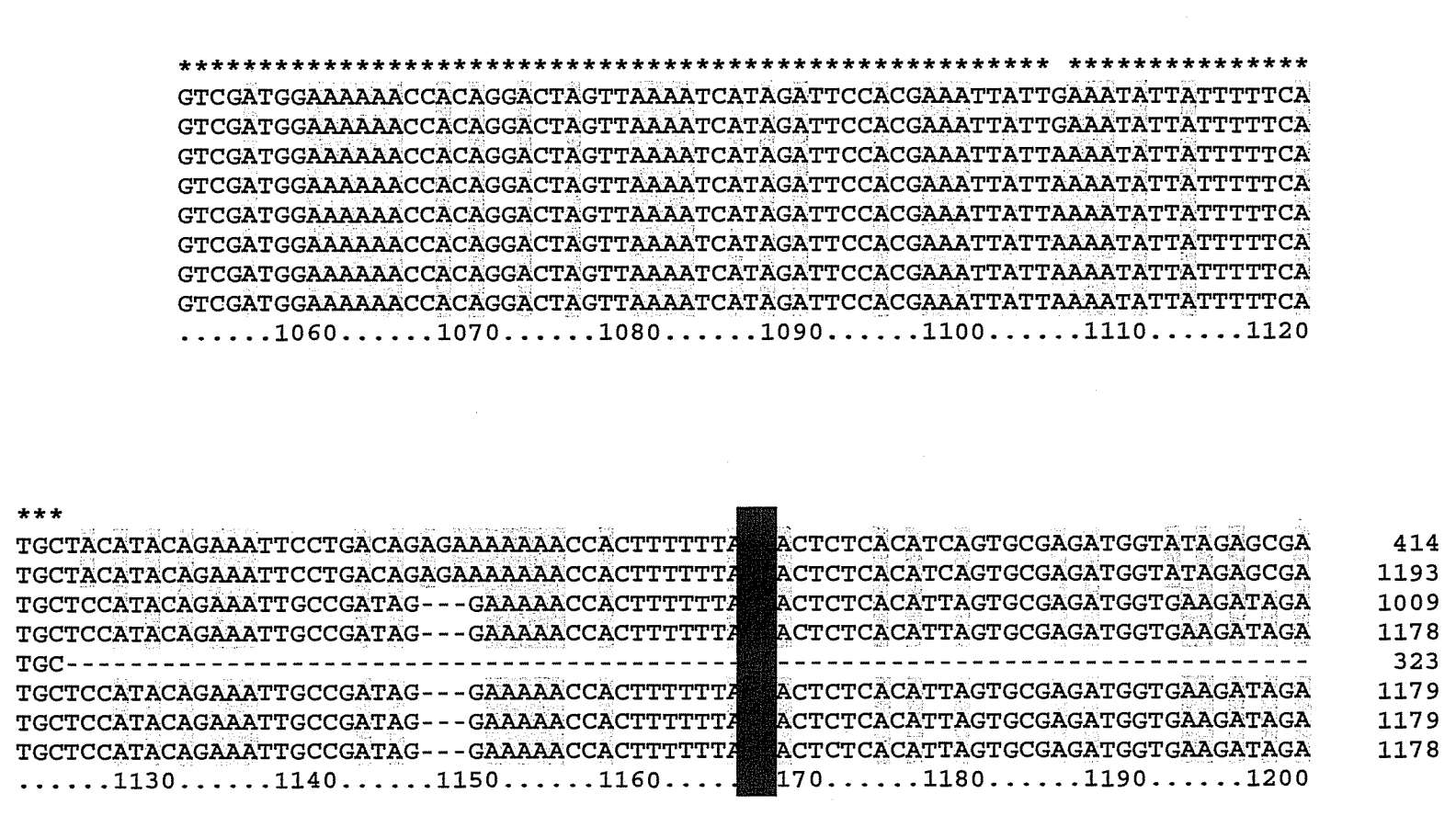

These fragments were found to have a high degree of sequence homology with one another over a stretch of about 350 bp of AT rich sequence as shown in the sequence alignment of FIG. 2. With respect to nucleotides 1-323 of NgARS2 (SEQ ID NO:6), provided as SEQ ID NO:13, nucleotides 1-337 of NgARS1 (SEQ ID NO:5) were found to be 89% identical, NgARS1.6 (SEQ ID NO:1) nucleotides 301-622 were found to be 99% identical, nucleotides 780-1116 of NgARS3 (SEQ ID NO:7) were found to be 89% identical, nucleotides 784-1104 of NgARS4 (SEQ ID NO:8) were found to be 99% identical, nucleotides 614-935 of NgARS5 (SEQ ID NO:9) were found to be 99% identical, and nucleotides 784-1105 of NgARS7 (SEQ ID NO:10) were found to be 99% identical. With respect to nucleotides 322 to 770 of NgARS2 (SEQ ID NO:6), provided as SEQ ID NO:14, nucleotides 3973-4421 of NgARS1 (SEQ ID NO:5) were found to be 99% identical, nucleotides 2956-3404 of NgARS3 (SEQ ID NO:7) were found to be 98% identical, and nucleotides 2026-2474 of NgARS8 (SEQ ID NO:11) were found to be 99% identical. In addition, nucleotides 983-1183 of NgARS-Sm (SEQ ID NO:12) were found to be 100% identical to nucleotides 322-522 of NgARS2 (SEQ ID NO:6). Thus, all of the isolated fragments had a high percentage of sequence identity to at least 300 nucleotides of NgARS2. NgARS1, NgARS1.6, NgARS3, NgARS4, NgARS5, and NgARS7 were found to include sequences having at least 85% identity to SEQ ID NO:13 (nucleotides 1-323 of SEQ ID NO:6 (NgARS2)). NgARS8 was found to include sequences having at least 85% identity to SEQ ID NO:14 (nucleotides 322-770 of SEQ ID NO:6 (NgARS2)). NgARS1 and NgARS3 were found to have at least 85% sequence identity to both "halves" of NgARS2: at least 85% identity (at least 89% identity) to SEQ ID NO:13, and at least 95% identity (at least 98% identity) to SEQ ID NO:14.

TABLE 1

*Nannochloropsis* ARS Sequences

| Putative ARS Sequence | Length of Fragment | Homology to SEQ ID NO: 13 (nucleotides 1-323 of SEQ ID NO: 6) | Homology to SEQ ID NO: 14 (nucleotides 322-770 of SEQ ID NO: 6) |
|---|---|---|---|
| NgARS1.6 (SEQ ID NO: 1) | 1624 bp | nucleotides 301-622, 99% identical | |
| NgARS1 (SEQ ID NO: 5) | 4421 bp | nucleotides 1-337, 89% identical | nucleotides 3973-4421, 99% identical |
| NgARS2 (SEQ ID NO: 6) | 770 bp | Self | Self |
| NgARS3 (SEQ ID NO: 7) | 3777 bp | nucleotides 780-1116, 89% identical | nucleotides 2956-3404, 98% identical |
| NgARS4 (SEQ ID NO: 8) | 3093 bp | nucleotides 784-1104 99% identical | |
| NgARS5 (SEQ ID NO: 9) | 3722 bp | nucleotides 614-935, 99% identical | |
| NgARS7 (SEQ ID NO: 10) | 2543 bp | nucleotides 784-1105, 99% identical | |
| NgARS8 (SEQ ID NO: 11) | 2474 bp | | nucleotides 2026-2474, 99% identical |

TABLE 1-continued

Nannochloropsis ARS Sequences

| Putative ARS Sequence | Length of Fragment | Homology to SEQ ID NO: 13 (nucleotides 1-323 of SEQ ID NO: 6) | Homology to SEQ ID NO: 14 (nucleotides 322-770 of SEQ ID NO: 6) |
|---|---|---|---|
| NgARS-Sm (SEQ ID NO: 12) | 1183 bp | | nucleotides 983-1183, 98% identical |

Example 3

Validation of ARS Function in Replication in *Nannochloropsis Gaditana*

Figure 3:
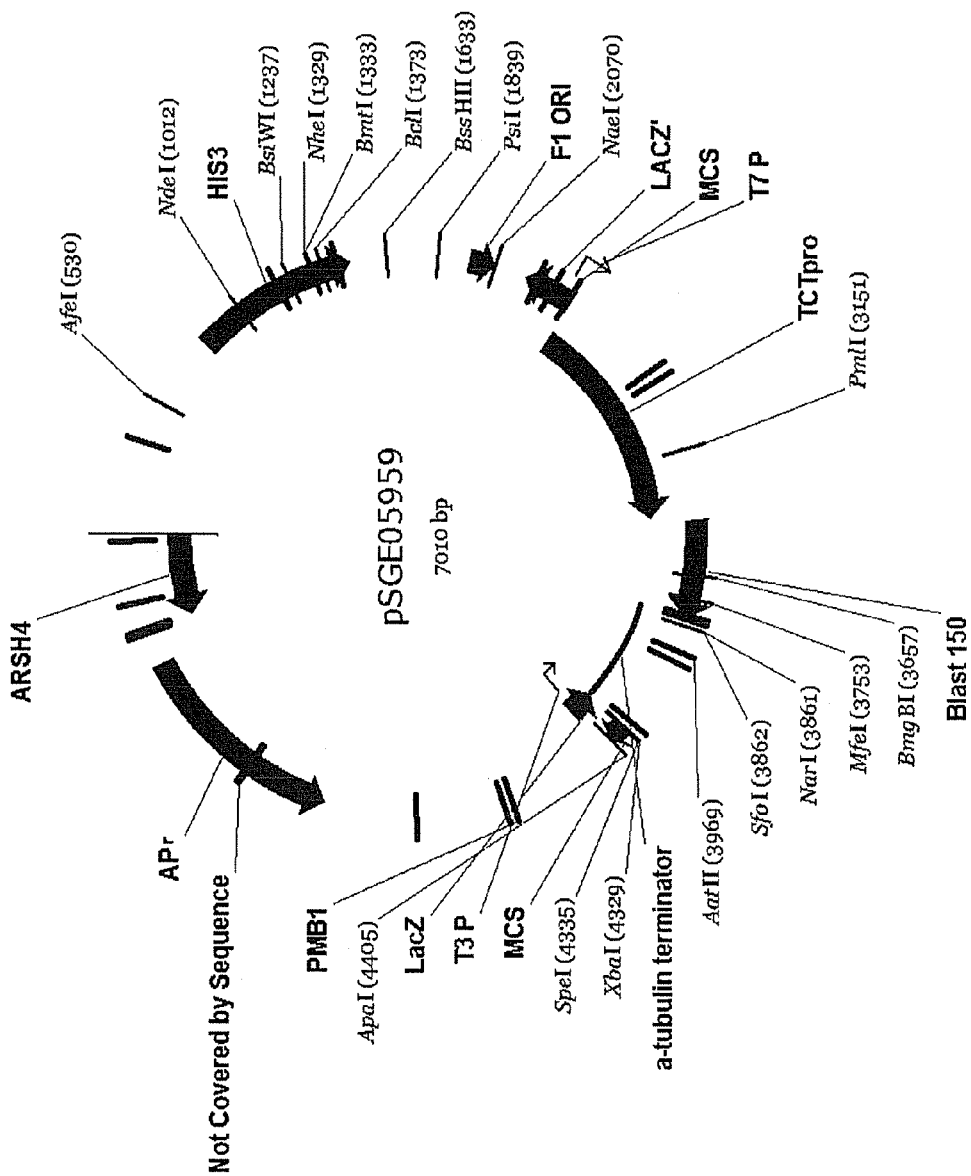
FIG. 3 is a vector map of pSGE-05959 that included an AfeI site for insertion of putative ARSs. The vector included a blasticidin resistance gene ("Blast 150"; SEQ ID NO:19) driven by the *Nannochloropsis* TCTP promoter (SEQ ID NO:18) and also included a PMB1 ori and ampicillin resistance gene (Apr) for replication and selection in *E. coli*.

A plasmid vector, pSGE-05959 (FIG. 3), was designed to test the putative NgARS sequences SEQ ID NO:5 (NgARS1), SEQ ID NO:6 (NgARS2), SEQ ID NO:7 (NgARS3), SEQ ID NO:8 (NgARS4), SEQ ID NO:9 (NgARS5), SEQ ID NO:10 (NgARS7), SEQ ID NO:11 (NgARS8), and SEQ ID NO:12 (NgARS-Sm) for their ability to support autonomous replication of an episomal DNA molecule by cloning the sequences into the unique AfeI site within the vector. The constructs in circular (uncut) form were used to transform *Nannochloropsis* as described below:

The pSGE-05959 based constructs were transformed into *Nannochloropsis* cells by electroporation. Briefly, *Nannochloropsis gaditana* cells were grown in PM032 media and harvested at a concentration between $1-3 \times 10^7$ cells/mL. Cells were centrifuged at 2500×g for 10 minutes at 25° C. to pellet the cells. Cells were then resuspended in a sterile solution of 385 mM sorbitol and centrifuged again, then washed two more times in sorbitol to remove all traces of media. The cell pellet was resuspended in sorbitol to a final concentration of $1 \times 10^{10}$ cells/mL. 0.5-5 µg of Uncut (i.e., circular) vectors based on pSGE-05959 plasmid DNA that included one of the following putative NgARS elements (SEQ ID NO:5 (NgARS1), SEQ ID NO:6 (NgARS2), SEQ ID NO:7 (NgARS3), SEQ ID NO:8 (NgARS4), SEQ ID NO:9 (NgARS5), SEQ ID NO:10 (NgARS7), SEQ ID NO:11 (NgARS8), and SEQ ID NO:12 (NgARS-Sm)) were aliquoted into a microfuge tubes, and 100 µL of cell mixture was mixed with the DNA. The mixture was transferred to chilled 2 mm gap electroporation cuvette. The electroporator was set to 50 µF capacitance, 500 ohms resistance and a voltage of 2.2 kV. Following electroporation, samples were resuspended in 1 mL of sorbitol and incubated on ice for a few minutes. Cells were transferred to 15 mL conical tubes containing 10 mL of fresh media, and allowed to recover overnight in dim light (~5 µmol photons $m^{-2}$ $sec^{-1}$). The next day, cells were plated at a concentration between $5-7 \times 10^8$ cells/mL on PM032 plates containing 100 µg/mL blasticidin. Plates were incubated under constant light (~80 µmol photons $m^{-2}$ $sec^{-1}$) until colonies appeared (about 2-3 weeks).

PM032 media includes: 35 ppt Instant Ocean Salts (Aquatic Eco Systems; Apopka, Fla.), 10× Guillard's F/2 marine water enrichment solution (50× stock from Sigma-Aldrich, St. Louis, Mo., cat. No. G0154; final concentrations of components in media: 8.825 µM Sodium nitrate; 0.32 mM Sodium phosphate monobasic; 0.205 µM Biotin; 0.420 µM Cobalt chloride•6H$_2$O; 0.400 µM Cupric sulfate•5H$_2$O; 0.11713 mM Disodium EDTA•2H$_2$O; 9.095 µM Manganese chloride•4H$_2$O; 0.248 µM Sodium molybdate•2H$_2$O; 2.965 µM Thiamine•HCl; 0.037 µM Vitamin B$_{12}$; 0.765 µM Zinc sulfate•7H$_2$O).

Blasticidin-resistant colonies were obtained from the transformation events. Non-homologous End Joining (NHEJ) based recombination into the algal genome (i.e. random integration) is exceedingly rare in the absence of linear DNA molecules, and thus the mere presence of the blasticidin resistant *N. gaditana* colonies is strong evidence for the function of the tested ARS element. Additionally, it was predicted that functional ARS elements would result in the production of an Episomal DNA Molecule (EDM) within the algae that could be recovered from the algae and, due to the presence of *E. coli* and/or *Saccharomyces cerevisiae* replication elements, directly transformed into *E. coli* or *S. cerevisiae*. DNA was therefore isolated from blasticidin-resistant *Nannochloropsis* lines as described below.

100-1000 uL of mid-log phase algal culture was placed into a 1.5 mL microcentrifuge tube and the algae were pelleted at 4,000×g for 2 minutes. The supernatant was removed and the pellet resuspended in 1 mL of sterile filtered milliQ (SFMQ) water. The mixture was pelleted as before and resuspended in 200 uL of SFMQ water. To this mixture, 200 uL of 2× Proteinase K buffer (100 mM Tris pH 8.0, 100 mM EDTA, 1% SDS) and 5 uL of Proteinase K solution (20 mg/mL, NEB P8102) were added and briefly vortexed. The mixture was placed on a vortexer heated to 50° C. at 1000 RPM for 1 hr. The samples were cooled to 37° C. and 5 uL of DNAse free RNAseA (10 mg/mL) was added. The samples were placed on the heated vortexer at 37° C. and 1000 RPM for 15 minutes. 400 uL of PCIA (25:24:1 Phenol:Chloroform:Isoamyl alcohol pH 8.0) was added and the samples were thoroughly vortexed at room temperature (RT). The samples were pelleted at 21,817×g for 5 min at RT. The upper aqueous layer was transferred to a new tube. 30 uL of 5M NaCl was added and mixed by vortexing. 1.1 mL of 100% ethanol was added and mixed by vortexing and the samples were placed at −20° C. for ~10 min. The samples were pelleted at 20,817×g at 4° C. for 20 min. All of the supernatant was removed and the pellet was vortexed thoroughly in the presence of 1 mL of 70% ethanol. The samples were pelleted at 20,817×g at RT for 5 min and the supernatant was completely removed. The pellet was briefly air dried and resuspended in 25 uL of SFMQ water. 2 uL was used for DNA quantification on the qBit DNA fluorometer.

Figure 4:
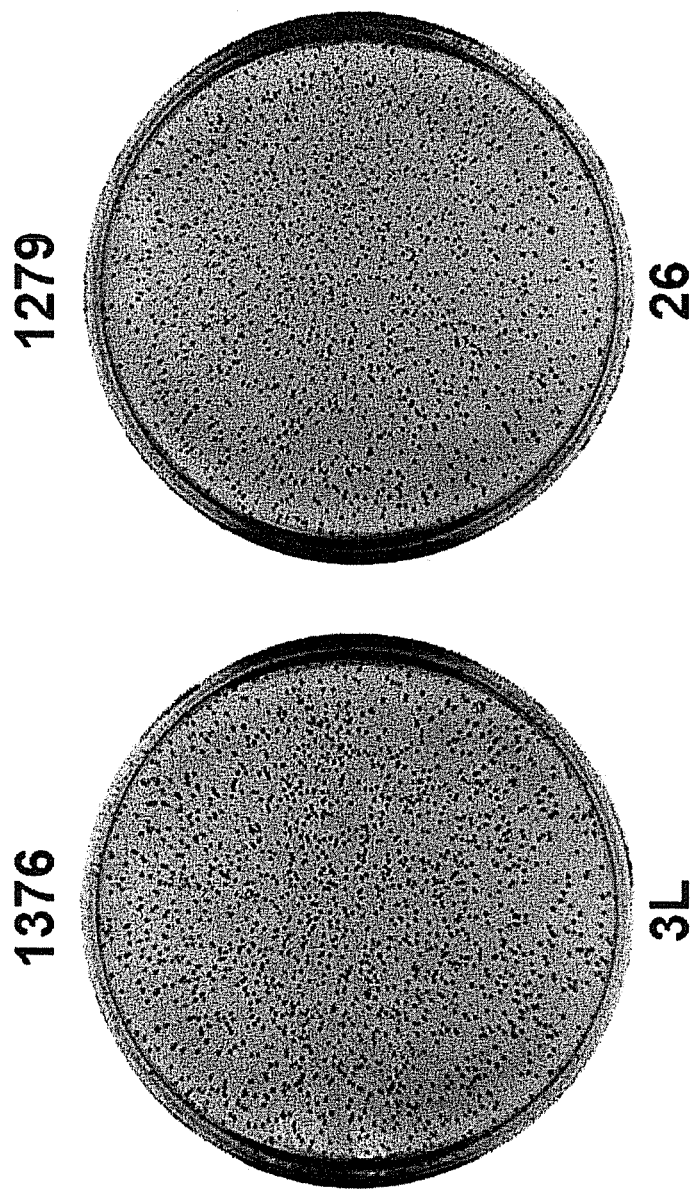
FIG. 4 are photographs of transformation plates showing *E. coli* colonies resulting from transformation with uncut DNA isolated with *Nannochloropsis* lines that had been transformed with EDMs that included NgARS2.

An aliquot of between 1 ng to approximately 250 ng of DNA isolated from each of the blasticidin resistant *Nannochloropsis* transformants was used to separately transform *E. coli* ElectroSHOX cells (Bioline BIO-85038) using standard electroporation techniques (50 uL cells, 5 uL max DNA solution, 1 mm gap cuvette, 2.5 kV, 25 ohm, 50 uF, SOC resuspension). A ratio of *E. coli* colony count to electroporated DNA amount was used to determine which of the putative NgARSs conferred eukaryotic replicative function to the Episomal DNA Molecule (EDM). Five of the eight putative NgARSs (NgARS1, NgARS2, NgARS3, NgARS7, and NgARS-Sm) showed significantly higher values for the colony number per transformed DNA ratio than the control, with NgARS2 having the highest transformation efficiency (Table 2), strongly suggesting that the pSGE-05945 construct with NgARS2 was most efficiently replicating as an episome in these *Nannochloropsis* lines. Photographs of exemplary transformation plates are provided in FIG. 4. To confirm that the recovered colonies contained the EDM, a standard plasmid miniprep procedure (Qiagen) was performed on cultures that came from a sample of these transformants. The isolated plasmid DNA was used in PCR reactions to confirm the presence of the GFP gene (Primers were: GFP.ColCheck.f1, gttgctgtgatcctcctccac (SEQ ID NO:15) and GFP.ColCheck.r1 catgaccaacaag atgaagagcac (SEQ ID NO:16); generating a 512 bp PCR product that included most of the GFP coding region) and indicated that the initial EDM was providing the host *E. coli* with the necessary antibiotic resistance. Samples of the recovered vectors were fully resequenced and shown to have no changes from the parental strain, indicating that propagation of these EDMs within *Nannochloropsis* did not result in any changes to the EDM over the time course of the experiment.

TABLE 2

Results of transforming recovered *Nannochloropsis* EDMs into *E. coli*

| ARS ID | Plasmid ID | Recovered Colony # Average | Electroporated DNA Quantity (ng) Average | Col/DNA |
|---|---|---|---|---|
| NgARS1 | pSGE05944 | 18.00 | 27.35 | 0.66 |
| NgARS2 | pSGE05945 | 64.00 | 39.78 | 1.61 |
| NgARS3 | pSGE05946 | 36.00 | 138.00 | 0.26 |
| NgARS4 | pSGE05947 | 12.14 | 131.47 | 0.09 |
| NgARS5 | pSGE05948 | 10.11 | 54.46 | 0.19 |
| NgARS7 | pSGE05949 | 41.33 | 128.33 | 0.32 |
| NgARS8 | pSGE05950 | 19.67 | 116.43 | 0.17 |
| No ARS (control) | pSGE05959 | 5.25 | 33.00 | 0.16 |
| NgARS-Sm | pSGE05943 | 12.00 | 14.30 | 0.84 |

Example 4

Validation of ARS Function in Replication in Other *Nannochloropsis* Sp

*Nannochloropsis oceanica*, a species of *Nannochloropsis* distantly related to *N. gaditana*, was used to determine the species specificity of the isolated NgARS2 element. pSGE05945, and/or related NgARS2 containing vectors, was transformed into *N. oceanica* using similar protocols as for *N. gaditana* and using the same amount of vector DNA for each transformation event (~2 ug). Table 3 provides the results and demonstrates that similar numbers of blasticidin resistant colonies arise from transforming *N. oceanica* as *N. gaditana*, thus demonstrating broad host range functionality for the isolated NgARS2 element. The slightly higher number of colonies seen on the *N. oceanica* plates is likely due to slightly higher transformation efficiencies of that strain of *Nannochloropsis*. Transformation of an NgARS2-containing EDM into both *N. gaditana* and *N. oceanica* has been performed multiple times, using EDM constructs up to 100 kb in size.

TABLE 3

Transformation of *Nannochloropsis* species with EDM containing NgARS2

| Species | No. of blasticidin resistant colonies, pSGE-05945 vector |
|---|---|
| *N. gaditana* | ~200 |
| *N. oceanica* | ~300 |

Example 5

Necessity of ARS Elements for Replicative Function of EDMs within *N. gaditana*

NgARS2 was also cloned into a pUC-based plasmid vector that included a hygromycin resistance gene (SEQ ID NO:17) driven by the TCTP promoter (SEQ ID NO:18) for selection of *Nannochloropsis* transformants. The resulting construct, pSGE-6023, was used to transform *Nannochloropsis gaditana* essentially according to the methods provided in Example 3, resulting in approximately 100 colonies. A control transformation in which the same vector was used, except that the vector did not include NgARS2 (SEQ ID NO:6), resulted in only a single algal colony, presumably resulting from the relatively rare occurrence of integration of the EDM construct into the genome. This experiment was repeated with a similar construct that replaced the Hygromycin antibiotic resistance cassette with the Blasticidin resistance cassette and showed essentially the same results. These results showed that the NgARS2 sequence is necessary for EDM replication within *N. gaditana*.

Example 6

Determination of Gene Expression Profiles within EDM Constructs

Figure 5:
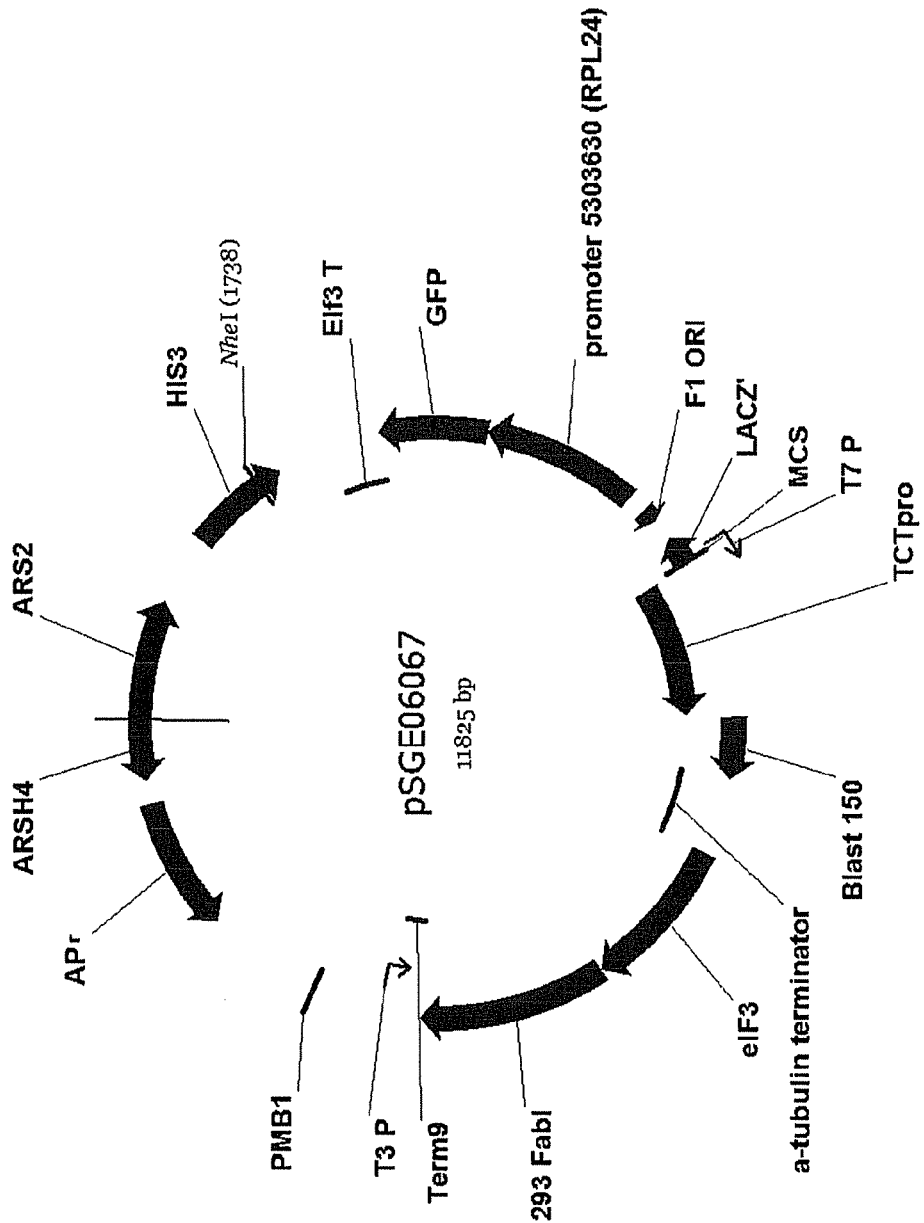
FIG. 5 is a vector map of pSGE-06067 that included NgARS2. The vector included a blasticidin resistance gene ("Blast 150"; SEQ ID NO:19) driven by the *Nannochloropsis* TCTP promoter (SEQ ID NO:18). Also included in the vector was a gene encoding TurboGFP (SEQ ID NO:21) driven by *Nannochloropsis* promoter 5303630 (SEQ ID NO:22) and a gene encoding a *Cyclotella* enoyl ACP reductase (293 FabI; SEQ ID NO:24). The vector also included a PMB1 ori and ampicillin resistance gene (Apr) for replication and selection in *E. coli*.

A plasmid vector, pSGE-6067 (FIG. 5), was designed to include NgARS2 (SEQ ID NO:6) previously isolated and described in Example 2 to determine if there are differences between randomly integrated and EDMs in the expression pattern of desired metabolic or non-metabolic genes. In addition to the NgARS2 sequence (SEQ ID NO:6), a gene conferring resistance to blasticidin ("Blast150"; SEQ ID NO:19) driven by the *Nannochloropsis* TCTP promoter (SEQ ID NO:18) and followed by a *Nannochloropsis* alpha tubulin terminator (SEQ ID NO:20) was included in the construct as a selectable marker. The plasmid construct further included as a reporter gene the green fluorescent protein TurboGFP (SEQ ID NO:21; Evrogen) driven by *Nannochloropsis* promoter 5303630 (SEQ ID NO:22) and linked to the *Nannochloropsis* eIf3a terminator (SEQ ID NO:23). For replication and selection in *E. coli*, the plasmid construct included the pMB1 ORI, an origin of replication for *E. coli*, and the beta lactamase or "bla" gene conferring ampicillin resistance (APr), all derived from the commonly used pUC based vectors. The construct additionally included a gene encoding the metabolic enzyme enoyl ACP reductase (ENR) from *Cyclotella* (SEQ ID NO:24) linked to the eIF3a promoter (SEQ ID NO:25) and T9 terminator (SEQ ID NO:26).

The pSGE-6067 construct was transformed into *Nannochloropsis* cells by electroporation as previously described. Blasticidin-resistant *Nannochloropsis* colonies from the transformations of Example 3 were streaked into patches on fresh blasticidin (100 μg/mL) plates, and those patches served as the seed source for initiating 10 ml volume PM074 liquid cultures that included 75 mg/mL blasticidin.

As previously described, cells were harvested for DNA isolation and the resultant DNA was used to transform *E. coli*. *E. coli* colonies were counted and screened for the presence of the GFP gene (SEQ ID NO:21) and the NgARS2 sequence (SEQ ID NO:6) by PCR. Table 4 shows that EDMs isolated from the transformed *N. gaditana* lines were positive for both the GFP gene and the requisite ARS element.

Based on this assessment, *Nannochloropsis* lines 101, 107, 108, 109, and 110 were considered to be carrying an EDM. To confirm this, DNA was also isolated from *E. coli* transformants using a commercial DNA "miniprep" kit (Qiagen) for isolating plasmid DNA. The isolated plasmid DNA was run on a gel in either digested or undigested form and was seen to be identical to the parental lines, with the exception of line 101, which is further discussed below.

TABLE 4

Transformation of *E. coli* with undigested DNA isolated from *Nannochloropsis* lines transformed with NgARS2 Construct pSGE-6067

| *Nannochloropsis* Blasticidin-resistant transformant line | Number of *E. coli* transformants using extracted uncut DNA | GFP PCR | ARS PCR |
| --- | --- | --- | --- |
| 101 | 1279 | + | + |
| 102 | 0 | NA | NA |
| 103 | 0 | NA | NA |
| 104 | 3 | + | + |
| 105 | 0 | NA | NA |
| 106 | 0 | NA | NA |
| 107 | 1376 | + | + |
| 108 | 1867 | + | + |
| 109 | 1985 | + | + |
| 110 | 2118 | + | + |

Figure 6:
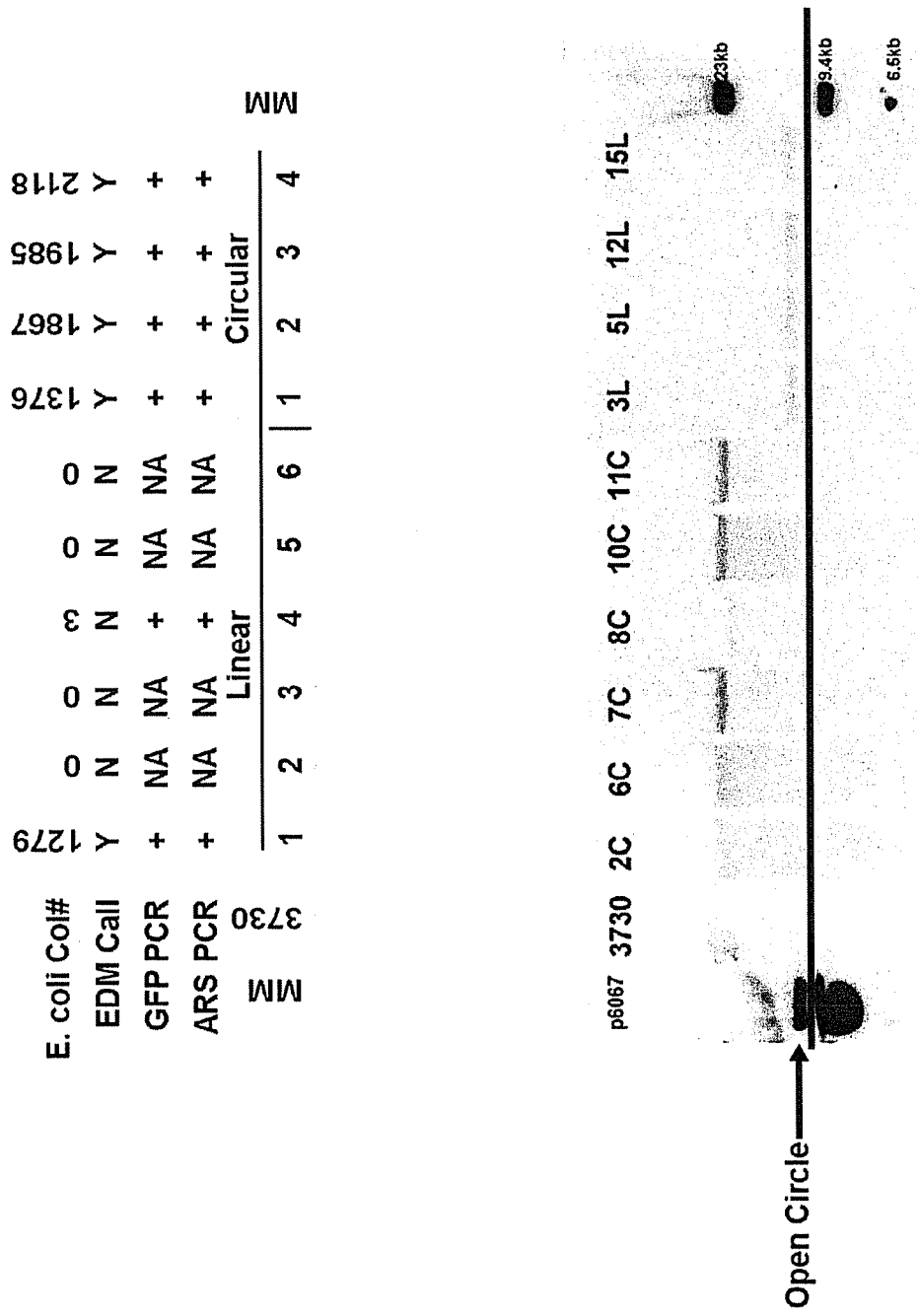
FIG. 6 is a photograph of a Southern blot of DNA extracted from *Nannochloropsis* lines transformed with a vector (EDM) that included NgARS2 and digested with an enzyme that does not cut the EDM. Above the lanes designated for each transformed *Nannochloropsis* line, data is provided on the number of colonies that resulted from transforming *E. coli* with the DNA extracted from that line, along with the results of PCR to detect the GFP gene and ARS, and a determination of whether the line was considered to be carrying an EDM ("EDM call").

Aliquots of *Nannochloropsis* gDNA were digested with PsiI, an enzyme that does not cut pSGE06067, and run on 0.65% agarose gels, which were electrotransferred to a nylon membrane for a Southern Blot using the Blast150 (blasticidin resistance) gene sequence SEQ ID NO:19) as a probe. The results of the Southern blot are provided in FIG. 6. The Southern blot demonstrated that at least four of the five *Nannochloropsis* lines that carried DNA able to transform *E. coli* at a frequency indicative of plasmid DNA did in fact include pSGE-6067 DNA in open circular form. By contrast, blasticidin-resistant *Nannochloropsis* lines whose DNA was not able to transform *E. coli* (or transformed *E. coli* at a very low frequency inconsistent with undigested plasmid DNA, e.g., line 104), did not include pSGE-6067 DNA in circular form, but rather appeared to have pSGE-6067-hybridizing DNA in higher molecular weight DNA, indicating that pSGE-6067, or at least a portion thereof including the blasticidin resistance gene, had integrated into the *Nannochloropsis* genome. To locate possible integration sites, the genomic DNA for lines 101, 102, 107, 108, 109 and 110 were resequenced using a MiSeq deep sequencer (Illumina). Mapping the resultant data back to the genome assembly showed no detectable integration events for lines 101, 107-110, consistent with them being purely episomal, and a single integration point for line 102, indicating that the linear construct had integrated into the host genome. Line 101, which started out as a linear molecule, showed at least three whole molecule concatamerization events, with the construct sequences multimerized either in imperfect tandem and/or as inversions, leading to a circular EDM. When the Line 101 EDM was isolated from *E. coli*, and its uncut form was run on a gel, it showed a banding pattern consistent with unresolved strand breakage, which is consistent with the presence of multiple bacterial origins of replication that would be predicted to exist in that molecule.

Figure 7:
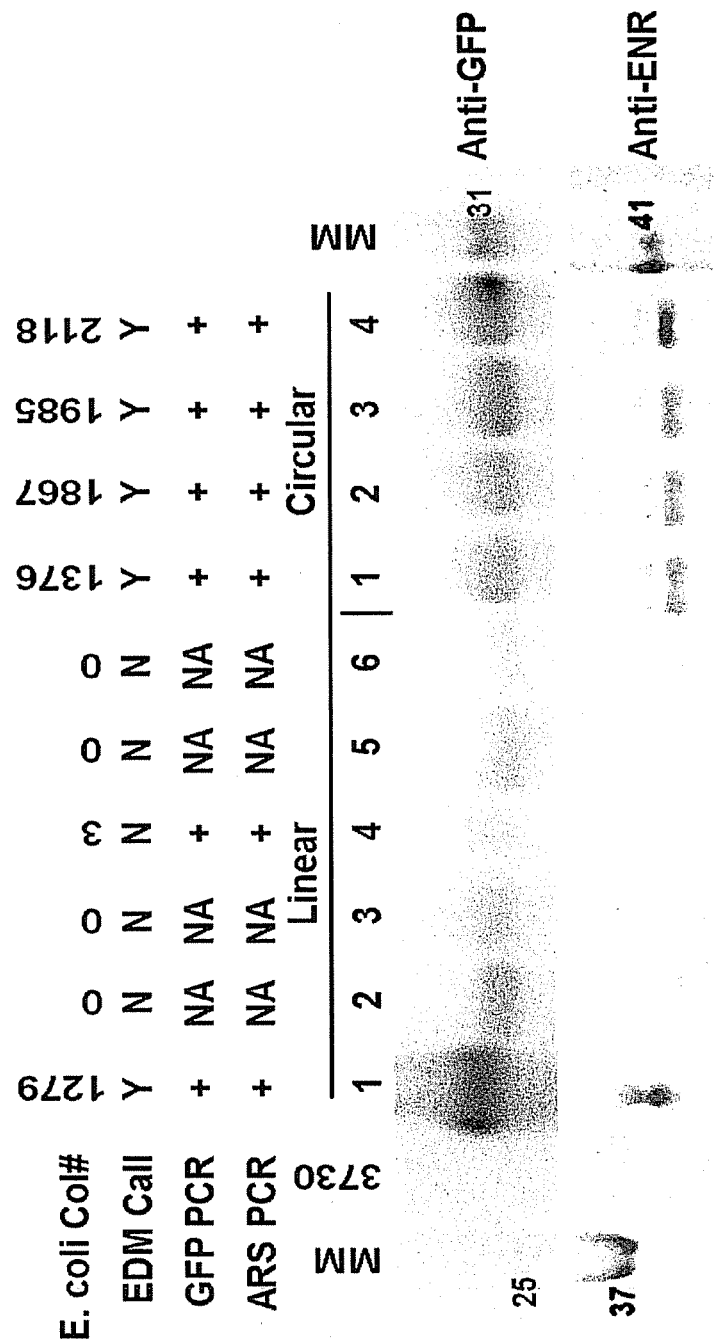
FIG. 7 is a photograph of a Western blot of extracts from *Nannochloropsis* lines transformed with a vector that included NgARS2. Separated proteins were detected with anti-GFP or anti-ENR antibodies. Above the lanes designated for each transformed *Nannochloropsis* line, data is provided on the number of colonies that resulted from transforming *E. coli* with the DNA extracted from that line, along with the results of PCR to detect the GFP gene and ARS, and a determination of whether the line was considered to be carrying an EDM ("EDM call").

In addition, Western blots were performed using extracts of the *Nannochloropsis* lines transformed with pSGE-6067 DNA. Briefly, *Nannochloropsis* cells were boiled in a lithium dodecyl sulfate/Urea/DTT protein loading solution and run on a NuPage gel, transferred to PVDF and probed with either anti-GFP or anti-ENR antibodies using standard techniques. FIG. 7 shows that the *Nannochloropsis* lines that included the pSGE-6067 construct in circular form (i.e., as an EDM) expressed GFP at a higher level than was found the blasticidin-resistant *Nannochloropsis* lines in which the pSGE-6067 was integrated into the genome. Further, *Nannochloropsis* lines that included the pSGE-6067 construct in circular form expressed the metabolically relevant ENR transgene, such that the protein was detectable, whereas no ENR protein was detected in the *Nannochloropsis* lines that included genome-integrated pSGE-6067 DNA. Thus, there appears to be a significant advantage for transgene expression in using EDMs in *Nannochloropsis*.

To complement the analysis of relative protein expression levels as determined by the Western blot, direct GFP fluorometric measurements of the cells within the transgenic populations was measured using a BD Accuri C6 flow cytometer. (BD Biosciences). Table 5 gives the amount of fluorescence per cell of ten cell lines. The highest GFP fluorescence, indicative of high levels of GFP expression, are found in lines 2C, 3L, 5L, 12L, and 15L, in which the pSGE-6081 construct is maintained as an EDM.

TABLE 5

| | Fluorescence | | |
| --- | --- | --- | --- |
| Strain | Mean fluorescence (FL1-A) | % cell in Peak 2 | Peak 2 Mean fluorescence (FL1-A) |
| WE3730 | 740.53 | 0.83% | 9,411.75 |
| 2C | 51,871.35 | 50.97% | 100,868.07 |
| 6C | 4,882.05 | 81.20% | 5,649.52 |
| 7C | 4,339.33 | 16.55% | 21,683.65 |
| 8C | 2,090.80 | 9.60% | 12,279.30 |
| 10C | 5,067.24 | 16.12% | 12,549.03 |
| 11C | 2,533.12 | 11.43% | 14,724.75 |
| 3L | 12,357.68 | 33.16% | 35,322.09 |
| 5L | 13,205.75 | 31.4% | 39,965.28 |
| 12L | 13,155.89 | 30.62% | 40,833.77 |
| 15L | 11,732.72 | 23.59% | 46,287.03 |

Example 7

Use of ARS Elements in Constructing Transient EDM Vectors

*Nannochloropsis* lines transformed with the EDM pSGE-06081, which contains the previously described blasticidin antibiotic resistance gene ("Blast 150"; SEQ ID NO:19) and TurboGFP reporter gene (SEQ ID NO:21) were generated. These lines were propagated in T75 tissue culture flasks containing 10 mL PM032 media with either 0 ug/mL or 75 ug/mL of blasticidin. The lines were passaged once per approximately 8 generations (approximately every 7 days) and the GFP fluorescence of the cells within the population at each of the passaging time periods was measured using the BD Accuri C6 Flow Cytometer. FIG. 8 shows the percent of the population that has GFP expression levels above background over time, with each date being a point where the cells were split into new media with the same antibiotic or no antibiotic composition. After approximately 2 weeks without selective pressure (no blasticidin in the media), the GFP expression levels were near background, and after approximately 4 weeks, no EDMs could be recovered. This demonstrates the potential of this EDM in providing a scaffold onto which genes can be deployed and maintained until antibiotic selective pressure is removed, at which point the EDM is diluted out of the population through cell division.

The results (Table 6) demonstrate that although cells of the culture that was under constant selection maintained the EDM, it was lost from cells of the culture that was released from antibiotic selection within 35 days. This result, together with the superior expression levels enabled by providing a gene on an EDM as compared to an integrated nucleic acid molecule (Example 6), indicates that transient expression of genes can be readily achieved by use of an EDM under selective conditions that maintain the EDM in the transformed line and allow for high expression levels, and subsequent removal of the selective agent to result in loss of the construct containing the transgene. Thus, EDMs as provided herein can be useful not only for testing functionality of genes and gene products (including gene attenuation constructs such as RNAi and antisense constructs), but also for transiently expressing genes for modifying the genome including, as nonlimiting examples, transposases, topoisomerases, recombinases, meganucleases, zinc finger nucleases, talens, CRISPR-associated endonucleases, etc.

Example embodiments are provided so that this disclosure will be thorough, and will fully convey the scope of the invention to those who are skilled in the art. Numerous specific details are set forth such as examples of specific components and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known structures, and well-known technologies are not described in detail.

The invention claimed is:

1. An isolated or recombinant nucleic acid molecule comprising an autonomous replication sequence (ARS) juxtaposed with at least one heterologous nucleic acid sequence, wherein the ARS has at least 95% identity to a nucleic acid selected from the group consisting of SEQ ID NO:5; SEQ ID NO:6; SEQ ID NO:7; SEQ ID NO:11; and SEQ ID NO:12, further wherein the ARS comprises a nucleic acid sequence having at least 98% identity to SEQ ID NO:14.

2. An isolated or recombinant nucleic acid molecule according to claim 1, wherein the nucleic acid molecule does not comprise a 35S ribosomal RNA gene unit.

3. An episomal DNA molecule (EDM) comprising an ARS that comprises a sequence having at least 95% identity to a nucleotide sequence selected from the group consisting of: SEQ ID NO:1; SEQ ID NO:5; SEQ ID NO:6; SEQ ID NO:7; SEQ ID NO:8; SEQ ID NO:9; SEQ ID NO:10; SEQ ID NO:11; and SEQ ID NO:12.

4. An EDM according to claim 3, wherein the ARS comprises a sequence having at least 98% identity to a nucleotide sequence selected from the group consisting of: SEQ ID NO:1, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

5. An EDM according to claim 4, wherein the ARS comprises the polynucleotide sequence selected from the group consisting of: SEQ ID NO:1, SEQ ID NO:5, SEQ ID NO:6, SEQ ID NO:7, SEQ ID NO:8, SEQ ID NO:9; SEQ ID NO:10; SEQ ID NO:11; and SEQ ID NO: 12.

6. An EDM according to claim 3, further comprising a nucleic acid sequence encoding a polypeptide.

7. An EDM according to claim 6, wherein the polypeptide is a reporter protein or selectable marker protein.

8. An EDM according to claim 7, wherein the reporter protein is a fluorescent protein or a signal producing enzyme.

9. An EDM according to claim 7, wherein the selectable marker protein is a protein that confers resistance to a drug, antibiotic, toxin, or herbicide; a protein that allows autotrophic growth on particular media; or a protein that prohibits growth on particular media.

10. An EDM according to claim 6, wherein polypeptide is a metabolic enzyme, structural protein, kinase, phosphatase, nucleotide cyclase, phosphodiesterase, nucleotide diesterase, transcriptional regulator, transcriptional activator, transporter, secretory protein, ion channel, receptor, photosynthetic protein, chaperonin, ribosomal protein, or nuclear scaffold protein.

11. An EDM according to claim 6, wherein the polypeptide is a meganuclease, a zinc finger nuclease, a TALEN protein, a cas protein, a recombinase, a topoisomerase, or a transposase.

12. An EDM according to claim 3, further comprising a nucleic acid sequence encoding a functional RNA.

13. An EDM according to claim 12, wherein the functional RNA is selected from the group consisting of an interfering RNA or a precursor thereof, an antisense RNA, a ribozyme, a micro RNA, and a guide RNA of a CRISPR system.

14. An EDM according to claim 3, wherein the ARS is functional in an algal or heterokont cell.

15. An EDM according to claim 3, wherein the EDM is circular.

16. An EDM according to claim 3, comprising sequences for mediating homologous or site specific recombination, wherein the sequences for homologous recombination flank a gene, a gene disruption sequence, or a functional RNA.

17. A method for propagating a gene of interest through at least 8 generations of cell division, the method comprising incorporating the gene of interest into the episomal DNA molecule of claim 3, transforming the episomal DNA molecule into a cell, and transforming the EDM into a host cell, and propagating the host cell for at least 8 generations.

18. A method according to claim 17, wherein the transformed cell is an algal, heterokont, plant, animal, fungal, or yeast cell.

19. A method according to claim 17, wherein the transformed cell is a *Nannochloropsis* cell.

20. A method for transiently expressing a gene or sequence of interest in a microbial cell, comprising transforming the EDM of claim 3 into a microbial cell and culturing the microbial cell under conditions in which the gene or sequence is expressed.

21. The method of claim 20, wherein the episomal DNA molecule comprises a selectable marker, and further wherein the microbial cell is cultured in the presence of a selective agent for one or more generations.

22. The method of claim 21, wherein the microbial cell is cultured in the presence of the selective agent for one or more generations and subsequently cultured in the absence of the selective agent for and additional one or more generations.

23. A method of transforming a microorganism, comprising: contacting at least one cell of the microorganism with an EDM according to claim 3, and selecting transformed cells on a selective medium.

24. An isolated or recombinant nucleic acid molecule according to claim 1, wherein the ARS has at least 98% identity to a nucleic acid sequence selected from the group consisting of SEQ ID NO:5, SEQ ID NO:6, SEQ ID NO:7, SEQ ID NO:11, and SEQ ID NO:12.

25. An isolated or recombinant nucleic acid molecule according to claim 24, wherein the ARS is selected from the group consisting of SEQ ID NO:5, SEQ ID NO:6, SEQ ID NO:7, SEQ ID NO:11, and SEQ ID NO:12.

26. An isolated or recombinant nucleic acid molecule according to claim 1, wherein the ARS has at least 95% identity to SEQ ID NO:6.

27. An isolated or recombinant nucleic acid molecule according to claim 26, wherein the ARS has at least 97% identity to SEQ ID NO:6.

28. An isolated or recombinant nucleic acid molecule according to claim 27, wherein the ARS comprises SEQ ID NO:6.

* * * * *